US012094082B2

(12) United States Patent
Makihira et al.

(10) Patent No.: US 12,094,082 B2
(45) Date of Patent: Sep. 17, 2024

(54) IMAGE PROCESSING APPARATUS, IMAGE PROCESSING METHOD AND COMPUTER-READABLE MEDIUM

(71) Applicant: CANON KABUSHIKI KAISHA, Tokyo (JP)

(72) Inventors: Tomoyuki Makihira, Tokyo (JP); Hiroki Uchida, Tokyo (JP); Ritsuya Tomita, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 366 days.

(21) Appl. No.: 17/343,207

(22) Filed: Jun. 9, 2021

(65) Prior Publication Data

US 2021/0304363 A1 Sep. 30, 2021

Related U.S. Application Data

(63) Continuation of application No. PCT/JP2019/050732, filed on Dec. 25, 2019.

(30) Foreign Application Priority Data

Dec. 26, 2018 (JP) .................... 2018-243769
Nov. 29, 2019 (JP) .................... 2019-217331

(51) Int. Cl.
*G06K 9/00* (2022.01)
*G06N 3/04* (2023.01)
(Continued)

(52) U.S. Cl.
CPC .............. *G06T 5/00* (2013.01); *G06N 3/04* (2013.01); *G06N 3/08* (2013.01); *G06T 7/0014* (2013.01);
(Continued)

(58) Field of Classification Search
CPC ........ G16H 40/67; G16H 15/00; G16H 30/20; G16H 50/30; G16H 50/70; G16H 50/20;
(Continued)

(56) References Cited

U.S. PATENT DOCUMENTS 6,351,660 B1 * 2/2002 Burke ................... G06T 7/0012
600/443
8,098,908 B2 * 1/2012 Vilser .................... G06T 7/246
382/128
(Continued)

FOREIGN PATENT DOCUMENTS

JP   2007-280229 A   10/2007
JP   2011-013334 A    1/2011
(Continued)

OTHER PUBLICATIONS

Gu, Ke, et al. "The analysis of image contrast: From quality assessment to automatic enhancement." IEEE transactions on cybernetics 46.1 (2015): 284-297. (Year: 2015).*
(Continued)

*Primary Examiner* — Avinash Yentrapati
(74) *Attorney, Agent, or Firm* — Carter, DeLuca & Farrell LLP

(57) ABSTRACT

An image processing apparatus includes: an obtaining unit configured to obtain a first medical image of an object under examination; an image quality improving unit configured to generate, from the obtained first medical image, a second medical image with image quality higher than image quality of the obtained first medical image using a learned model; a comparing unit configured to compare an analysis result obtained by analyzing the obtained first medical image and an analysis result obtained by analyzing the generated second medical image; and a display controlling unit con-
(Continued)

figured to cause a comparison result obtained by the comparing unit to be displayed on a display unit.

13 Claims, 26 Drawing Sheets

(51) Int. Cl.
| | |
|---|---|
| *G06N 3/08* | (2023.01) |
| *G06T 5/00* | (2006.01) |
| *G06T 7/00* | (2017.01) |
| *G06T 11/00* | (2006.01) |
| *G06T 11/60* | (2006.01) |
| *G16H 15/00* | (2018.01) |
| *G16H 30/20* | (2018.01) |
| *G16H 30/40* | (2018.01) |
| *G16H 40/67* | (2018.01) |
| *G16H 50/20* | (2018.01) |
| *G16H 50/30* | (2018.01) |
| *G16H 50/70* | (2018.01) |

(52) U.S. Cl.
CPC ............ *G06T 11/001* (2013.01); *G06T 11/60* (2013.01); *G16H 15/00* (2018.01); *G16H 30/20* (2018.01); *G16H 30/40* (2018.01); *G16H 40/67* (2018.01); *G16H 50/20* (2018.01); *G16H 50/30* (2018.01); *G16H 50/70* (2018.01); *G06T 2207/10101* (2013.01); *G06T 2207/20081* (2013.01); *G06T 2207/30041* (2013.01); *G06T 2210/41* (2013.01)

(58) Field of Classification Search
CPC . G16H 30/40; G06N 3/04; G06N 3/08; G06T 7/0014; G06T 11/001; G06T 11/60; G06T 2207/10101; G06T 2207/20081; G06T 2207/30041; G06T 2210/41
See application file for complete search history.

(56) References Cited

U.S. PATENT DOCUMENTS

| | | | | |
|---|---|---|---|---|
| 8,374,457 | B1* | 2/2013 | Wang ................. | G06T 5/70 382/302 |
| 9,439,562 | B2 | 9/2016 | Natsuhori et al. | |
| 9,566,002 | B2 | 2/2017 | Nakahara et al. | |
| 10,588,505 | B2 | 3/2020 | Natsuhori et al. | |
| 2013/0077839 | A1* | 3/2013 | Horz ................. | G06T 11/001 382/130 |
| 2014/0003695 | A1* | 1/2014 | Dean ................. | A61B 5/1075 382/131 |
| 2015/0332165 | A1* | 11/2015 | Mermoud ............ | G06N 5/048 706/12 |
| 2016/0278733 | A1* | 9/2016 | Ogura ................ | G06T 7/0012 |
| 2017/0231484 | A1 | 8/2017 | Komine | |
| 2017/0262988 | A1 | 9/2017 | Ikegami | |
| 2018/0199807 | A1 | 7/2018 | Ohta | |
| 2018/0330511 | A1 | 11/2018 | Ha | |
| 2019/0122360 | A1* | 4/2019 | Zhang ................. | G06F 18/24 |
| 2021/0104313 | A1 | 4/2021 | Mizobe et al. | |
| 2021/0158525 | A1 | 5/2021 | Iwase et al. | |
| 2021/0183019 | A1 | 6/2021 | Uchida et al. | |
| 2021/0224957 | A1 | 7/2021 | Iwase et al. | |
| 2021/0224997 | A1 | 7/2021 | Kushida et al. | |

FOREIGN PATENT DOCUMENTS

| | | |
|---|---|---|
| JP | 2014-149713 A | 8/2014 |
| JP | 2018-005841 A | 1/2018 |
| JP | 2018-089160 A | 6/2018 |
| WO | 2014167935 A1 | 10/2014 |
| WO | 2017-155015 A1 | 9/2017 |
| WO | 2018039380 A1 | 3/2018 |

OTHER PUBLICATIONS

Xiao, Bin, et al. "Histogram learning in image contrast enhancement." Proceedings of the IEEE/CVF Conference on Computer Vision and Pattern Recognition Workshops. 2019. (Year: 2019).*
Chinese Office Action issued in corresponding CN Patent Application No. 201980086346.9, dated Jul. 27, 2023, with English translation.
International Preliminary Report on Patentability issued by the International Bureau of WIPO on behalf of the JP Patent Office acting as International Searching Authority on Jun. 16, 2021 in corresponding International Application No. PCT/JP2019/050732, with English translation.
International Search Report issued by the Japan Patent Office on Mar. 3, 2020 in corresponding International Application No. PCT/JP2019/050732, with English translation.
Wu, D.F. et al., "Iterative Low-Dose CT Reconstruction With Priors Trained by Artificial Neural Network" IEEE Transactions on Medical Imaging (2017) pp. 2479-2486, vol. 36, No. 12.
Hasegawa, A. "Noise reduction processing by AI—PixelShine" Innervision (Jun. 2017) pp. 31-34, vol. 32, No. 7, with English abstract.
Notice of Reasons for Refusal issued by the Japanese Patent Office on May 23, 2023 in corresponding JP Patent Application No. 2019-217331, with English translation.
Sheet, D. et al., "Deep Learning of Tissue Specific Speckle Representations in Optical Coherence Tomography and Deeper Exploration for in Situ Histology" IEEE International Symposium on Biomedical Imaging (Apr. 2015) pp. 777-780.
Chinese Office Action issued in corresponding CN Patent Application No. 201980086346.9, dated Jan. 6, 2024, with English Translation.
Qing, Y. et al., "Application of optical coherence tomography angiography in neuro-ophthalmological diseases" New Adv Ophthalmol (Aug. 2018) pp. 794-796, vol. 38, No. 8, with English abstract.
Chinese Notice of Grant of Patent Invention issued by the China National Intellectual Property Administration on Jul. 12, 2024 in corresponding CN Patent Application No. 201980086346.9, with English translation.

* cited by examiner

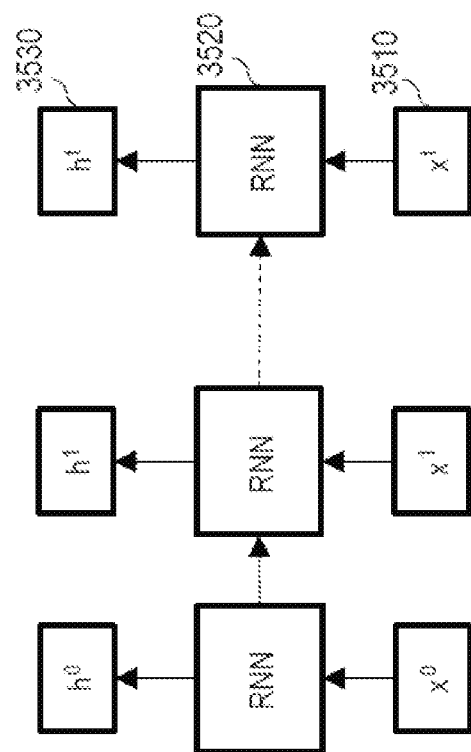

IMAGE PROCESSING APPARATUS, IMAGE PROCESSING METHOD AND COMPUTER-READABLE MEDIUM

CROSS-REFERENCE TO RELATED APPLICATIONS

This application is a Continuation of International Patent Application No. PCT/JP2019/050732, filed Dec. 25, 2019, which claims the benefit of Japanese Patent Application No. 2018-243769, filed Dec. 26, 2018, and Japanese Patent Application No. 2019-217331, filed Nov. 29, 2019, all of which are hereby incorporated by reference herein in their entirety.

BACKGROUND OF THE INVENTION

Field of the Invention

The present invention relates to an image processing apparatus, an image processing method and a computer-readable medium.

Description of the Related Art

An apparatus (OCT apparatus) that utilizes optical coherence tomography (OCT) is in practical use as a method for nondestructively and noninvasively obtaining tomographic images of an object under examination, such as a living organism. An OCT apparatus is widely used in particular as an ophthalmic apparatus that acquires images for ophthalmic diagnosis.

In OCT, a tomographic image of an object under examination can be obtained by causing light reflected from a measurement object and light reflected from a reference mirror to interfere with each other, and analyzing the intensity of the interference light. Time domain OCT (TD-OCT) is known as one kind of such OCT. In TD-OCT, depth information for the object under examination is obtained by successively changing the position of the reference mirror.

Spectral domain OCT (SD-OCT) and swept source OCT (SS-OCT) are also known. In SD-OCT, interference light obtained by causing light interference using low-coherence light is divided, and depth information is replaced with frequency information to thereby acquire the frequency information. In SS-OCT, interference light is acquired by using light whose wavelength has been divided in advance using a wavelength-swept light source. Note that, SD-OCT and SS-OCT are also referred to collectively as "Fourier domain OCT (FD-OCT)".

By using OCT, tomographic images that are based on depth information of the object under examination can be acquired. Further, by integrating acquired three-dimensional tomographic images in the depth direction and projecting the integrated image onto a two-dimensional plane, a front image of the measurement object can be generated. Conventionally, to improve the image quality of these images, images are acquired a plurality of times and averaging processing is performed. However, in such a case, it takes time to perform imaging a plurality of times.

Japanese Patent Application Laid-Open No. 2018-5841 discloses technology that, in order to respond to the rapid advances being made in medical techniques and also to correspond to simple imaging in an emergency, converts a previously acquired image into an image with higher resolution by means of an artificial intelligence engine. According to this technology, for example, images acquired by performing imaging a fewer number of times can be converted into an image with a higher resolution.

However, even when an image has a high resolution, there are cases in which it cannot be said that the image is an image that is suitable for image diagnosis. For example, even when the resolution of an image is high, if there is a large amount of noise or the contrast is low or the like in the image, in some cases an object that should be observed cannot be appropriately ascertained.

In this regard, one objective of the present invention is to provide an image processing apparatus, an image processing method and a computer-readable medium having stored thereon a program, which can generate an image that is more suitable for image diagnosis than in the conventional technology.

SUMMARY OF THE INVENTION

An image processing apparatus according to one embodiment of the present invention includes: an obtaining unit configured to obtain a first medical image of an object under examination, an image quality improving unit configured to generate, from the obtained first medical image, a second medical image with image quality higher than image quality of the obtained first medical image using a learned model; a comparing unit configured to compare an analysis result obtained by analyzing the obtained first medical image and an analysis result obtained by analyzing the generated second medical image; and a display controlling unit configured to cause a comparison result obtained by the comparing unit to be displayed on a display unit.

Further features of the present invention will become apparent from the following description of exemplary embodiments with reference to the attached drawings.

BRIEF DESCRIPTION OF THE DRAWINGS

FIG. 18A is a view illustrating an example of the configuration of the neural network used as the machine learning model according to Modification 12.

DESCRIPTION OF THE EMBODIMENTS

Figure 1:
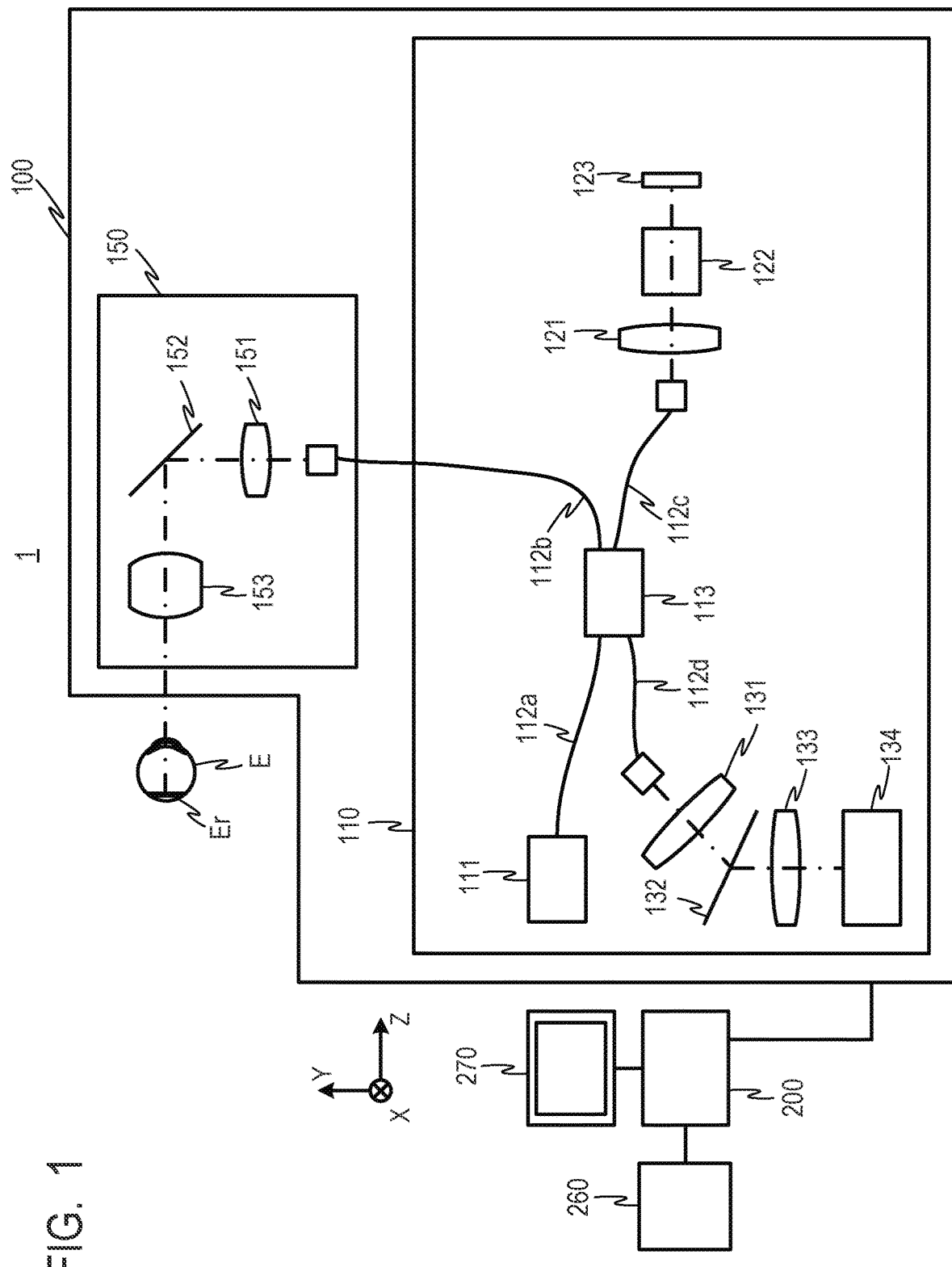
FIG. 1 is a view illustrating a schematic configuration of an OCT apparatus according to Embodiment 1.

Exemplary embodiments of the present invention will now be described in detail in accordance with the accompanying drawings.

However, the dimensions, materials, shapes and relative positions of the components described in the following embodiments are not determinate, and can be changed according to a configuration of an apparatus to which the present invention is applied or to various conditions. Further, identical or functionally similar elements are denoted by the same reference numerals in different drawings.

In the following embodiments, while an eye to be examined is given as an example of an object (subject) under examination, another organ of a human or the like may be taken as the object under examination. Further, an OCTA (OCT angiography) image of an eye to be examined is described as an example of an image on which image quality improving processing is performed using a learned model relating to a machine learning model (machine learning engine). Note that, the term "OCTA" refers to angiography that uses OCT without using a contrast medium. In OCTA, an OCTA image (front blood vessel image, or motion contrast front image) is generated by integrating three-dimensional motion contrast data obtained based on depth information of the object under examination in the depth direction, and projecting the integrated data onto a two-dimensional plane.

Here, the term "motion contrast data" refers to data obtained by repeatedly imaging approximately the same location of an object under examination, and detecting changes over time in the object during the imaging. Note that, the phrase "approximately the same location" refers to a position that is the same to a degree that is allowable for generating motion contrast data, and includes a location that deviates slightly from a location that is strictly the same location. Motion contrast data is obtained by, for example, calculating changes over time in phases, vectors or intensities of complex OCT signals based on differences, ratios or correlations or the like.

Important points relating to image quality improving processing using a learned model relating to a machine learning model will now be mentioned. By performing image quality improving processing on an image using a learned model relating to a machine learning model, although on one hand a high-quality image can be obtained from a small number of images, on the other hand in some cases tissue that does not actually exist is visualized in an image or tissue that originally exists is not visualized in an image. Consequently, there is the problem that it is difficult to determine the authenticity of tissue visualized in an image subjected to image quality improving by performing image quality improving processing using a learned model.

Therefore, in the following embodiments, an image processing apparatus is provided which, by using a machine learning model, can generate an image that is more suitable for image diagnosis than in the conventional technology, and with respect to such an image, can also easily determine the authenticity of tissue visualized in the image.

Note that, although an OCTA image is described in the following embodiments, an image on which image quality improving processing is performed is not limited thereto, and may be a tomographic image or an intensity en-face image or the like. Here, the term "en-face image" refers to a front image generated by, with respect to three-dimensional data of the object under examination, projecting or integrating data within a predetermined depth range determined based on two reference planes onto a two-dimensional plane. Examples of en-face images include an intensity en-face image that is based on an intensity tomographic image and an OCTA image (motion contrast front image, or motion contrast en-face image) that is based on motion contrast data.

Embodiment 1

Hereunder, an optical coherence tomography apparatus (OCT apparatus) and an image processing method according to Embodiment 1 of the present invention are described referring to FIG. 1 to FIG. 7. FIG. 1 is a schematic configuration of an OCT apparatus according to the present embodiment.

An OCT apparatus 1 according to the present embodiment includes an OCT imaging unit 10, a controlling unit (image processing apparatus) 200, an inputting unit 260, and a display unit 270.

The OCT imaging unit 100 includes an imaging optical system of an SD-OCT apparatus, and acquires a signal including tomographic information of an eye to be examined E, based on interference light generated by causing return light from the eye to be examined E at which measuring light was irradiated through a scanning unit, and reference light corresponding to the measuring light to interfere with each other. An optical interference unit 110 and a scanning optical system 150 are provided in the OCT imaging unit 100.

The controlling unit 200 can control the OCT imaging unit 100, generate an image from a signal obtained from the OCT imaging unit 100 or another apparatus (not illustrated), and process a generated/acquired image. The display unit 270 is any display such as an LCD display, and can display a GUI for operating the OCT imaging unit 100 and the controlling unit 200, a generated image, an image on which any kind of processing was performed, and various kinds of information such as patient information.

The inputting unit 260 is used for operating the controlling unit 200 by operating the GUI and by inputting information. The inputting unit 260 includes, for example, a pointing device such as a mouse, a touchpad, a trackball, a touch panel display or a stylus pen, and a keyboard. Note that, in the case of using a touch panel display, the display unit 270 and the inputting unit 260 can be constituted integrally with each other. Note that, although in the present embodiment the OCT imaging unit 100, the controlling unit 200, the inputting unit 260 and the display unit 270 are assumed to be separate units to each other, some or all of these units may be constituted integrally with each other.

A light source 111, a coupler 113, a collimating optical system 121, a dispersion compensation optical system 122, a reflection mirror 123, a lens 131, a diffraction grating 132, an imaging lens 133, and a line sensor 134 are provided in the optical interference unit 110 in the OCT imaging unit 100. The light source 111 is a low-coherence light source that emits near-infrared light. Light emitted from the light source Ill propagates through an optical fiber 112a and enters the coupler 113 that is a light splitting unit. The light that entered the coupler 113 is split into measuring light which travels toward a scanning optical system 150 side, and reference light which travels toward a reference light optical system side that includes the collimating optical system 121, the dispersion compensation optical system 122 and the reflection mirror 123. The measuring light enters an optical fiber 112b and is guided to the scanning optical system 150. On the other hand, the reference light enters an optical fiber 112c and is led to the reference light optical system.

The reference light that entered the optical fiber 112c is emitted from a fiber end, and is incident on the dispersion compensation optical system 122 through the collimating optical system 121 and is guided to the reflection mirror 123. The reference light that is reflected by the reflection mirror 123 follows the optical path in an opposite direction and enters the optical fiber 112c once again. The dispersion compensation optical system 122 is a component for compensating for dispersion of the optical system with respect to the scanning optical system 150 and the eye to be examined E that is the object under examination, and causing the dispersion of the measuring light to match with the dispersion of the reference light. The reflection mirror 123 is configured to be drivable in a direction of an optical axis of the reference light by a driving unit (not illustrated) controlled by the controlling unit 200, and can cause an optical path length of the reference light to change relatively with respect to an optical path length of the measuring light and cause the optical path lengths of the reference light and the measuring light to match.

On the other hand, the measuring light that entered the optical fiber 112b is emitted from the fiber end, and is incident on the scanning optical system 150. The scanning optical system 150 is an optical system configured to be movable relatively with respect to the eye to be examined E. The scanning optical system 150 is configured to be drivable in front, rear, upward, downward, left and right directions with respect to an axis of an eyeball of the eye to be examined E by a driving unit (not illustrated) controlled by the controlling unit 200, and can perform alignment with respect to the eye to be examined E. Note that, the scanning optical system 150 may be configured to include the light source 111, the coupler 113 and the reference light optical system or the like.

A collimating optical system 151, a scanning unit 152 and a lens 153 are provided in the scanning optical system 150. Light emitted from the fiber end of the optical fiber 112b is substantially collimated by the collimating optical system 151, and is incident on the scanning unit 152.

The scanning unit 152 has two galvanometer mirrors capable of rotating a mirror surface, one of which deflects light in a horizontal direction and the other of which deflects light in a vertical direction. The scanning unit 152 deflects the incident light according to control by the controlling unit 200. By this means, the scanning unit 152 can scan the measuring light on a fundus Er of the eye to be examined E in two directions, namely, a main scanning direction that is a direction perpendicular to the paper surface (X-direction) and a sub-scanning direction that is a direction parallel to the paper surface (Y-direction). Note that, the main scanning direction and the sub-scanning direction are not limited to the X-direction and the Y-direction, and it suffices that the main scanning direction and the sub-scanning direction are directions which are perpendicular to the depth direction (Z-direction) of the eye to be examined E. and which intersect with each other. Therefore, for example, the main scanning direction may be the Y-direction, and the sub-scanning direction may be the X-direction.

The measuring light scanned by the scanning unit 152 forms an illumination spot on the fundus Er of the eye to be examined E via the lens 153. Upon receiving in-plane deflection by the scanning unit 152, each illumination spot moves (scans) over the fundus Er of the eye to be examined E. Return light of the measuring light which was reflected and scattered from the fundus Er at the position of the illumination spot follows along the optical path in the opposite direction, enters the optical fiber 112b, and returns to the coupler 113.

As described above, the reference light reflected by the reflection mirror 123 and the return light of the measuring light from the fundus Er of the eye to be examined E are returned to the coupler 113 and interfere with each other to become interference light. The interference light passes through the optical fiber 112d and is emitted to the lens 131. The interference light is substantially collimated by the lens 131, and is incident on the diffraction grating 132. The diffraction grating 132 has a periodic structure, and splits the incident interference light. The interference light that was split is imaged on the line sensor 134 by the imaging lens 133 whose focal state can be changed. The line sensor 134 outputs a signal corresponding to the intensity of light irradiated onto each sensor unit to the controlling unit 200. The controlling unit 200 can generate a tomographic image of the eye to be examined E based on the interference signal output from the line sensor 134.

Tomographic information pertaining to the depth direction at one point of the eye to be examined E can be acquired through the series of operations described above. Such a series of operations is referred to as an "A-scan".

Further, by driving the galvanometer mirror of the scanning unit 152, interference light at one point adjacent to the eye to be examined E is generated, and tomographic information in the depth direction at one point adjacent to the eye to be examined E is acquired. By performing the A-scan a plurality of times in an arbitrary transverse direction (main scanning direction) by repeating this series of controls, two-dimensional tomographic information of the eye to be examined E can be acquired in the aforementioned transverse direction and the depth direction. Such an operation is referred to as a "B-scan". The controlling unit 200 can construct one B-scan image by collecting a plurality of A-scan images based on interference signals acquired by the A-scans. Hereinafter, the B-scan image is referred to as a "two-dimensional tomographic image".

In addition, tomographic information can be acquired at another position (an adjacent scanning line) of the eye to be examined E by slightly driving the galvanometer mirror of the scanning unit 152 in the sub-scanning direction that is orthogonal to the main scanning direction. By collecting a plurality of B-scan images by repeating this operation, the controlling unit 200 can acquire a three-dimensional tomographic image in a predetermined range of the eye to be examined E.

Figure 2:
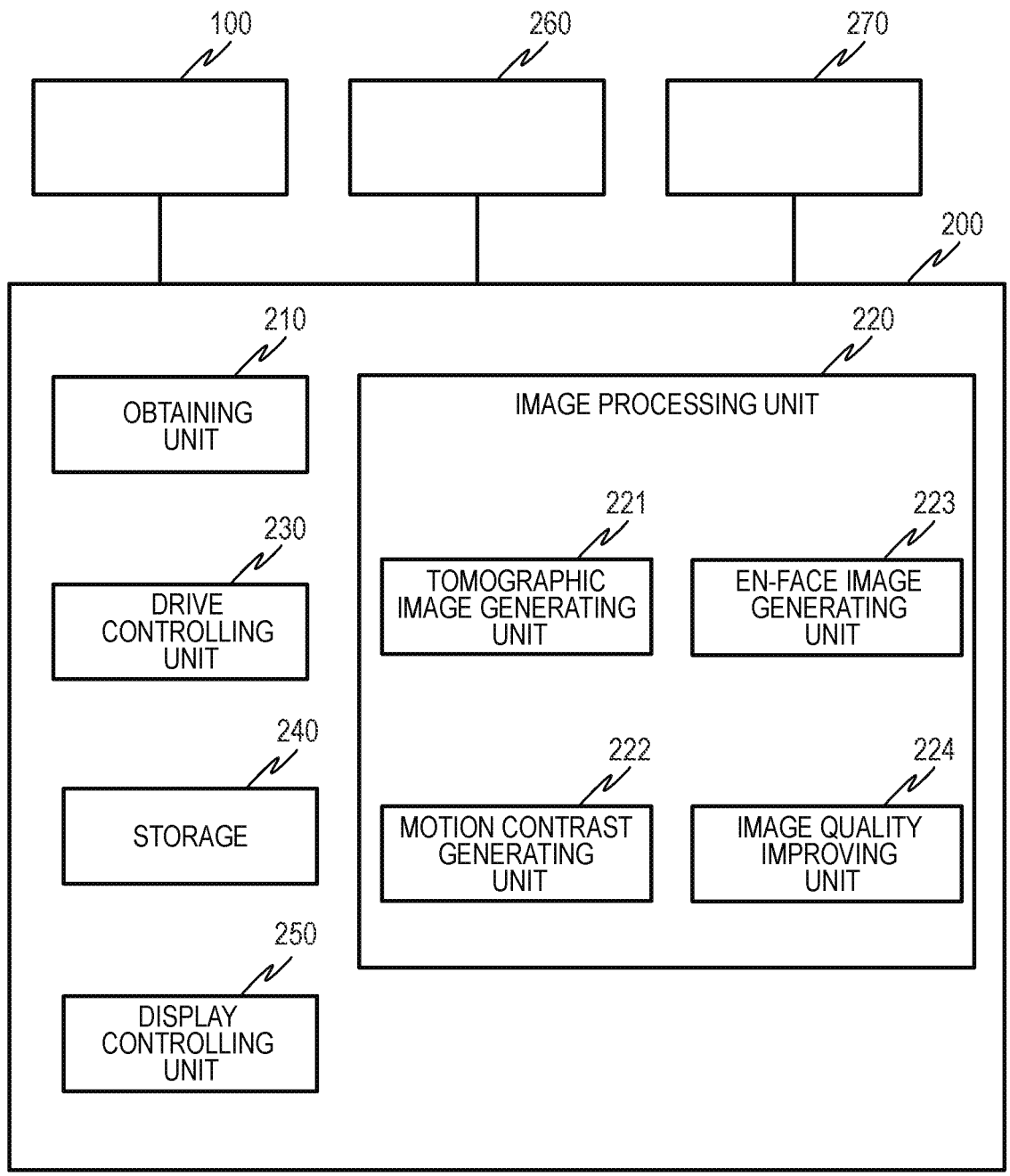
FIG. 2 is a view illustrating a schematic configuration of a controlling unit according to Embodiment 1.

Next, the controlling unit 200 will be described referring to FIG. 2. FIG. 2 illustrates a schematic configuration of the controlling unit 200. An obtaining unit 210, an image processing unit 220, a drive controlling unit 230, a storage 240 and a display controlling unit 250 are provided in the controlling unit 200.

The obtaining unit 210 can obtain data of an output signal of the line sensor 134 corresponding to an interference signal of the eye to be examined E, from the OCT imaging unit 100. Note that, the data of the output signal that the obtaining unit 210 obtains may be an analog signal or a digital signal. In a case where the obtaining unit 210 obtains an analog signal, the controlling unit 200 can convert the analog signal into a digital signal.

Further, the obtaining unit 210 can obtain tomographic data generated by the image processing unit 220, and various kinds of images such as a two-dimensional tomographic image, a three-dimensional tomographic image, a motion contrast image and an en-face image. Here, the term "tomographic data" refers to data including information relating to a cross-section of an object under examination, and includes a signal obtained by subjecting an interference signal obtained by OCT to Fourier transformation, a signal obtained by subjecting the relevant signal to any processing, and a tomographic image or the like based on these signals.

In addition, the obtaining unit 210 obtains an imaging conditions group (for example, information relating to the imaging date and time, an imaged site name, an imaged region, an imaging angle of view, an imaging system, an image resolution and gradation, an image size, an image filter, and the image data format) of the image to be subjected to image processing. Note that the imaging conditions group is not limited to the example of an imaging conditions group described in the foregoing. Further, the imaging conditions group need not include all of the conditions mentioned in the foregoing example, and may include some of these conditions.

Specifically, the obtaining unit 210 obtains the imaging conditions of the OCT imaging unit 100 when imaging the relevant image. Further, depending on the data format of the image, the obtaining unit 210 can also obtain an imaging conditions group that is stored in a data structure constituting the image. Note that, in a case where imaging conditions are not stored in the data structure of the image, the obtaining unit 210 can also separately obtain an imaging information group that includes an imaging conditions group from a storage apparatus or the like that stores the imaging conditions.

Further, the obtaining unit 210 can also obtain information for identifying the eye to be examined, such as a subject identification number, from the inputting unit 260 or the like. Note that, the obtaining unit 210 may obtain various kinds of data, various kinds of images or various kinds of information from the storage 240 or another apparatus (not illustrated) connected to the controlling unit 200. The obtaining unit 210 can store various kinds of data or images that were obtained in the storage 240.

The image processing unit 220 can generate a tomographic image or an en-face image or the like from data obtained by the obtaining unit 210 or data stored in the storage 240, and can perform image processing on a generated or obtained image. A tomographic image generating unit 221, a motion contrast generating unit 222, an en-face image generating unit 223 and an image quality improving unit 224 are provided in the image processing unit 220.

The tomographic image generating unit 221 can subject the interference signal data obtained by the obtaining unit 210 to wavenumber conversion, Fourier transformation, absolute value conversion (acquisition of amplitude) or the like to generate tomographic data, and can generate a tomographic image of the eye to be examined E based on the tomographic data. The interference signal data obtained by the obtaining unit 210 may be data of a signal that was output from the line sensor 134, or may be data of an interference signal obtained from the storage 240 or an apparatus (not illustrated) connected to the controlling unit 200. Note that, any known method may be adopted as a method for generating a tomographic image, and a detailed description thereof is omitted here.

The tomographic image generating unit 221 can also generate a three-dimensional tomographic image based on the generated tomographic images of a plurality of sites. The tomographic image generating unit 221, for example, can generate a three-dimensional tomographic image by arranging tomographic images of a plurality of sites side-by-side in one coordinate system. Here, the tomographic image generating unit 221 may generate a three-dimensional tomographic image based on tomographic images of a plurality of sites obtained from the storage 240 or an apparatus (not illustrated) connected to the controlling unit 200.

The motion contrast generating unit 222 can generate a two-dimensional motion contrast image using a plurality of tomographic images obtained by imaging approximately the same location. Further, the motion contrast generating unit 222 can generate a three-dimensional motion contrast image by arranging generated two-dimensional motion contrast images of respective sites side-by-side in one coordinate system.

In the present embodiment, the motion contrast generating unit 222 generates a motion contrast image based on decorrelation values between a plurality of tomographic images obtained by imaging approximately the same location of the eye to be examined E.

Specifically, the motion contrast generating unit 222 acquires a plurality of tomographic images on which alignment was performed with respect to a plurality of tomographic images obtained by imaging approximately the same location for which the imaging times are continuous with each other. Note that, various known methods can be used as the alignment method. For example, one reference image is selected among the plurality of tomographic images, the degree of similarity with the other tomographic images is calculated while changing the position and angle of the reference image, and the amount of displacement of each tomographic image relative to the reference image is calculated. Alignment of the plurality of tomographic images is then performed by correcting each tomographic image based on the calculation results. Note that, processing for the alignment may be performed by a separate component from the motion contrast generating unit 222. Further, the alignment method is not limited to this method, and alignment may be performed by any known method.

The motion contrast generating unit 222 uses the following mathematical expression 1 to calculate decorrelation values for each two tomographic images whose imaging times are continuous with each other among the plurality of tomographic images on which alignment was performed.

$$M(x, z) = 1 - 2 \times \frac{A(x, z) \times B(x, z)}{A(x, z)^2 + B(x, z^2)}$$ mathematical expression 1

Here, A(x,z) represents the amplitude at a position (x,z) of a tomographic image A, and B(x,z) represents the amplitude at the same position (x,z) of a tomographic image B. A decorrelation value M (x,z) obtained as a result takes a value from 0 to 1, and becomes closer to 1 as the difference between the two amplitude values increases. Note that, although a case of using two-dimensional tomographic images on the X-Z plane has been described in the present embodiment, for example two-dimensional tomographic images on the Y-Z plane or the like may be used. In such a case, the position (x,z) may be replaced with the position (y,z) or the like. Note that, the decorrelation value may be determined based on intensity values of the tomographic images, or may be determined based on values of interference signals corresponding to the tomographic images.

The motion contrast generating unit 222 determines pixel values of the motion contrast image based on the decorrelation value M(x,z) at each position (pixel position), and generates a motion contrast image. Note that, although in the present embodiment the motion contrast generating unit 222 calculates decorrelation values with respect to tomographic images whose imaging times are continuous with each other, a method for calculating motion contrast data is not limited thereto. The imaging times of two tomographic images for which a decorrelation value M is obtained need not be continuous with each other, and it suffices that imaging times relating to the respective tomographic image which correspond to each other are within a predetermined time interval. Therefore, for example, for the purpose of extracting an object for which a change over time is small, two tomographic images for which the imaging interval is longer than a normal specified time may be extracted from an acquired plurality of tomographic images and the decorrelation values may be calculated. Further, instead of a decorrelation value, a variance value or a value obtained by dividing the maximum value by the minimum value (maximum value/minimum value) or the like may be determined.

Note that, a method for generating a motion contrast image is not limited to the aforementioned method, and any other known method may also be used.

The en-face image generating unit 223 can generate an en-face image (OCTA image) that is a front image from a three-dimensional motion contrast image which the motion contrast generating unit 222 generated. Specifically, the en-face image generating unit 223 can generate an OCTA image that is a front image by projecting the three-dimensional motion contrast image on a two-dimensional plane based on, for example, two arbitrary reference planes in the depth direction (Z direction) of the eye to be examined E.

Further, the en-face image generating unit 223 can generate an intensity en-face image in a similar manner from a three-dimensional tomographic image which the tomographic image generating unit 221 generated.

The en-face image generating unit 223, more specifically, for example, determines a representative value of pixel values in the depth direction at each position in the X-Y direction of a region surrounded by two reference planes, determines a pixel value at each position based on the representative value, and generates an en-face image. In this case, examples of the representative value include an average value, median value or maximum value of pixel values within a range in the depth direction of the region surrounded by the two reference planes.

Note that, a reference plane may be a plane along a layer boundary at a cross-section of the eye to be examined E, or may be a plane. Hereinafter, a range in the depth direction between reference planes for generating an en-face image is referred to as an "en-face image generation range". Further, the method for generating an en-face image according to the present embodiment is one example, and the en-face image generating unit 223 may generate an en-face image using any known method.

The image quality improving unit 224 uses a learned model that is described later to generate a high quality OCTA image based on an OCTA image generated by the en-face image generating unit 223. Further, the image quality improving unit 224 may generate a high quality tomographic image or a high quality intensity en-face image based on a tomographic image generated by the tomographic image generating unit 221 or an intensity en-face image generated by the en-face image generating unit 223. Note that, the image quality improving unit 224 can also generate a high quality image based on various kinds of images that the obtaining unit 210 obtained from the storage 240 or another apparatus (not illustrated) connected to the controlling unit 200, and not just based on an OCTA image that was imaged using the OCT imaging unit 100 or the like. In addition, the image quality improving unit 224 may perform image quality improving processing on a three-dimensional motion contrast image or a three-dimensional tomographic image, and not just an OCTA image or a tomographic image.

The drive controlling unit 230 can control driving of components such as the light source 111, the scanning optical system 150, the scanning unit 152 and the imaging lens 133 of the OCT imaging unit 100 which is connected to the controlling unit 200. The storage 240 can store various kinds of data obtained by the obtaining unit 210, and various kinds of data and images such as a tomographic image or an OCTA image which was generated and processed by the image processing unit 220. Further, the storage 240 can store attributes (name, age, or the like) of a subject, information relating to the eye to be examined such as measurement results (axial length of eyeball, intraocular pressure, or the like) acquired using other inspection equipment, imaging parameters, image analysis parameters, and parameters set by the operator. Note that, a configuration may also be adopted in which these images and information are stored in an external storage apparatus (not illustrated). The storage 240 can also store a program for carrying out the functions of the respective components of the controlling unit 200 by being executed by a processor.

The display controlling unit 250 can cause various kinds of information obtained by the obtaining unit 210 and various kinds of images such as a tomographic image, an OCTA image and a three-dimensional motion contrast image which were generated and processed by the image processing unit 220 to be displayed on the display unit 270. The display controlling unit 250 can also cause information that was input by a user and the like to be displayed on the display unit 270.

The controlling unit 200 may be constituted, for example, by using a general-purpose computer. Note that, the controlling unit 200 may be constituted by using a dedicated computer of the OCT apparatus 1. The controlling unit 200 is equipped with a CPU (central processing unit) (not illustrated) or MPU (micro processing unit) and a storage medium including a memory such as an optical disk or ROM (read only memory). The respective components other than the storage 240 of the controlling unit 200 may be constituted by a software module that is executed by a processor such as a CPU or an MPU. Further, the respective components in question may be constituted by a circuit that serves a specific function such as an ASIC, or an independent apparatus or the like. The storage 240, for example, may be constituted by any storage medium such as an optical disk or a memory.

Note that, the controlling unit 200 may include one or a plurality of processors such as a CPU and storage media such as ROM. Therefore, each component of the controlling unit 200 may be configured to function in a case where at least one or more processors and at least one storage medium are connected, and at least one or more processors executes a program stored in at least one storage medium. Note that, the processor is not limited to a CPU or an MPU, and may be a GPU (graphics processing unit) or the like.

Figure 3A:
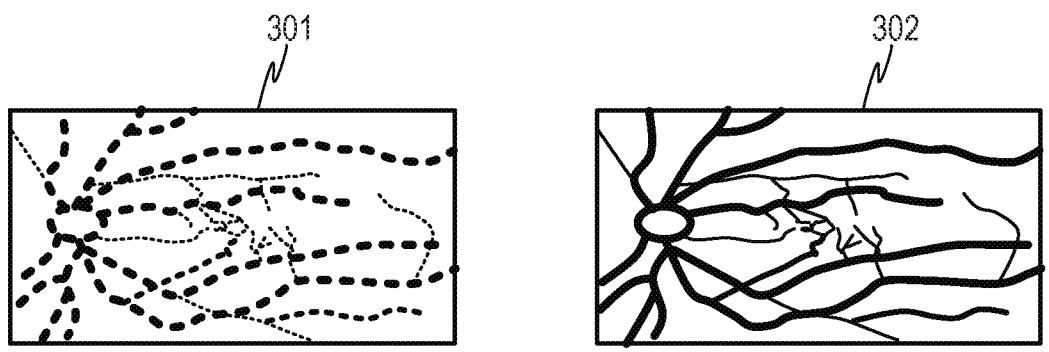
FIG. 3A is a view illustrating an example of training data according to Embodiment 1.
Figure 3B:
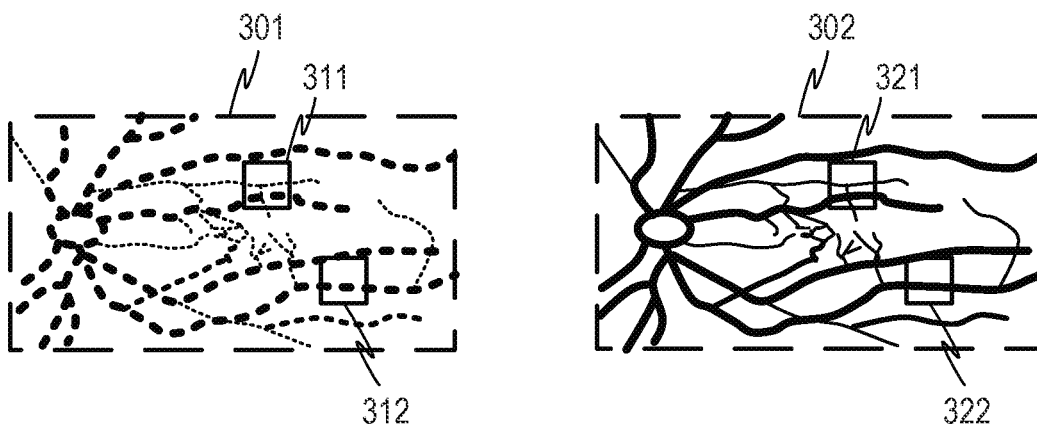
FIG. 3B is a view illustrating an example of training data according to Embodiment 1.
Figure 4:
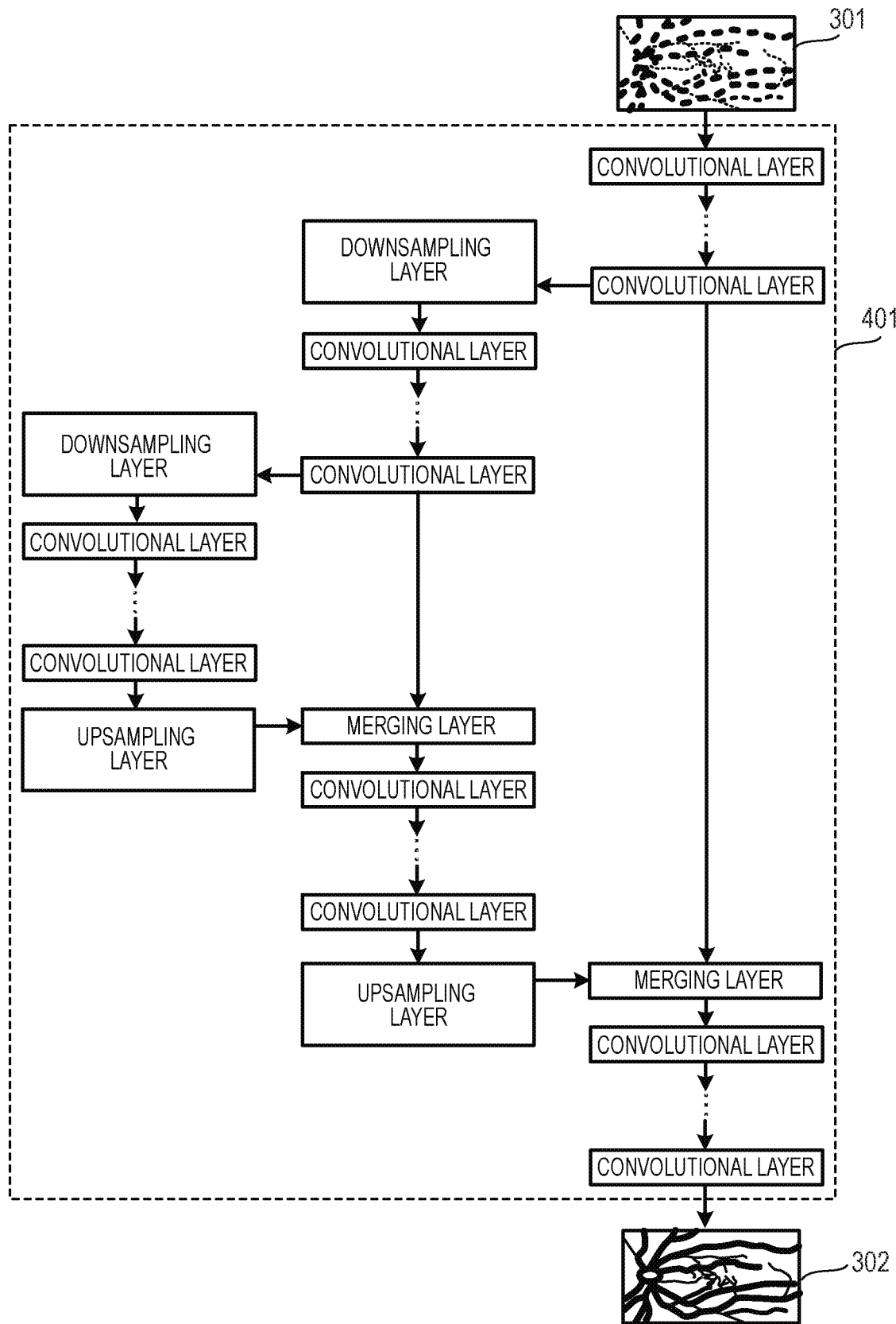
FIG. 4 is a view illustrating an example of a configuration of a learned model according to Embodiment 1.

Next, a learned model relating to a machine learning model in accordance with a machine learning algorithm such as deep learning according to the present embodiment is described referring to FIG. 3A to FIG. 4. A learned model according to the present embodiment generates and outputs an image on which image quality improving processing was performed based on an input image according to the learning tendency.

In the present description the term "image quality improving processing" refers to converting an input image into an image with image quality that is more suitable for image diagnosis, and the term "high quality image" refers to an image that has been converted into an image with image quality that is more suitable for image diagnosis. Here, the content of image quality which is suitable for image diagnosis depends on what it is desired to diagnose using various kinds of image diagnosis. Therefore, while it is not possible to say so unconditionally, for example, image quality that is suitable for image diagnosis includes image quality in which the amount of noise is low, the contrast is high, the imaging target is displayed in colors and gradations which make the imaging target easy to observe, the image size is large and the resolution is high. In addition, image quality that is suitable for image diagnosis can include image quality such that objects or gradations which do not actually exist that were rendered during the process of image generation are removed from the image.

The term "learned model" refers to, with respect to a machine learning model in accordance with any machine learning algorithm such as deep learning, a model which performed training (learning) using appropriate training data in advance. However, it is assumed that the learned model is not a model that does not perform further learning, and is a model that can also perform incremental learning. The training data is composed of one or more pair groups composed of input data and ground truth (correct answer data). In the present embodiment, a pair composed of input data and ground truth is constituted by an OCTA image, and an OCTA image obtained by subjecting a plurality of OCTA images including the aforementioned OCTA image to averaging processing such as addition averaging.

An averaged image that underwent averaging processing is a high quality image that is suitable for image diagnosis because pixels that are commonly visualized in a source image group are enhanced. In this case, as a result of pixels commonly visualized being enhanced, the generated high quality image is a high contrast image in which a difference between a low intensity region and a high intensity region is clear. In addition, for example, in an averaged image, random noise that is generated at each round of imaging can be reduced, and a region that was not rendered well in a source image at a certain time point can be subjected to interpolation using another source image group.

Note that, among the pair groups constituting the training data, pairs that do not contribute to improving image quality can be removed from the training data. For example, if the image quality of a high quality image that is ground truth included in one pair of the training data is not suitable for image diagnosis, there is a possibility that an image output by a learned model that learned using the relevant training data will have image quality that is not suitable for image diagnosis. Therefore, by removing pairs for which the image quality of the ground truth is not suitable for image diagnosis from the training data, the possibility of the learned model generating an image with image quality that is not suitable for image diagnosis can be reduced.

Further, in a case where the average intensity or an intensity distribution differs greatly in an image group which is a pair, there is a possibility that a learned model that learned using the relevant training data will output an image which is not suitable for image diagnosis and which has an intensity distribution that greatly differs from the intensity distribution of the low quality image. Therefore, a pair of input data and ground truth in which the average intensity or an intensity distribution differs greatly can be removed from the training data.

In addition, in a case where the structure or position of an imaging target to be rendered differs greatly in an image group which is a pair, there is a possibility that a learned model that learned using the relevant training data will output an image which is not suitable for image diagnosis and in which the imaging target is rendered with a structure or at a position that greatly differs from the low quality image. Therefore, a pair of input data and ground truth in which the structure or position of the imaging target to be rendered differs greatly between the input data and ground truth can also be removed from the training data.

By using the learned model that has performed learning in this way, in a case where an OCTA image obtained by one round of imaging (examination) is input, the image quality improving unit 224 can generate a high quality OCTA image for which the contrast was increased or noise was reduced or the like by averaging processing. Therefore, the image quality improving unit 224 can generate a high quality image that is suitable for image diagnosis based on a low quality image that is an input image.

Next, images used when performing learning will be described. An image group constituting a pair group composed of an OCTA image 301 and a high quality OCTA image 302 constituting training data is created using rectangular region images of a certain image size whose positional relationships correspond. The manner in which the images in question are created will now be described referring to FIG. 3A and FIG. 3B.

First, a case is described in which one pair group constituting the training data is taken as being composed of the OCTA image 301 and the high quality OCTA image 302. In this case, as illustrated in FIG. 3A, a pair is formed in which the entire OCTA image 301 is taken as input data, and the entire high quality OCTA image 302 is taken as ground truth. Note that, although in the example illustrated in FIG. 3A a pair composed of input data and ground truth is formed by using each image in its entirety, a pair is not limited thereto.

For example, as illustrated in FIG. 3B, a pair may be formed in which a rectangular region image 311 in the OCTA image 301 is adopted as input data, and a rectangular region image 321 that is a corresponding imaged region in the OCTA image 302 is adopted as ground truth.

Note that, when performing learning, the scanning range (imaging angle of view) and scanning density (number of A-scans and number of B-scans) can be normalized to make the image sizes uniform, so that the rectangular region sizes when performing learning can be made uniform. Further, the rectangular region images illustrated in FIG. 3A and FIG. 3B are examples of rectangular region sizes when the respective rectangular region sizes are used for performing learning separately from each other.

Further, the number of rectangular regions can be set to one in the example illustrated in FIG. 3A, and can be set to a plurality of rectangular regions in the example illustrated in FIG. 3B. For example, in the example illustrated in FIG. 3B, a pair can also be constituted in which a rectangular region image 312 in the OCTA image 301 is adopted as input data and a rectangular region image 322 that is a corresponding imaged region in the high quality OCTA image 302 is adopted as ground truth. Thus, pairs of rectangular region images which are different to each other can be created from a pair composed of one OCTA image and one high quality OCTA image. Note that, the content of pair groups constituting the training data can be enhanced by creating a large number of pairs of rectangular region images while changing the positions of the regions to different coordinates in the OCTA image and the high quality OCTA image that are the source images.

Although the rectangular regions are illustrated discretely in the example illustrated in FIG. 3B, the OCTA image and the high quality OCTA image that are the source images can each be divided into a group of rectangular region images of a uniform image size continuously and without gaps. Alternatively, the OCTA image and the high quality OCTA image that are the source images may each be divided into a rectangular region image group at random positions which correspond to each other. In this way, by selecting images of smaller regions as a pair composed of input data and ground truth as the rectangular regions, a large amount of pair data can be generated from the OCTA image 301 and the high quality OCTA image 302 constituting the original pair. Consequently, the time required for training the machine learning model can be shortened.

Next, as one example of a learned model according to the present embodiment, a convolutional neural network (CNN) that performs image quality improving processing with respect to an input tomographic image is described referring to FIG. 4. FIG. 4 illustrates an example of a configuration 401 of a learned model which the image quality improving unit 224 uses.

The learned model illustrated in FIG. 4 is constituted by a plurality of layer groups that are responsible for processing to process an input value group for output. Note that, the types of layers included in the configuration 401 of the learned model are a convolutional layer, a downsampling layer, an upsampling layer, and a merging layer.

The convolutional layer is a layer that performs convolutional processing with respect to an input value group according to parameters such as the kernel size of the filters, the number of filters, the value of a stride, and the dilation value which are set. Note that, the number of dimensions of the kernel size of the filter may be changed according to the number of dimensions of an input image.

The downsampling layer is a layer that performs processing for making the number of output value groups less than the number of input value groups by thinning out or combining the input value groups. Specifically, for example, max pooling processing is available as such processing.

The upsampling layer is a layer that performs processing for making the number of output value groups greater than the number of input value groups by duplicating an input value group or adding a value interpolated from an input value group. Specifically, for example, linear interpolation processing is available as such processing.

The merging layer is a layer that performs processing that inputs, from a plurality of sources, value groups such as an output value group of a certain layer or a pixel value group constituting an image, and merges the value groups by concatenating or adding the value groups.

Note that, as parameters that are set for convolutional layer groups included in the configuration 401 illustrated in FIG. 4, it is possible to perform image quality improving processing of a certain accuracy by, for example, setting the kernel size of the filters to a width of three pixels and a height of three pixels, and the number of filters to 64. However, it is necessary to pay attention in this regard because if the settings of parameters with respect to layer groups and node groups constituting a neural network differ, in some cases the degrees to which a tendency trained based on training data is reproducible in the output data will differ. In other words, in many cases, the appropriate parameters will differ according to the form at the time of implementation, and therefore parameters can be changed to preferable values as needed.

Further, there are also cases where the CNN can obtain better characteristics by changing the configuration of the CNN, and not just by using a method that changes parameters as described above. The term "better characteristics" refers to, for example, the accuracy of image quality improving processing increasing, the time taken for image quality improving processing becoming shorter, and the time required for training of the machine learning model becoming shorter.

Although not illustrated in the drawings, as a modification of the configuration of the CNN, for example, a batch normalization layer or an activation layer that uses a rectifier linear unit (ReLu) may be incorporated after the convolutional layer or the like.

When data is input to a learned model of a machine learning model of this kind, data in accordance with the design of the machine learning model is output. For example, output data is output that has a high probability of corresponding to the input data in accordance with a tendency for which the machine learning model was trained using training data. In the case of the learned model according to the present embodiment, when the OCTA image 301 is input, the high quality OCTA image 302 is output in accordance with a tendency for which the machine learning model was trained using training data.

Note that, in a case where learning is performed in a manner in which images are divided into regions, the learned model outputs rectangular region images that are high quality OCTA images corresponding to the respective rectangular regions. In this case, first, the image quality improving unit 224 divides the OCTA image 301 that is the input image into a rectangular region image group based on the image size when performing learning, and inputs the group of divided rectangular region images into the learned model. Thereafter, the image quality improving unit 224 arranges the respective images of a group of rectangular region images that are high quality OCTA images output from the learned model, according to the same positional relationship as that of the respective images of the rectangular region image group that was input to the learned model, and combines the rectangular region images. By this means, the image quality improving unit 224 can generate a high quality OCTA image 302 corresponding to the input OCTA image 301.

Figure 5:
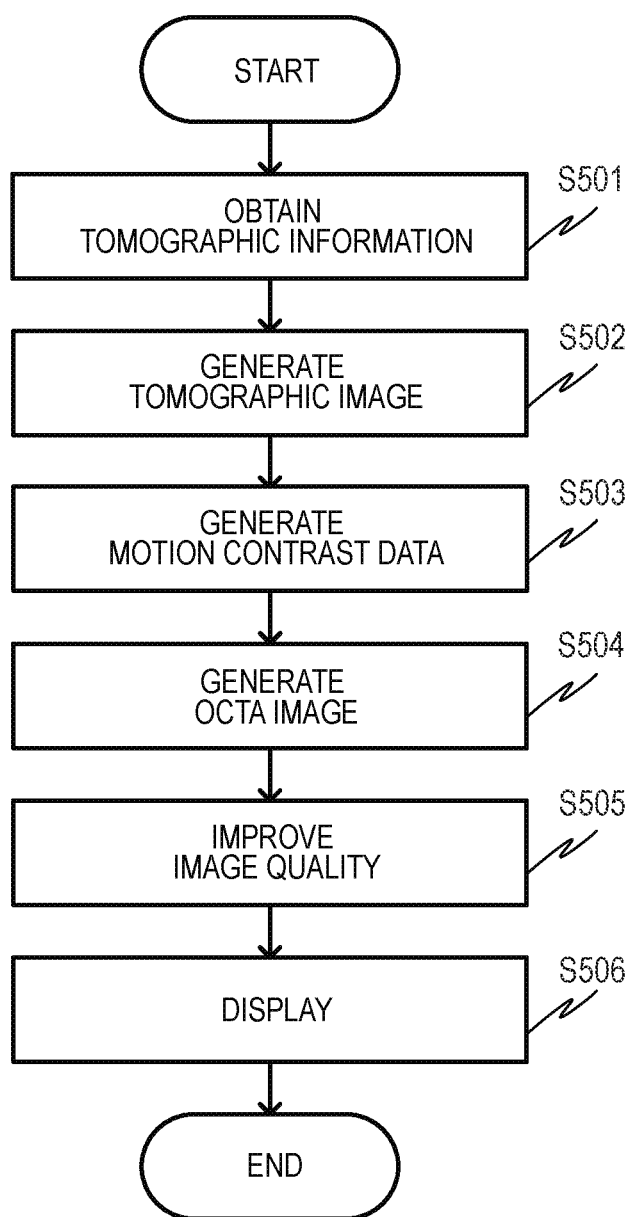
FIG. 5 is a flowchart of a series of image processing operations according to Embodiment 1.

Next, a series of image processing operations according to the present embodiment will be described referring to FIG. 5 to FIG. 7. FIG. 5 is a flowchart illustrating the series of image processing operations according to the present embodiment.

First, in step S501, the obtaining unit 210 obtains a plurality of items of three-dimensional tomographic information obtained by imaging the eye to be examined E a plurality of times. The obtaining unit 210 may obtain the tomographic information of the eye to be examined E using the OCT imaging unit 100, or may obtain the tomographic information from the storage 240 or another apparatus that is connected to the controlling unit 200.

Here, a case where tomographic information of the eye to be examined E is obtained by using the OCT imaging unit 100 will be described. First, the operator has the patient who is the subject sit down in front of the scanning optical system 150, performs alignment, inputs patient information into the controlling unit 200 or the like, and thereafter starts the OCT imaging. The drive controlling unit 230 of the controlling unit 200 drives the galvanometer mirror of the scanning unit 152 to scan approximately the same location of the eye to be examined a plurality of times and thereby obtains a plurality of items of tomographic information (interference signals) at approximately the same location of the eye to be examined. Thereafter, the drive controlling unit 230 slightly drives the galvanometer mirror of the scanning unit 152 in the sub-scanning direction orthogonal to the main scanning direction, and obtains a plurality of items of tomographic information at another location (adjacent scanning line) of the eye to be examined E. By repeating this control, the obtaining unit 210 obtains a plurality of items of three-dimensional tomographic information in a predetermined range of the eye to be examined E.

Next, in step S502, the tomographic image generating unit 221 generates a plurality of three-dimensional tomographic images based on the obtained plurality of items of three-dimensional tomographic information. Note that, in a case where, in step S501, the obtaining unit 210 obtains a plurality of three-dimensional tomographic images from the storage 240 or another apparatus that is connected to the controlling unit 200, step S502 can be omitted.

In step S503, the motion contrast generating unit 222 generates three-dimensional motion contrast data (a three-dimensional motion contrast image) based on the plurality of three-dimensional tomographic images. Note that, the motion contrast generating unit 222 may obtain a plurality of items of motion contrast data based on three or more tomographic images acquired with respect to approximately the same location, and generate an average value of the plurality of items of motion contrast data as final motion contrast data. Note that, in a case where, in step S501, the obtaining unit 210 obtains three-dimensional motion contrast data from the storage 240 or another apparatus that is connected to the controlling unit 200, step S502 and step S503 can be omitted.

In step S504, with respect to the three-dimensional motion contrast data, the en-face image generating unit 223 generates an OCTA image according to an instruction from the operator or based on a predetermined en-face image generation range. Note that, in a case where, in step S501, the obtaining unit 210 obtains an OCTA image from the storage 240 or another apparatus that is connected to the controlling unit 200, step S502 to step S504 can be omitted.

In step S505, the image quality improving unit 224 performs image quality improving processing on the OCTA image using the learned model. The image quality improving unit 224 inputs the OCTA image into the learned model, and generates a high quality OCTA image based on the output from the learned model. Note that, in a case where the learned model has performed learning in a manner in which images are divided into regions, the image quality improving unit 224 first divides the OCTA image that is the input image into a rectangular region image group based on the image size at the time of learning, and inputs the group of divided rectangular region images into the learned model. Thereafter, the image quality improving unit 224 arranges the respective images of a group of rectangular region images that are high quality OCTA images output from the learned model, according to the same positional relationship as that of the respective images of the rectangular region image group that was input to the learned model, and combines the rectangular region images to thereby generate a final high quality OCTA image.

In step S506, the display controlling unit 250 causes the display unit 270 to switch from displaying the original OCTA image (first medical image) to displaying the high quality OCTA image (second medical image) generated by the image quality improving unit 224. As described above, in image quality improving processing that uses a machine learning model, in some cases a blood vessel that does not actually exist is visualized in an OCTA image or a blood vessel that originally exists is not visualized in the OCTA image. In this regard, by the display controlling unit 250 causing the display unit 270 to switch from displaying the original OCTA image to displaying the generated high quality OCTA image, a determination as to whether a blood vessel is a blood vessel that was newly generated by image quality improving processing or is a blood vessel that also existed in the original image can be facilitated. When the display processing by the display controlling unit 250 ends, the series of image processing operations ends.

Figure 6A:
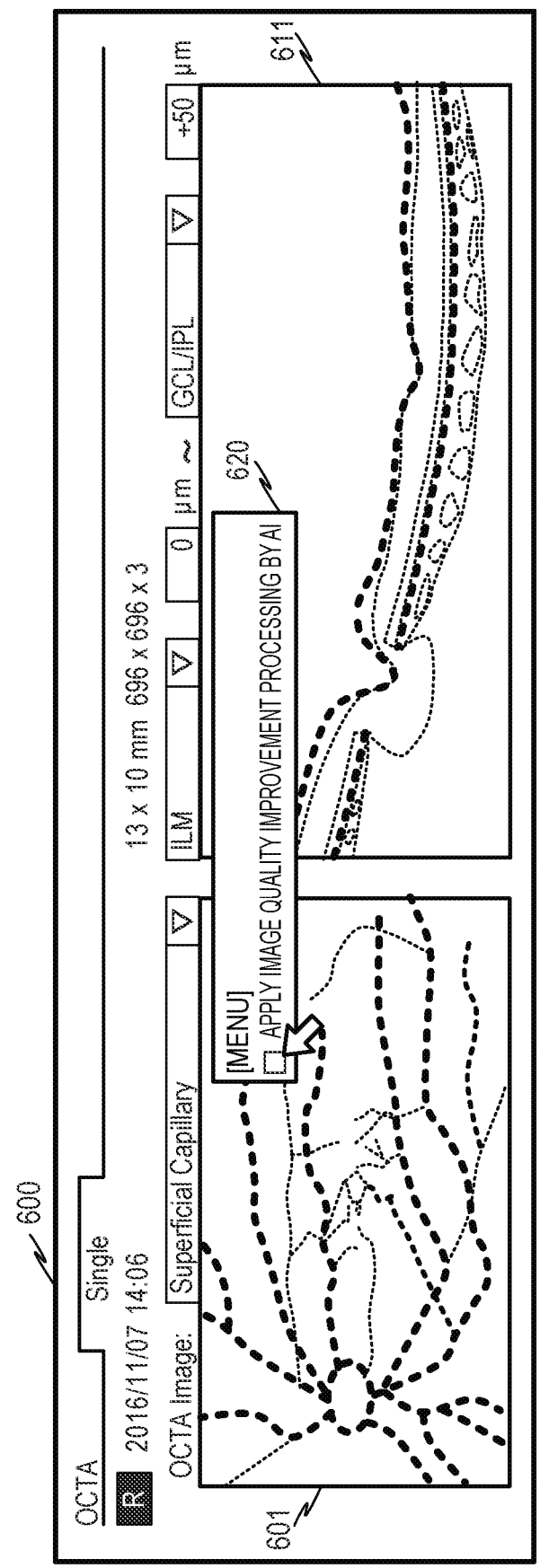
FIG. 6A is a view illustrating an example of a report screen that switches between and displays images obtained before and after image quality improving processing.
Figure 6B:
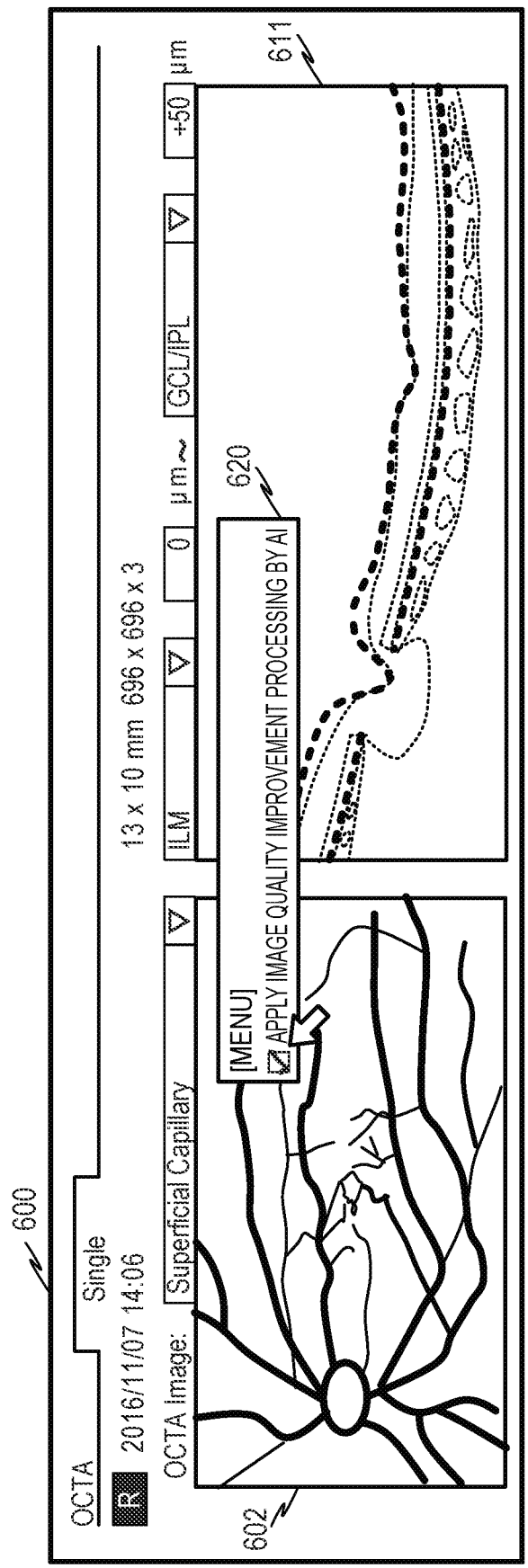
FIG. 6B is a view illustrating an example of a report screen that switches between and displays images obtained before and after image quality improving processing.
Figure 7:
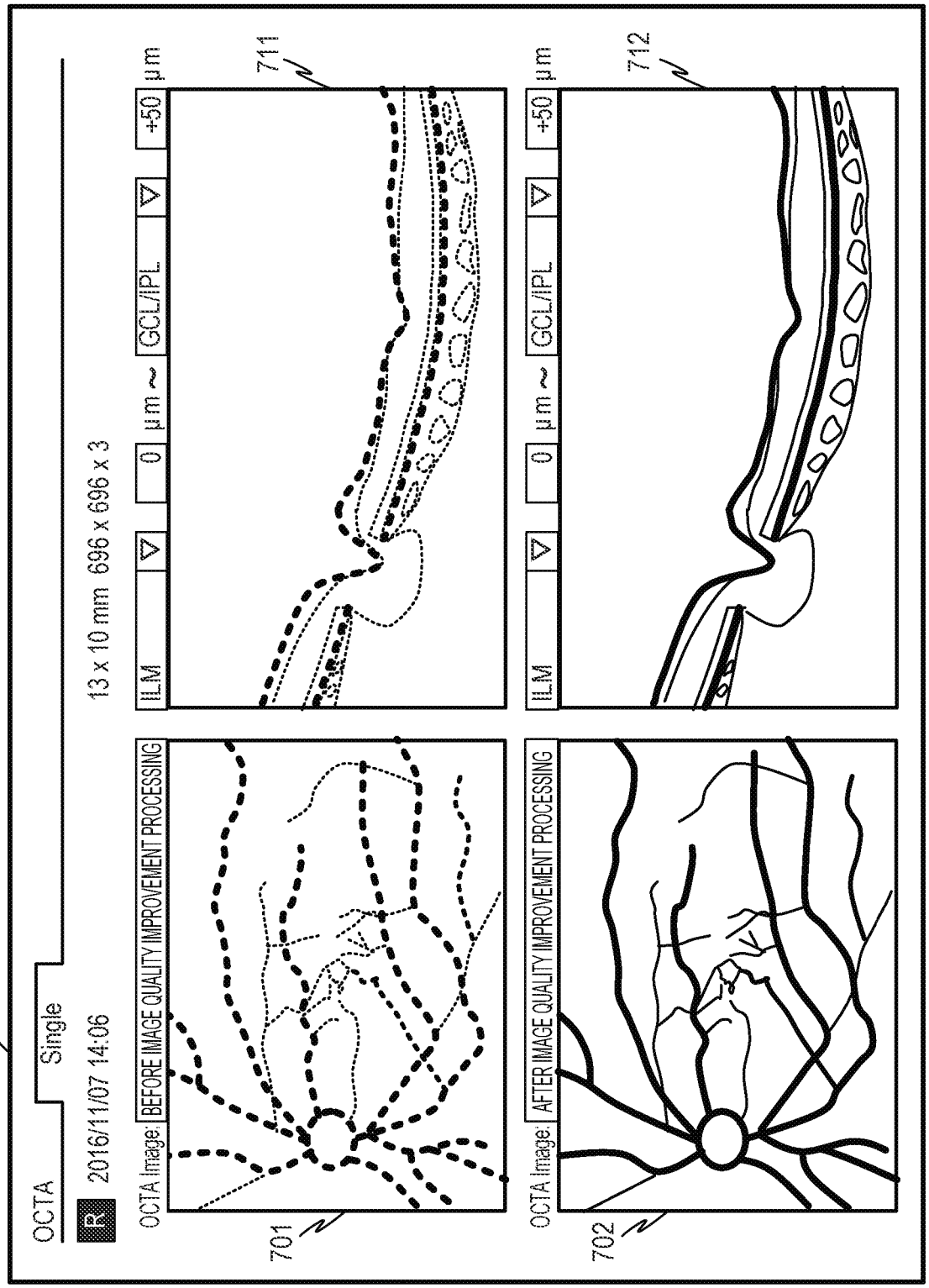
FIG. 7 is a view illustrating an example of a report screen on which images obtained before and after image quality improving processing are juxtaposed and displayed.

Next, the method for operating the controlling unit 200 is described referring to FIG. 6A to FIG. 7. FIG. 6A and FIG. 6B illustrate an example of a report screen that switches between and displays images before and after image quality improving processing. A tomographic image 611 and an OCTA image 601 before image quality improving processing are illustrated on a report screen 600 illustrated in FIG. 6A. The tomographic image 611 and an OCTA image 602 (high quality OCTA image) after image quality improving processing are illustrated on the report screen 600 illustrated in FIG. 6B.

On the report screen 600 illustrated in FIG. 6A, when the operator uses the mouse as one example of the inputting unit 260 and presses the right button of the mouse over the OCTA image 601, a pop-up menu 620 for selecting whether or not to perform image quality improving processing is displayed. When the operator selects to perform image quality improving processing on the pop-up menu 620, the image quality improving unit 224 executes image quality improving processing with respect to the OCTA image 601.

As illustrated in FIG. 6B, the display controlling unit 250 then causes the display on the report screen 600 to switch from displaying the OCTA image 601 before performing image quality improving processing to displaying the OCTA image 602 after performing the image quality improving processing. Note that, it is also possible to open the pop-up menu 620 by pressing the right button of the mouse over the OCTA image 602 once again, and to cause the display to switch to displaying the OCTA image 601 before performing the image quality improving processing.

Note that, although an example has been described in which switching between displaying images before and after image quality improving processing is performed by using the pop-up menu 620 that is displayed according to an operation in which the operator presses the right button of the mouse, apart from a pop-up menu, any other method may also be performed as a method for switching images. For example, switching of images may also be performed using a button provided on the report screen (an example of an image quality improving button), a pull-down menu, a radio button, a check box or a keyboard operation. In addition, switching of a displayed image may be performed by operation of a mouse wheel or a touch operation on a touch panel display.

The operator can arbitrarily switch between displaying the OCTA image 601 before performing the image quality improving processing and the OCTA image 602 after performing the image quality improving processing by the above method. Therefore, the operator can easily view and compare the OCTA images before and after the image quality improving processing, and can easily confirm a change between the OCTA images that was caused by the image quality improving processing. Accordingly, the operator can easily identify a blood vessel that does not actually exist which was visualized in the OCTA image by the image quality improving processing or that a blood vessel which originally existed has disappeared from the OCTA image due to the image quality improving processing, and can easily determine the authenticity of tissue visualized in the images.

Note that, although in the aforementioned display method the images before and after image quality improving processing are switched and displayed, a similar effect can be obtained by displaying these images in a juxtaposed or superimposed manner. FIG. 7 illustrates an example of a report screen in a case where images before and after image quality improving processing are displayed in a juxtaposed manner. On a report screen 700 illustrated in FIG. 7, an OCTA image 701 before image quality improving processing and an OCTA image 702 after image quality improving processing are displayed in a juxtaposed manner.

In this case also, the operator can easily view and compare the images before and after image quality improving processing, and can easily confirm a change between the images that was caused by the image quality improving processing. Therefore, the operator can easily identify a blood vessel that does not actually exist which was visualized in the OCTA image by the image quality improving processing or that a blood vessel which originally existed has disappeared from the OCTA image due to the image quality improving processing, and can easily determine the authenticity of tissue visualized in the images. Note that, in the case of displaying the images before and after image quality improving processing in a superimposed manner, the display controlling unit 250 can set a degree of transparency with respect to at least one image among the images before and after image quality improving processing, and cause the images before and after image quality improving processing to be displayed in a superimposed manner on the display unit 270.

Further, as described above, the image quality improving unit 224 may also perform image quality improving processing using a learned model on a tomographic image or an intensity en-face image, and not just an OCTA image. In such case, as a pair of the training data of the learned model, a pair can be used in which a tomographic image or intensity en-face image before averaging is adopted as input data, and a tomographic image or intensity en-face image after averaging is adopted as ground truth. Note that, in this case, the learned model may be a single learned model which performed learning using training data such as an OCTA image or a tomographic image, or a plurality of learned models which performed learning for respective kinds of images may be used as learned models. In a case where a plurality of learned models are used, the image quality improving unit 224 can use a learned model corresponding to the kind of image that is the object to perform the image quality improving processing. Note that, the image quality improving unit 224 may perform image quality improving processing using a learned model with respect to a three-dimensional motion contrast image or a three-dimensional tomographic image, and the training data in this case can also be prepared in the same manner as described above.

In FIG. 7, a tomographic image 711 before image quality improving processing and a tomographic image 712 after image quality improving processing are displayed in a juxtaposed manner. Note that, the display controlling unit 250 may cause the tomographic images or intensity en-face images before and after image quality improving processing to be switched and displayed on the display unit 270, similarly to the OCTA images before and after image quality improving processing that are illustrated in FIG. 6A and FIG. 6B. Further, the display controlling unit 250 may cause the tomographic images or intensity en-face images before and after image quality improving processing to be displayed in a superimposed manner on the display unit 270. In these cases also, the operator can easily view and compare the images before and after the image quality improving processing, and can easily confirm a change between the images caused by the image quality improving processing. Therefore, the operator can easily identify tissue that does not actually exist which was visualized in the image by the image quality improving processing or that tissue which originally existed has disappeared from the image due to the image quality improving processing, and can easily determine the authenticity of tissue visualized in the images.

As described above, the controlling unit 200 according to the present embodiment includes the image quality improving unit 224 and the display controlling unit 250. The image quality improving unit 224 generates, from a first medical image of an eye to be examined, a second medical image subjected to at least one of noise reduction and contrast enhancement compared to the first medical image, using a learned model. The display controlling unit 250 causes the first medical image and the second medical image to be switched, juxtaposed or superimposed and displayed on the display unit 270. Note that, the display controlling unit 250 can switch between the first medical image and the second medical image and display the relevant switched image on the display unit 270 according to an instruction from the operator.

By this means, the controlling unit 200 can generate a high quality image in which noise is reduced and/or contrast is enhanced from a source image. Therefore, the controlling unit 200 can generate an image that is more suitable for image diagnosis in comparison to the conventional technology, such as a clearer image or an image in which a site or lesion that it is desired to observe is enhanced.

Further, the operator can easily view and compare the images before and after the image quality improving processing, and can easily confirm a change between the images caused by the image quality improving processing. Therefore, the operator can easily identify tissue that does not actually exist which was visualized in the image by the image quality improving processing or that tissue which originally existed has disappeared from the image due to the image quality improving processing, and can easily determine the authenticity of tissue visualized in the images.

Although an averaged image is used as the ground truth of the training data for the learned model according to the present embodiment, the training data is not limited thereto. For example, a high quality image obtained by performing maximum a posteriori processing (MAP estimation processing) with respect to a source image group may be used as ground truth of the training data. In MAP estimation processing, a likelihood function is obtained based on the probability density of each pixel value in a plurality of images, and a true signal value (pixel value) is estimated using the obtained likelihood function.

A high quality image obtained by MAP estimation processing is a high contrast image that is based on pixel values that are close to the true signal values. Further, since the estimated signal values are determined based on the probability density, randomly generated noise is reduced in a high quality image obtained by MAP estimation processing. Therefore, by using a high quality image obtained by MAP estimation processing as training data, the learned model can generate, from an input image, a high quality image that is suitable for image diagnosis in which noise is reduced and which has high contrast. Note that, with regard to the method for generating a pair of input data and ground truth of the training data, a method that is similar to a case where an averaged image is used as training data may be performed.

Further, as ground truth of the training data, a high quality image obtained by applying smoothing filter processing to a source image may be used. In this case, the learned model can generate a high quality image in which random noise is reduced from an input image. In addition, an image obtained by applying gradation conversion processing to a source image may also be used as ground truth of the training data. In this case, the learned model can generate a high quality image with enhanced contrast from an input image. Note that, with regard to the method for generating a pair of input data and ground truth of the training data, a method that is similar to a case where an averaged image is used as training data may be performed.

Note that, the input data of the training data may be an image obtained from an imaging apparatus having the same image quality tendency as the OCT imaging unit 100. Further, the ground truth of the training data may be a high quality image obtained by high-cost processing such as processing using the method of successive approximation, or may be a high quality image obtained by imaging an object under examination corresponding to the input data using an imaging apparatus with higher performance than the OCT imaging unit 100. In addition, the ground truth may be a high quality image obtained by performing rule-based noise reduction processing that is based on the structure of the object under examination or the like. Here, the noise reduction processing can include, for example, processing that replaces a high intensity pixel that is only one pixel which is clearly noise that appears in a low intensity region with the average value of neighboring low-intensity pixel values. Thus, as training data, the learned model may adopt an image imaged by an imaging apparatus with higher performance than the imaging apparatus used to image an input image, or an image obtained by an imaging process that involves a greater number of processes than the imaging process used to obtain the input image.

Note that, although it has been described that the image quality improving unit 224 generates a high quality image in which noise is reduced or contrast is enhanced by using a learned model, image quality improving processing by the image quality improving unit 224 is not limited thereto. It suffices that, as described above, the image quality improving unit 224 can generate an image with image quality that is more suitable for image diagnosis by image quality improving processing.

Further, in the case of causing images before and after image quality improving processing to be displayed in a juxtaposed manner on the display unit 270, in accordance with an instruction from the operator, the display controlling unit 250 may enlarge and display any of the images among the images before and after image quality improving processing that are being displayed in a juxtaposed manner on the display unit 270. More specifically, for example, on the report screen 700 illustrated in FIG. 7, if the operator selects the OCTA image 701, the display controlling unit 250 can enlarge and display the OCTA image 701 on the report screen 700. Further, if the operator selects the OCTA image 702 after image quality improving processing, the display controlling unit 250 can enlarge and display the OCTA image 702 on the report screen 700. In this case, an image that the operator wishes to observe among the images before and after image quality improving processing can be observed in more detail by the operator.

In addition, in a case where the generation range of an en-face image such as an OCTA image is changed according to an instruction of the operator, the controlling unit 200 may change the display from the images that are being displayed in a juxtaposed manner to an image that is based on the changed generation range and an image that was subjected to image quality improving. More specifically, when the operator changes the en-face image generation range through the inputting unit 260, the en-face image generating unit 223 generates an en-face image before image quality improving processing based on the changed generation range. The image quality improving unit 224 generates a high quality en-face image from the en-face image that was newly generated by the en-face image generating unit 223, using a learned model. Thereafter, the display controlling unit 250 causes the display unit 270 to change from displaying the en-face images before and after image quality improving processing that are being displayed in a juxtaposed manner to displaying the newly generated en-face images before and after image quality improving processing. In such a case, while the operator arbitrarily changes the range in the depth direction that the operator desires to observe, the operator can observe en-face images before and after image quality improving processing based on the changed range in the depth direction.

(Modification 1)

As described above, in an image on which image quality improving processing was performed using a learned model, tissue that does not actually exist may be visualized, or tissue that originally exists may not be visualized. Therefore, a misdiagnosis may occur due to an operator performing an image diagnosis based on such an image. Therefore, when displaying an OCTA image or tomographic image or the like after image quality improving processing on the display unit 270, the display controlling unit 250 may also display information to the effect that the image in question is an image on which image quality improving processing was performed using a learned model. In this case, the occurrence of a misdiagnosis by the operator can be suppressed. Note that, the display form may be any form as long as the form is such that it can be understood that the image is a high quality image obtained using a learned model.

(Modification 2)

In Embodiment 1, an example was described in which image quality improving processing is applied to an OCTA image or a tomographic image or the like obtained by one round of imaging (examination). In this regard, image quality improving processing using a learned model can also be applied to a plurality of OCTA images or tomographic images or the like obtained by performing imaging (examination) a plurality of times. In Modification 2, a configuration in which images obtained by applying image quality improving processing using a learned model to a plurality of OCTA images or tomographic images or the like are displayed simultaneously is described referring to FIG. 8A and FIG. 8B.

Figure 8A:
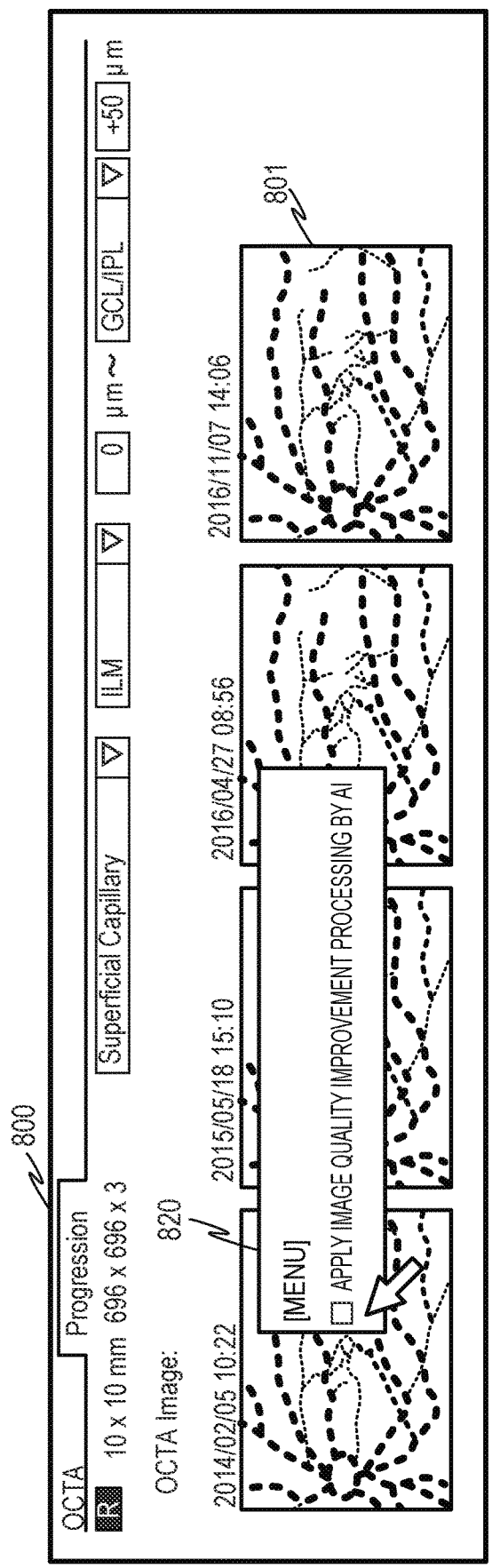
FIG. 8A is a view illustrating an example of a report screen on which a plurality of images before applying image quality improving processing are displayed simultaneously.
Figure 8B:
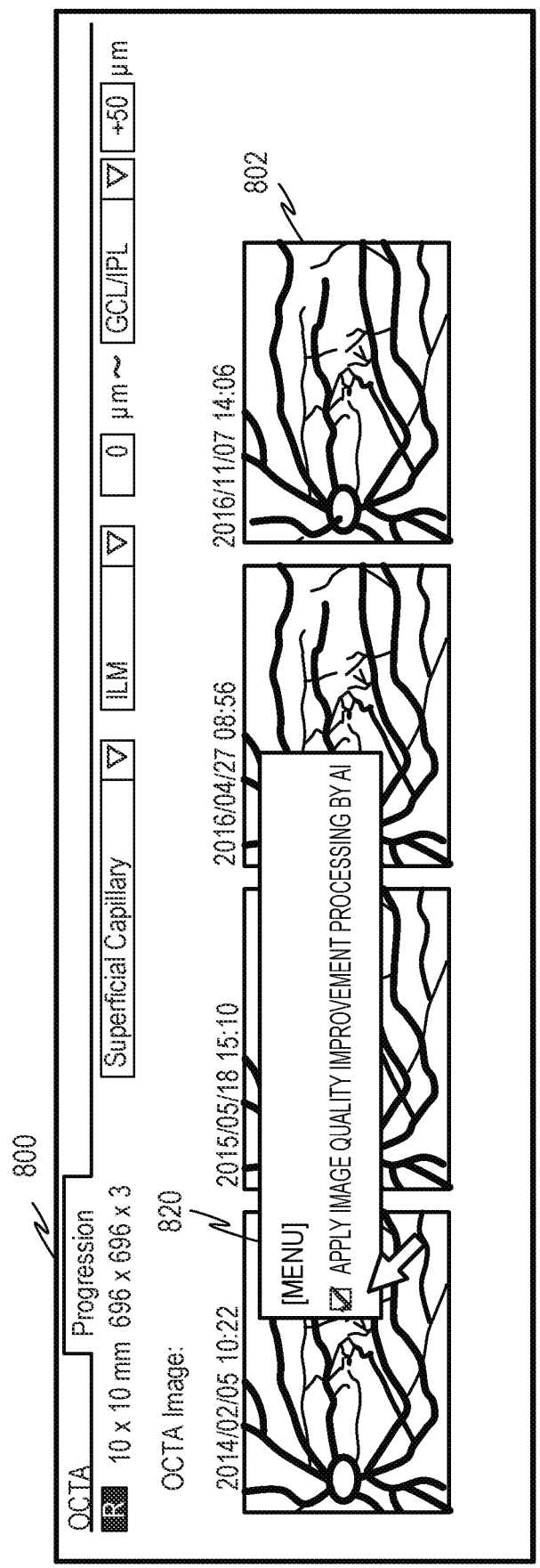
FIG. 8B is a view illustrating an example of a report screen on which a plurality of images to which image quality improving processing was applied are displayed simultaneously.

FIG. 8A and FIG. 8B each illustrate an example of a time-series report screen for displaying a plurality of OCTA images obtained by imaging the same eye to be examined a plurality of times over time. On a report screen 800 illustrates in FIG. 8A, a plurality of OCTA images 801 before performing image quality improving processing are displayed side by side in chronological order. The report screen 800 also includes a pop-up menu 820, and it is possible for the operator to select whether or not to apply image quality improving processing by operating the pop-up menu 820 through the inputting unit 260.

If the operator selects to apply image quality improving processing, the image quality improving unit 224 applies image quality improving processing using a learned model to all of the OCTA images that are being displayed. Subsequently, as illustrated in FIG. 8B, the display controlling unit 250 switches from displaying the plurality of OCTA images 801 that were being displayed to displaying a plurality of OCTA images 802 after performing image quality improving processing.

Further, if the operator selects not to apply image quality improving processing on the pop-up menu 820, the display controlling unit 250 switches from displaying the plurality of OCTA images 802 after image quality improving processing that were being displayed to displaying the plurality of OCTA images 801 before image quality improving processing.

Note that, in the present modification an example has been described in which a plurality of OCTA images obtained before and after image quality improving processing using a learned model are simultaneously switched and displayed. However, a plurality of tomographic images or intensity en-face images or the like obtained before and after image quality improving processing using a learned model may be simultaneously switched and displayed. Note that, the operation method is not limited to a method that uses the pop-up menu 820, and any operation method may be adopted such as a method that uses a button (an example of an image quality improving button), a pull-down menu, a radio button or a check box provided on the report screen, or an operation with respect to a keyboard, a mouse wheel or a touch panel.

Embodiment 2

A learned model outputs output data that has a high probability of corresponding to the input data according to a learning tendency. In this regard, when the learned model performs learning using a group of images having a similar image quality tendency to each other as training data, an image that underwent image quality improving more effectively can be output with respect to an image that has the similar tendency in question. Therefore, in Embodiment 2, image quality improving processing is performed more effectively by performing the image quality improving processing by means of a plurality of learned models that underwent learning using training data constituted by pair groups that were grouped for each imaging condition such as the imaged site or for each en-face image generation range.

Figure 9:
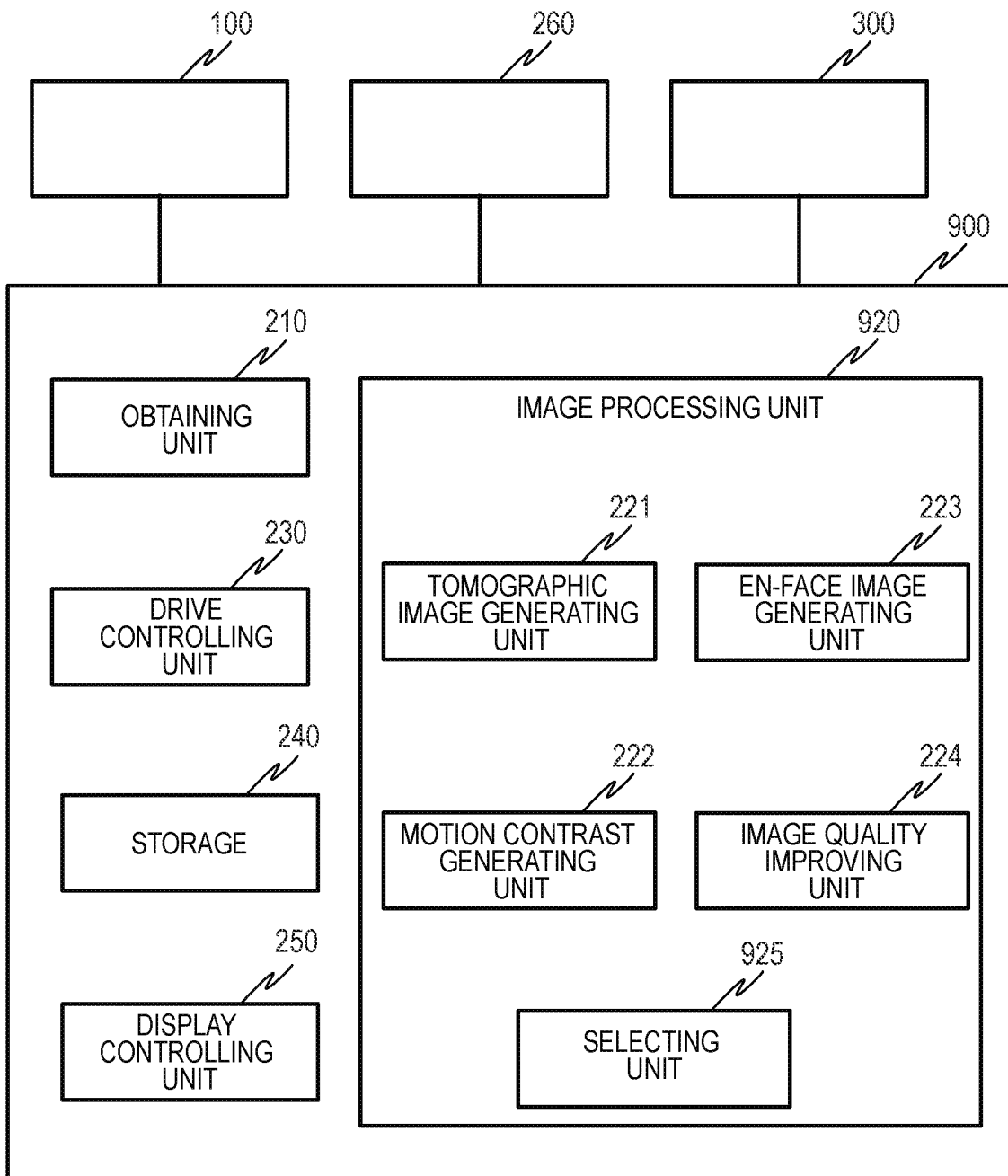
FIG. 9 is a view illustrating a schematic configuration of a controlling unit according to Embodiment 2.
Figure 10:
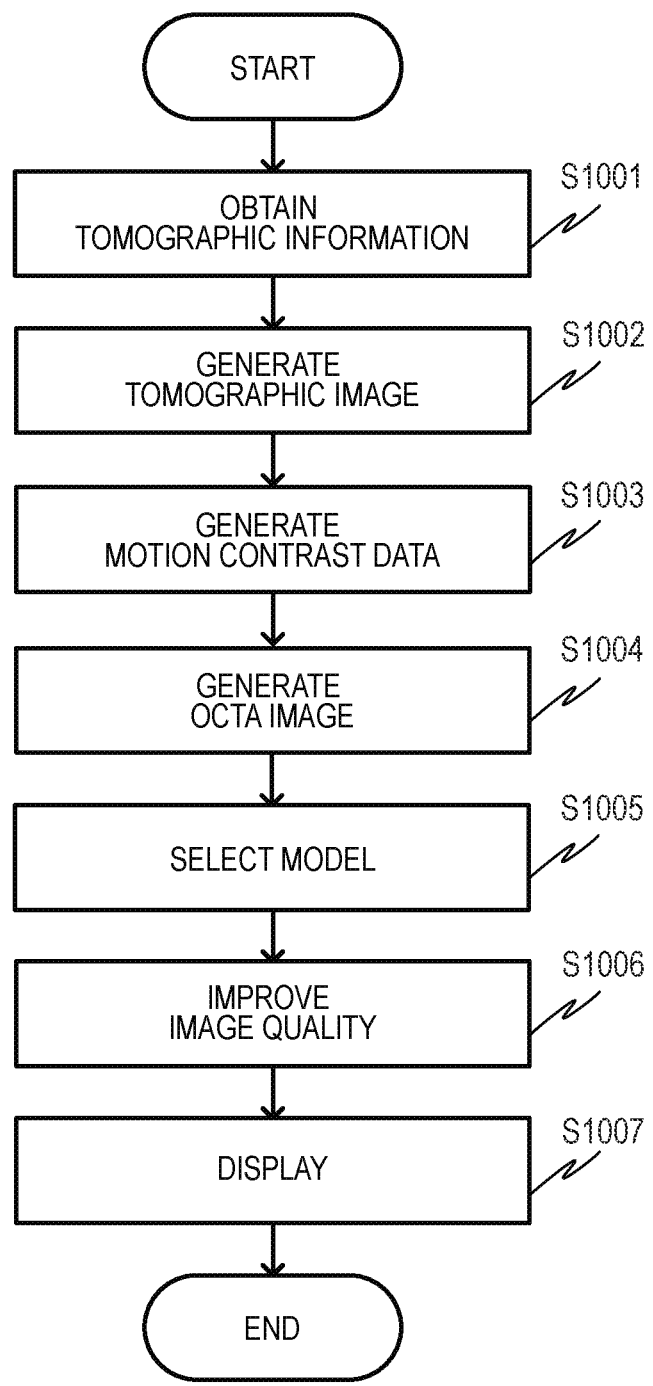
FIG. 10 is a flowchart of a series of image processing operations according to Embodiment 2.

Hereunder, an OCT apparatus according to the present embodiment is described referring to FIG. 9 and FIG. 10. Note that, since a configuration of the OCT apparatus according to the present embodiment is the same as the configuration of the OCT apparatus 1 according to Embodiment 1 with the exception of the controlling unit, components that are the same as components illustrated in FIG. 1 are denoted by the same reference numerals as those in Embodiment 1, and a description of the components is omitted hereunder. Hereunder, the OCT apparatus according to the present embodiment is described centering on differences from the OCT apparatus 1 according to Embodiment 1.

FIG. 9 illustrates a schematic configuration of a controlling unit 900 according to the present embodiment. Note that, apart from an image processing unit 920 and a selecting unit 925, the components of the controlling unit 900 according to the present embodiment are the same as the respective components of the controlling unit 200 according to Embodiment 1. Therefore, components that are the same as components illustrated in FIG. 2 are denoted by the same reference numerals as those in Embodiment 1, and a description of the components is omitted hereunder.

In addition to the tomographic image generating unit 221, the motion contrast generating unit 222, the en-face image generating unit 223 and the image quality improving unit 224, the selecting unit 925 is also provided in the image processing unit 920 of the controlling unit 900.

The selecting unit 925 selects a learned model to be used by the image quality improving unit 224 from among a plurality of learned models, based on an en-face image generation range or an imaging condition of an image on which image quality improving processing is to be performed by the image quality improving unit 224. The image quality improving unit 224 performs image quality improving processing on a target OCTA image or tomographic image or the like using the learned model selected by the selecting unit 925, and generates a high quality OCTA image or a high quality tomographic image.

Next, the plurality of learned models according to the present embodiment will be described. As mentioned above, a learned model outputs output data that has a high probability of corresponding to the input data in accordance with a learning tendency. In this regard, when the learned model performs learning using a group of images having a similar image quality tendency to each other as training data, an image that underwent image quality improving more effectively can be output with respect to an image that has the similar tendency in question. Therefore, in the present embodiment, a plurality of learned models are prepared that underwent learning using training data composed of pair groups that were grouped according to imaging conditions including conditions such as an imaged site, imaging system, imaged region, imaging angle of view, scanning density and image resolution or for each en-face image generation range.

More specifically, for example, a plurality of learned models such as a learned model for which OCTA images in which the macular area was set as the imaged site were adopted as training data, and a learned model for which OCTA images in which the optic nerve head was set as the imaged site were adopted as training data are prepared. Note that, the macular area and the optic nerve head are each one example of an imaged site, and other imaged sites may be included. Further, a learned model for which OCTA images for each specific imaged region of an imaged site such as the macular area or the optic nerve head were adopted as training data may be prepared.

Further, for example, visualization of structures such as a blood vessel that are visualized in an OCTA image differs significantly between a case where the retina is imaged with a wide angle of view and low density, and a case where the retina is imaged with a narrow angle of view and high density. Therefore, learned models that performed learning for each set of training data according to an imaging angle of view and a scanning density may be prepared. In addition, examples of imaging systems include an SD-OCT imaging system and an SS-OCT imaging system, and the image quality, the imaging range, and the penetration depth in the depth direction and the like differ according to the differences between these imaging systems. Therefore, learned models that performed learning using training data in accordance with respective kinds of imaging systems may be prepared.

Further, normally it is rare to generate an OCTA image in which blood vessels of all layers of the retina are extracted at once, and it is common to generate an OCTA image in which only blood vessels present in a predetermined depth range are extracted. For example, with respect to depth ranges such as a shallow layer, a deep layer and an outer layer of the retina, and a shallow choroidal layer, OCTA images are generated in which blood vessels are extracted in the respective depth ranges. On the other hand, the form of a blood vessel that is visualized in an OCTA image differs greatly depending on the depth range. For example, blood vessels visualized in a shallow layer of the retina form a low-density, thin and clear blood vessel network, while blood vessels visualized in a shallow choroidal layer are visualized with a high density and it is difficult to clearly distinguish individual blood vessels. Therefore, learned models that performed learning using respective sets of training data according to the generation ranges of an en-face image such as an OCTA image may be prepared.

Although an example in which an OCTA image is adopted as training data has been described here, similarly to Embodiment 1, in a case of performing image quality improving processing with respect to a tomographic image or an intensity en-face image or the like, these images can be adopted as training data. In such a case, a plurality of learned models that performed learning using respective sets of training data according to imaging conditions or en-face image generation ranges of these images are prepared.

Next, a series of image processing operations according to the present embodiment is described referring to FIG. 10. FIG. 10 is a flowchart illustrating a series of image processing operations according to the present embodiment. Note that, a description regarding processing that is the same as that in the series of image processing operations according to Embodiment 1 is omitted as appropriate.

First, in step S1001, similarly to step S501 according to Embodiment 1, the obtaining unit 210 obtains a plurality of items of three-dimensional tomographic information obtained by imaging the eye to be examined E a plurality of times. The obtaining unit 210 may obtain the tomographic information of the eye to be examined E using the OCT imaging unit 100, or may obtain the tomographic information from the storage 240 or another apparatus that is connected to the controlling unit 200.

The obtaining unit 210 also obtains an imaging conditions group relating to the tomographic information. Specifically, the obtaining unit 210 can obtain imaging conditions such as the imaged site and the imaging system when the imaging relating to the tomographic information was performed. Note that, depending on the data format of the tomographic information, the obtaining unit 210 may obtain an imaging conditions group stored in the data structure constituting the data of the tomographic information. Further, in a case where imaging conditions are not stored in the data structure of the tomographic information, the obtaining unit 210 can obtain an imaging information group from a server or database or the like that stores a file in which the imaging conditions are described. Further, the obtaining unit 210 may estimate an imaging information group from an image based on the tomographic information by any known method.

Further, in a case where the obtaining unit 210 obtains a plurality of three-dimensional tomographic images, a plurality of items of three-dimensional motion contrast data, or a plurality of OCTA images or the like, the obtaining unit 210 obtains an imaging conditions group relating to the obtained images or data. Note that, in the case of using only a plurality of learned models that performed learning using respective kinds of training data according to generation ranges of OCTA images or intensity en-face images for image quality improving processing, the obtaining unit 210 need not obtain an imaging conditions group of a tomographic image.

The processing from step S1002 to step S1004 is the same as the processing from step S502 to step S504 according to Embodiment 1, and hence a description of the processing is omitted here. Upon the en-face image generating unit 223 generating an OCTA image in step S1004, the processing shifts to step S1005.

In step S1005, the selecting unit 925 selects a learned model to be used by the image quality improving unit 224, based on the imaging conditions group or generation range relating to the generated OCTA image and information pertaining to the training data relating to the plurality of learned models. More specifically, for example, in a case where the imaged site in the OCTA image is the optic nerve head, the selecting unit 925 selects a learned model that performed learning using an OCTA image of the optic nerve head as training data. Further, for example, in a case where the generation range of the OCTA image is a shallow layer of the retina, the selecting unit 925 selects a learned model that performed learning using, as training data, an OCTA image for which a shallow layer of the retina was set as the generation range.

Note that, the selecting unit 925 may select a learned model that performed learning using, as training data, an image having a similar tendency with regard to the image quality, even if the imaging conditions group or generation range relating to the generated OCTA image and the information pertaining to the training data of the learned model do not completely match. In this case, for example, the selecting unit 925 may include a table in which the correlation between imaging condition groups or generation ranges relating to OCTA images and the learned models to be used is described.

In step S1006, the image quality improving unit 224 uses the learned model selected by the selecting unit 925 to perform image quality improving processing on the OCTA image generated in step S1004, to thereby generate a high quality OCTA image. The method for generating the high quality OCTA image is the same as in step S505 according to Embodiment 1, and hence a description thereof is omitted here.

Step S1007 is the same as step S506 according to Embodiment 1, and hence a description thereof is omitted here. When the high quality OCTA image is displayed on the display unit 270 in step S1007, the series of image processing operations according to the present embodiment ends.

As described above, the controlling unit 900 according to the present embodiment includes the selecting unit 925 that selects a learned model to be used by the image quality improving unit 224 from a plurality of learned models, the selecting unit 925 selects a learned model to be used by the image quality improving unit 224 based on a range in the depth direction for generating the OCTA image on which image quality improving processing is to be performed.

For example, the selecting unit 925 can select a learned model based on a display site in an OCTA image to be subjected to image quality improving processing and a range in the depth direction for generating the OCTA image. Further, for example, the selecting unit 925 may select a learned model to be used by the image quality improving unit 224 based on an imaged site including a display site in an OCTA image on which image quality improving processing is to be performed, and a range in the depth direction for generating the OCTA image. In addition, for example, the selecting unit 925 may select a learned model to be used by the image quality improving unit 224 based on an imaging condition of the OCTA image on which image quality improving processing is to be performed.

Therefore, the controlling unit 900 can perform image quality improving processing more effectively by performing the image quality improving processing by means of a plurality of learned models that underwent learning using training data constituted by pair groups that were grouped for each imaging condition or for each en-face image generation range.

Note that, although in the present embodiment an example is described in which the selecting unit 925 selects a learned model based on an imaging condition such as the imaged site or a generation range relating to an OCTA image, a configuration may be adopted so as to change a learned model based on a condition other than the aforementioned conditions. The selecting unit 925, for example, may select a learned model according to a projection method (maximum intensity projection method or average intensity projection method) when generating an OCTA image or an intensity en-face image, or whether or not artifact removal processing to remove an artifact caused by a blood vessel shadow has been performed. In this case, learned models that performed learning using respective kinds of training data according to projection methods and whether or not artifact removal processing has been performed can be prepared.

(Modification 3)

In Embodiment 2, the selecting unit 925 automatically selects an appropriate learned model according to an imaging condition or a generation range of an en-face image or the like. In this regard, there are also cases where the operator wishes to manually select image quality improving processing to be applied to an image. Therefore, the selecting unit 925 may select a learned model according to an instruction of the operator.

Further, there are also cases where the operator wishes to change the image quality improving processing applied to an image. Therefore, the selecting unit 925 may change the learned model to change the image quality improving processing to be applied to an image according to an instruction of the operator.

Figure 11A:
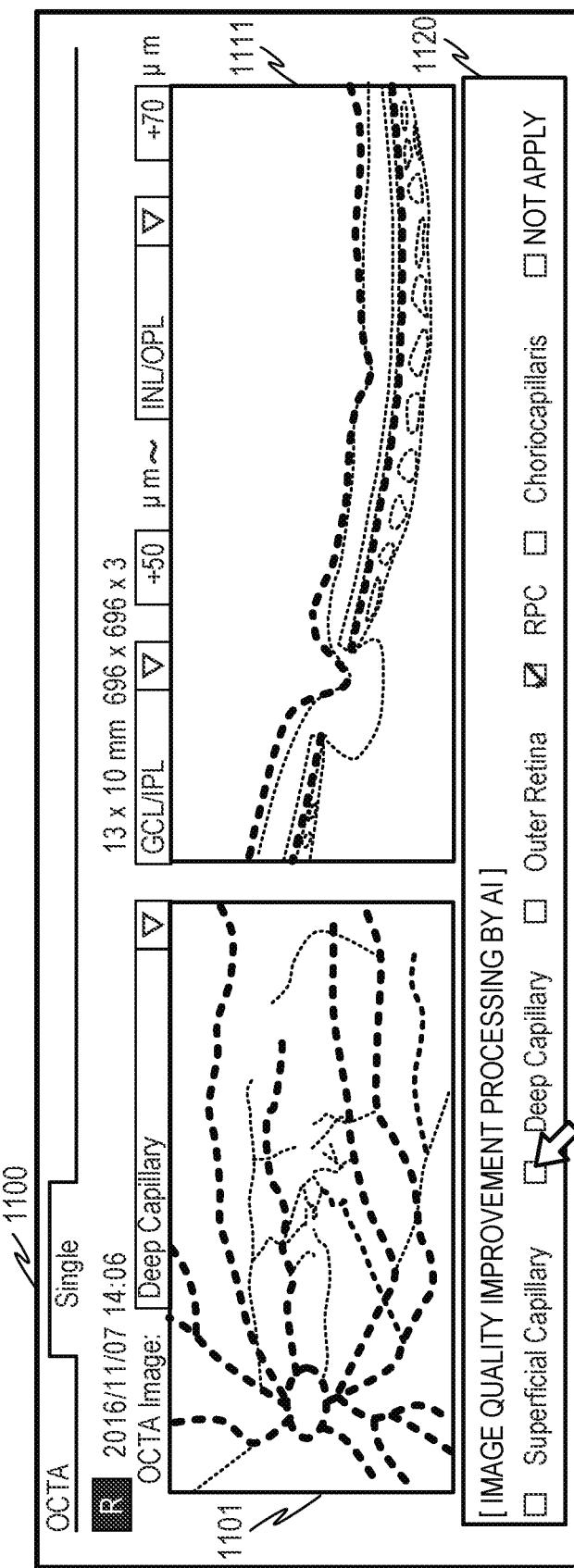
FIG. 11A is a view illustrating an example of changing image quality improving processing.
Figure 11B:
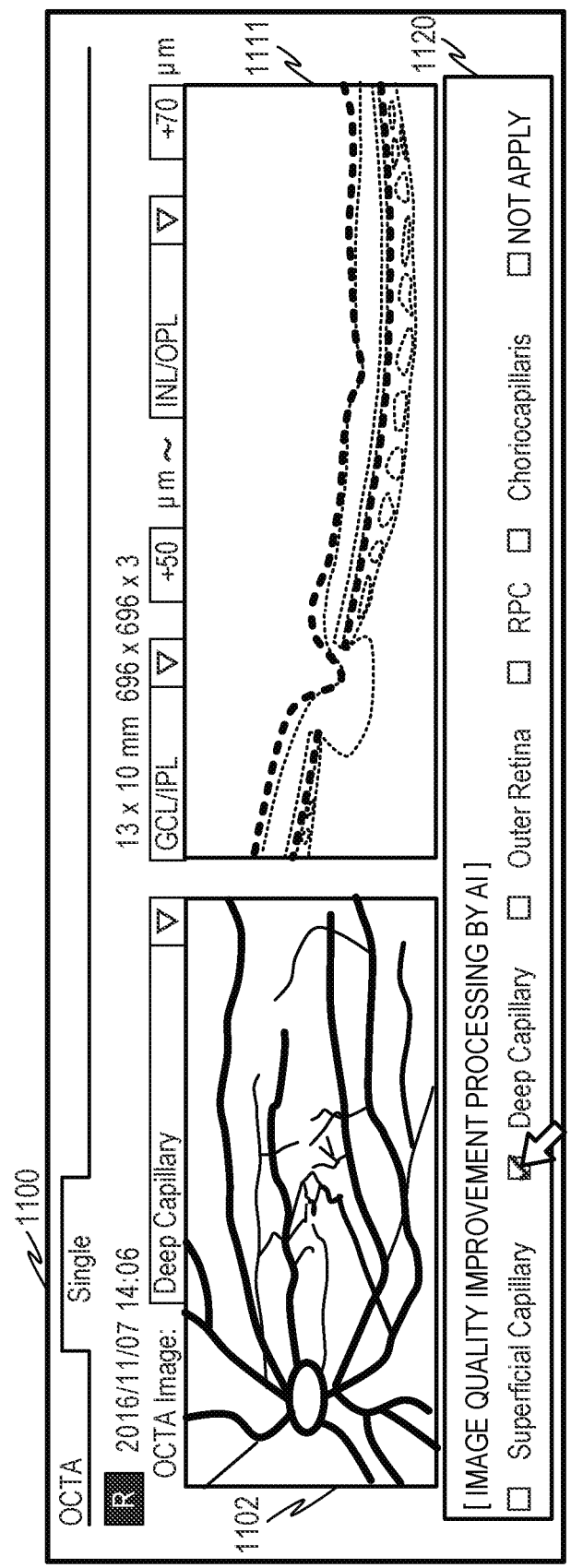
FIG. 11B is a view illustrating an example of changing image quality improving processing.

Hereunder, an operation method when manually changing the image quality improving processing to be applied to an image is described referring to FIG. 11A and FIG. 11B. FIG. 11A and FIG. 11B each illustrate an example of a report screen that switches between and displays images before and after image quality improving processing. On a report screen 1100 illustrated in FIG. 11A, a tomographic image 1111 and an OCTA image 1101 to which image quality improving processing using an automatically selected learned model has been applied are shown. On the report screen 1100 illustrated in FIG. 11B, the tomographic image 1111 and an OCTA image 1102 to which image quality improving processing using a learned model according to an instruction of the operator has been applied are shown. Further, on the report screen 1100 illustrated in FIG. 11A and FIG. 11B, a processing specifying section 1120 for changing the image quality improving processing applied to the OCTA image is shown.

The OCTA image 1101 displayed on the report screen 1100 illustrated in FIG. 11A is an OCTA image in which deep capillaries in the macular area are visualized. On the other hand, the image quality improving processing applied to the OCTA image using a learned model that was automatically selected by the selecting unit 925 is processing suitable for radial parapapillary capillaries (RPC). Therefore, with regard to the OCTA image 1101 displayed on the report screen 1100 illustrated in FIG. 11A, the image quality improving processing that has been applied to the OCTA image is not the optimal processing with respect to the blood vessels extracted in the OCTA image.

Therefore, the operator selects "Deep Capillary" in the processing specifying section 1120 through the inputting unit 260. In response to a selection instruction from the operator, the selecting unit 925 changes the learned model used by the image quality improving unit 224 to a learned model that performed learning using an OCTA image relating to deep capillaries of the macular area as training data.

The image quality improving unit 224 performs image quality improving processing on the OCTA image once more using the learned model which was changed to by the selecting unit 925. As illustrated in FIG. 11B, the display controlling unit 250 causes the high quality OCTA image 1102 which was newly generated by the image quality improving unit 224 to be displayed on the display unit 270.

Thus, by configuring the selecting unit 925 so as to change a learned model in response to an instruction of the operator, the operator can respecify appropriate image quality improving processing to be performed with respect to the same OCTA image. Further, specification of the image quality improving processing may be performed any number of times.

Here, an example has been illustrated in which the controlling unit 900 is configured so that the image quality improving processing to be applied to an OCTA image can be manually changed. In this regard, the controlling unit 900 may also be configured so that it is possible to manually change the image quality improving processing to be applied to a tomographic image or an intensity en-face image or the like.

Further, although the report screen illustrated in FIG. 11A and FIG. 11B is of a form which switches between and displays images before and after image quality improving processing, the report screen may be of a form which displays images before and after image quality improving processing in a juxtaposed manner or a superimposed manner. In addition, the form of the processing specifying section 1120 is not limited to the form illustrated in FIG. 11A and FIG. 11B, and may be any form which allows an instruction to be issued with respect to image quality improving processing or a learned model. Further, the kinds of image quality improving processing illustrated in FIG. 11A and FIG. 11B are one example, and another kind of image quality improving processing that is in accordance with training data used for a learned model may also be included.

Further, similarly to Modification 2, a plurality of images to which image quality improving processing was applied may be simultaneously displayed. At such time, a configuration may also be adopted so that a specification regarding which image quality improving processing to apply can be made. An example of a report screen in such a case is illustrated in FIG. 12A and FIG. 12B.

Figure 12A:
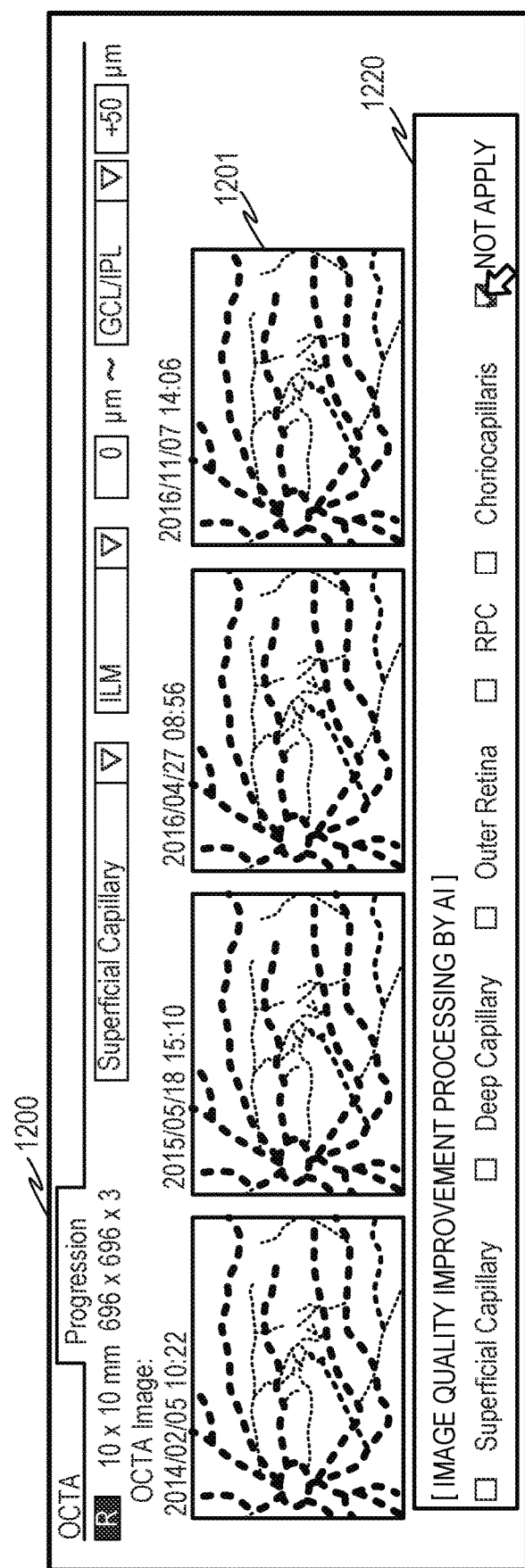
FIG. 12A is a view illustrating an example of a report screen on which a plurality of images before applying image quality improving processing are displayed simultaneously.
Figure 12B:
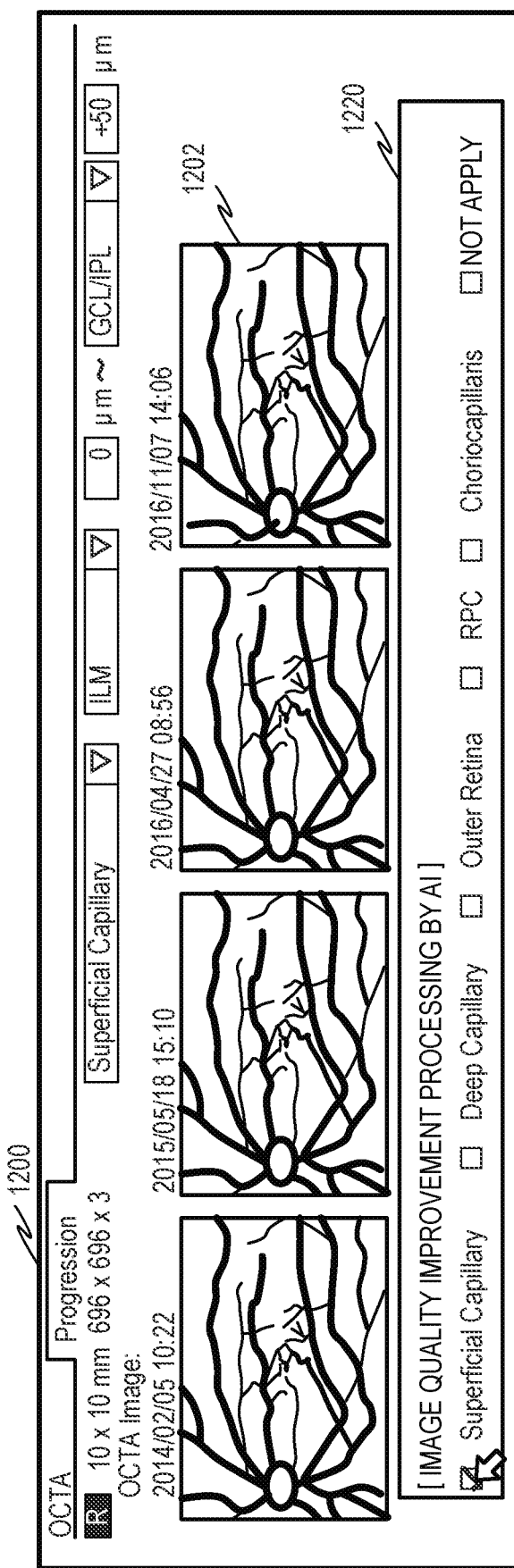
FIG. 12B is a view illustrating an example of a report screen on which a plurality of images to which image quality improving processing was applied are displayed simultaneously.

FIG. 12A and FIG. 12B each illustrate an example of a report screen that switches between and displays a plurality of images before and after image quality improving processing. On a report screen 1200 illustrated in FIG. 12A, OCTA images 1201 before image quality improving processing are shown. On the report screen 1200 illustrated in FIG. 12B, OCTA images 1202 to which image quality improving processing has been applied according to an instruction of the operator are shown. Further, on the report screen 1200 illustrated in FIG. 12A and FIG. 12B, a processing specifying section 1220 for changing the image quality improving processing applied to the OCTA images is shown.

In this case, the selecting unit 925 selects a learned model in accordance with image quality improving processing with respect to which an instruction was issued using the processing specifying section 1220, as the learned model to be used by the image quality improving unit 224. The image quality improving unit 224 performs image quality improving processing on the plurality of OCTA images 1201 using the learned model selected by the selecting unit 925. The display controlling unit 250 causes a plurality of OCTA images 1202 of high image quality that were generated to be displayed at one time on the report screen 1200 as illustrated in FIG. 12B.

Note that, although image quality improving processing with respect to an OCTA image is described above, a learned model may also be selected and changed according to an instruction of the operator with respect to image quality improving processing performed on a tomographic image or an intensity en-face image or the like. Note that, a plurality of images before and after image quality improving processing may also be displayed in a juxtaposed manner or a superimposed manner on the report screen. In this case also, a plurality of images to which image quality improving processing was applied according to an instruction from the operator can be displayed at one time.

Embodiment 3

In Embodiments 1 and 2, the image quality improving unit 224 automatically executes image quality improving processing after a tomographic image or an OCTA image is imaged. However, it may sometimes take a long time to perform image quality improving processing using a learned model that the image quality improving unit 224 executes. Further, it also takes time to perform generation of motion contrast data by the motion contrast generating unit 222 and generation of an OCTA image by the en-face image generating unit 223. Consequently, in the case of displaying an image after waiting for image quality improving processing to be completed after imaging, it may take a long time to display the image after imaging.

In this regard, when imaging an eye to be examined using an OCT apparatus, in some cases the imaging is not successfully performed due to blinking or unintended movement of the eye to be examined or the like. Therefore, the convenience of the OCT apparatus can be enhanced by allowing the operator to confirm, at an early stage, whether or not imaging was successful. Thus, in Embodiment 3, an OCT apparatus is configured so that, prior to generation and display of a high quality OCTA image, confirmation of an imaged image can be performed at an early stage by displaying an intensity en-face image or OCTA image based on tomographic information obtained by imaging the eye to be examined.

Figure 13:
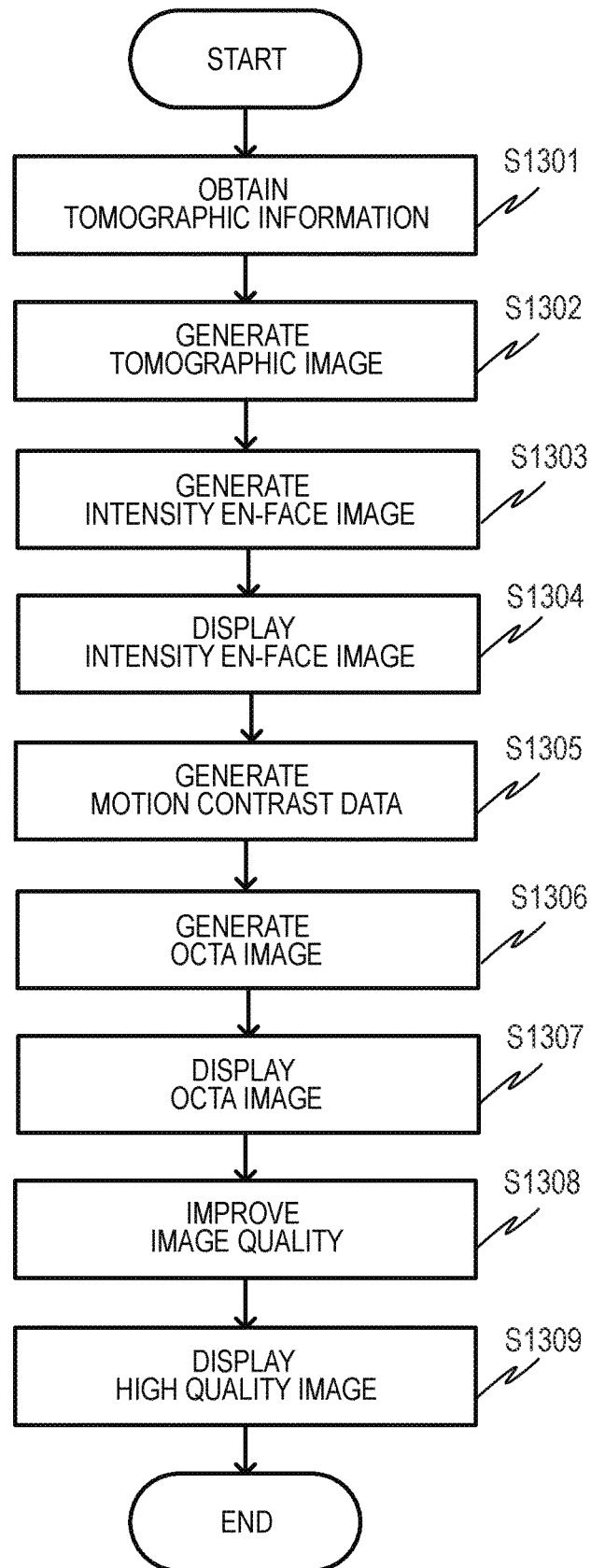
FIG. 13 is a flowchart of a series of image processing operations according to Embodiment 3.

Hereunder, the OCT apparatus according to the present embodiment is described referring to FIG. 13. Note that, since a configuration of the OCT apparatus according to the present embodiment is similar to the configuration of the OCT apparatus 1 according to Embodiment 1, components that are the same as components illustrated in FIG. 1 are denoted by the same reference numerals as those in Embodiment 1, and a description of the components is omitted hereunder. Hereunder, the OCT apparatus according to the present embodiment is described centering on differences from the OCT apparatus 1 according to Embodiment 1.

FIG. 13 is a flowchart of a series of image processing operations according to the present embodiment. First, in step S1301, the obtaining unit 210 obtains a plurality of items of three-dimensional tomographic information obtained by imaging the eye to be examined E, from the OCT imaging unit 100.

Since step S1302 is the same as step S502 according to Embodiment 1, a description thereof is omitted here. Upon a three-dimensional tomographic image being generated in step S1302, the processing shifts to step S1303.

In step S1303, the en-face image generating unit 223 generates a front image (intensity en-face image) of the fundus by projecting the three-dimensional tomographic image generated in step S1302 on a two-dimensional plane. Thereafter, in step S1304, the display controlling unit 250 displays the generated intensity en-face image on the display unit 270.

Since step S1305 and step S1306 are the same as steps S503 and S504 according to Embodiment 1, a description of these steps is omitted here. Upon anOCTA image being generated in step S1306, the processing shifts to step S1307. In step S1307, the display controlling unit 250 causes the display unit 270 to switch from displaying the intensity en-face image to displaying the OCTA image before image quality improving processing that was generated in step S1306.

In step S1308, similarly to step S505 according to Embodiment 1, the image quality improving unit 224 subjects the OCTA image generated in step S1306 to image quality improving processing using a learned model to thereby generate a high quality OCTA image. In step S1309, the display controlling unit 250 causes the display unit 270 to switch from displaying the OCTA image before image quality improving processing to displaying the generated high quality OCTA image.

As described above, before obtainment of an OCTA image by the obtaining unit 210, the display controlling unit 250 according to the present embodiment causes an intensity en-face image (third image) that is a front image which was generated based on tomographic data obtained in the depth direction of the eye to be examined to be displayed on the display unit 270. Further, immediately after an OCTA image is obtained, the display controlling unit 250 causes the display unit 270 to switch from displaying the intensity en-face image to displaying the OCTA image. In addition, after a high quality OCTA image is generated by the image quality improving unit 224, the display controlling unit 250 causes the display unit 270 to switch from displaying the OCTA image to displaying the high quality OCTA image.

Thus, the operator can check a front image of eye to be examined immediately after imaging, and can immediately determine whether or not the imaging was successful. Further, since an OCTA image is displayed immediately after the OCTA image is generated, the operator can determine at an early stage whether a plurality of items of three-dimensional tomographic information for generating motion contrast data have been appropriately obtained.

Note that, with respect to a tomographic image or an intensity en-face image or the like also, by displaying the tomographic image or the intensity en-face image prior to performing image quality improving processing, the operator can determine at an early stage whether or not imaging was successful.

Although in the present embodiment the processing for generating motion contrast data (step S1305) is started after the processing for displaying an intensity en-face image (step S1304), the timing at which to start the processing for generating motion contrast data is not limited thereto. The motion contrast generating unit 222, for example, may start the processing for generating motion contrast data concurrently with the processing for generating (step S1303) or the processing for displaying an intensity en-face image (step S1304). Similarly, the image quality improving unit 224 may start the image quality improving processing (step S1308) concurrently with the processing for displaying an OCTA image (step S1307).

Embodiment 4

In Embodiment 1, an example in which OCTA images before and after image quality improving processing are switched and displayed was described. In contrast, in Embodiment 4, a comparison is made between images before and after image quality improving processing.

Figure 14:
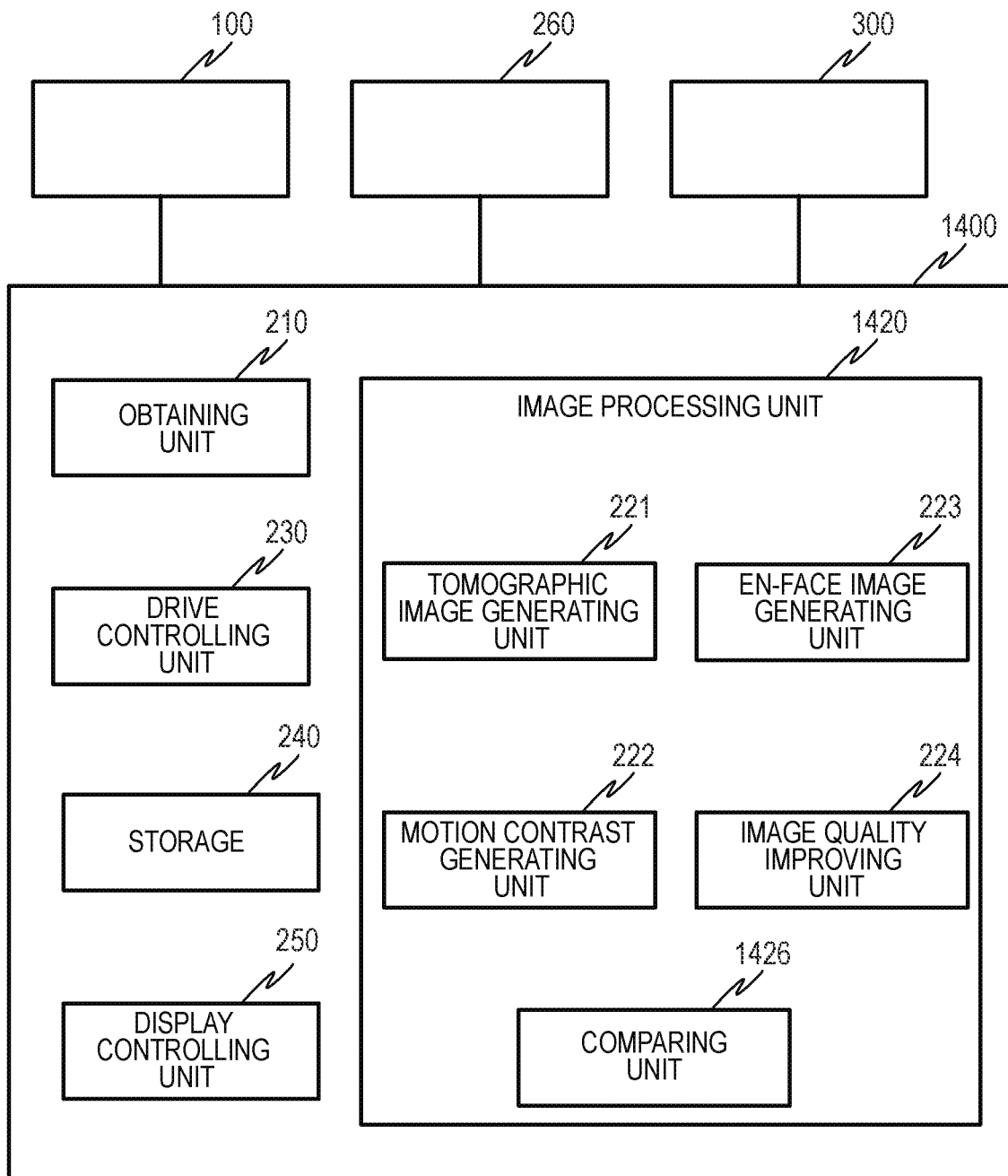
FIG. 14 is a view illustrating a schematic configuration of a controlling unit according to Embodiment 4.
Figure 15:
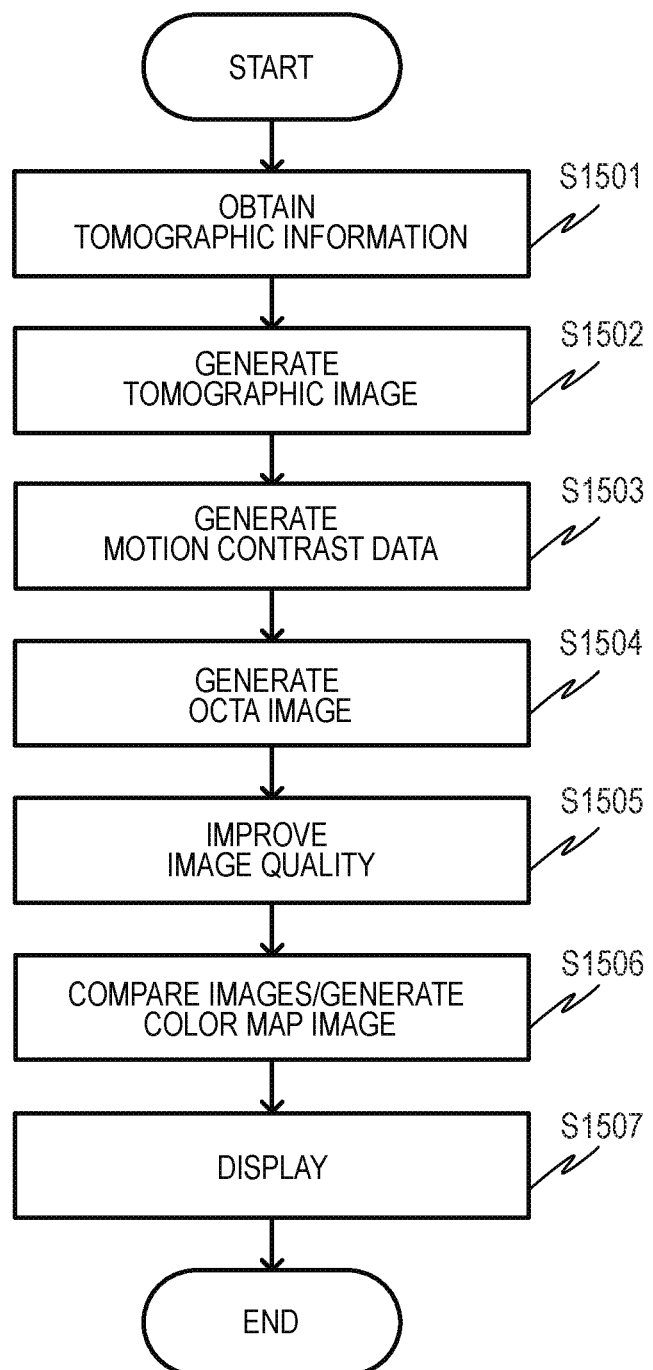
FIG. 15 is a flowchart of a series of image processing operations according to Embodiment 4.

Hereunder, an OCT apparatus according to the present embodiment is described referring to FIG. 14 and FIG. 15. Note that, since a configuration of the OCT apparatus according to the present embodiment is the same as the configuration of the OCT apparatus 1 according to Embodiment 1 with the exception of the controlling unit, components that are the same as components illustrated in FIG. 1 are denoted by the same reference numerals as those in Embodiment 1, and a description of the components is omitted hereunder. Hereunder, the OCT apparatus according to the present embodiment is described centering on differences from the OCT apparatus 1 according to Embodiment 1.

FIG. 14 is a view illustrating a schematic configuration of a controlling unit 1400 according to the present embodiment. Note that, apart from an image processing unit 1420 and a comparing unit 1426, the components of the controlling unit 1400 according to the present embodiment are the same as the respective components of the controlling unit 200 according to Embodiment 1. Therefore, components that are the same as components illustrated in FIG. 2 are denoted by the same reference numerals as those in Embodiment 1, and a description of the components is omitted hereunder.

In addition to the tomographic image generating unit 221, the motion contrast generating unit 222, the en-face image generating unit 223 and the image quality improving unit 224, the comparing unit 1426 is also provided in the image processing unit 1420 of the controlling unit 1400.

The comparing unit 1426 performs a comparison between the image (original image) before image quality improving processing is performed by the image quality improving unit 224 and the image after image quality improving processing is performed. More specifically, the comparing unit 1426 compares the images before and after the image quality improving processing, and calculates the respective differences between the pixel values at corresponding pixel positions in the images before and after the image quality improving processing.

The comparing unit 1426 then generates a color map image that is colored according to the magnitude of the difference values. For example, in a case where a pixel value of the image after the image quality improving processing is larger relative to a pixel value of the image before the image quality improving processing, a warm color (yellow to orange to red) tone is used, while in a case where a pixel value of the image after the image quality improving processing is smaller, a cold color (yellow-green to green to blue) tone is used. By using such a color scheme, it can be easily identified that a location indicated by a warm color on the color map image is tissue that was restored (or newly created) by the image quality improving processing. Similarly, it can be easily identified that a location indicated by a cold color on the color map image is noise that has been removed (or tissue that has been erased) by the image quality improving processing.

Note that, the color scheme of the color map image in question is one example. For example, the color scheme of the color map image may be arbitrarily set according to a desired configuration, such as applying a color scheme of color tones that differ according to the magnitude of pixel values in the image after the image quality improving processing relative to the pixel values in the image before the image quality improving processing.

The display controlling unit 250 can superimpose the color map image generated by the comparing unit 1426 on the image before the image quality improving processing or the image after the image quality improving processing, and display the resultant superimposed image on the display unit 270.

Next, a series of image processing operations according to the present embodiment is described referring to FIG. 15. Note that, since step S1501 to step S1505 are the same as step S501 to S505 according to Embodiment 1, a description of these steps is omitted here. Upon a high quality OCTA image being generated by the image quality improving unit 224 in step S1505, the processing shifts to step S1506.

In step S1506, the comparing unit 1426 compares the OCTA image generated in step S1504 with the high quality OCTA image generated in step S1505 to calculate differences between the respective pixel values, and generates a color map image based on the differences between the respective pixel values. Note that, instead of differences between pixel values in images before and after image quality improving processing, the comparing unit 1426 may perform a comparison between images using another method such as by using ratios of pixel values or correlation values between images before and after image quality improving processing, and may generate a color map image based on the comparison result.

In step S1507, the display controlling unit 250 superimposes the color map image on the image before the image quality improving processing or the image after the image quality improving processing, and displays the resultant superimposed image on the display unit 270. At such time, the display controlling unit 250 can set a degree of transparency with respect to the color map so as to ensure that the color map image does not conceal the image on which the color map image is to be superimposed, and cause the color map image to be displayed in a superimposed manner on the target image.

Further, in the color map image, the display controlling unit 250 may set the degree of transparency to a high value at a location at which a difference between the images before and after image quality improving processing is small (a pixel value of the color map image is low), or may set the degree of transparency so that a location at which the difference is less than or equal to a predetermined value is completely transparent. By setting the degree of transparency in such a manner, the image displayed below the color map image, and the color map image can both be visually recognized in a favorable manner. Note that, with regard to the degree of transparency of the color map image, the comparing unit 1426 may also generate a color map image including the degree of transparency settings.

As described above, the controlling unit 1400 according to the present embodiment includes the comparing unit 1426 that compares a first medical image, and a second medical image on which image quality improving processing was performed. The comparing unit 1426 calculates a difference between the first medical image and the second medical image, and generates a color map image that was colored based on the difference. The display controlling unit 250 controls the display of the display unit 270 based on comparison result obtained by the comparing unit 1426. More specifically, the display controlling unit 250 superimposes the color map image on the first medical image or the second medical image, and displays the resulting superimposed image on the display unit 270.

Thus, a change between the images that was caused by image quality improving processing can be easily confirmed by observing the color map image superimposed on the images before and after the image quality improving processing. Therefore, even if tissue that does not actually exist is visualized in an image by the image quality improving processing or tissue which originally existed was erased from the image by the image quality improving processing, the operator can more easily identify such tissue, and can more easily determine the authenticity of the tissue. Further, in accordance with the color scheme of the color map image, the operator can easily identify whether a location is a location that was newly visualize by the image quality improving processing or is a location that was erased by the image quality improving processing.

Note that, the display controlling unit 250 can enable or disable the superimposed display of the color map image according to an instruction from the operator. An operation for turning superimposed display of the color map image on or off may be applied simultaneously to a plurality of images displayed on the display unit 270. In this case, the comparing unit 1426 can generate a color map image for each of the corresponding images before and after the image quality improving processing, and the display controlling unit 250 can superimpose and display a color map image on the corresponding image before image quality improving processing or image after image quality improving processing. Further, the display controlling unit 250 may cause the image before image quality improving processing or the image after image quality improving processing to be displayed on the display unit 270 before displaying the color map image.

Note that, although the present embodiment is described by taking an OCTA image as an example, similar processing can be performed in the case of performing image quality improving processing on a tomographic image or an intensity en-face image or the like. Further, the comparison processing and processing for displaying a color map according to the present embodiment can also be applied to the OCT apparatuses according to Embodiment 2 and Embodiment 3.

(Modification 4)

Further, the comparing unit 1426 may perform a comparison of images before and after image quality improving processing, and depending on the result of the comparison by the comparing unit 1426, the display controlling unit 250 may display a warning on the display unit 270. More specifically, in a case where a difference between pixel values in images before and after image quality improving processing which was calculated by the comparing unit 1426 is greater than a predetermined value, the display controlling unit 250 displays a warning on the display unit 270. According to such a configuration, in a case where, in a generated high quality image, tissue that does not actually exist was generated or tissue which originally existed was erased by a learned model, the attention of the operator can be drawn to that fact. Note that, the comparison between a difference and a predetermined value may be performed by the comparing unit 1426 or may be performed by the display controlling unit 250. Further, instead of a difference, a statistical value such as an average value of differences may be compared with a predetermined value.

In addition, the display controlling unit 250 may be configured so that, in a case where a difference between images before and after the image quality improving processing is greater than a predetermined value, the image after image quality improving processing was performed is not displayed on the display unit 270. In this case, in a generated high quality image, if tissue that does not actually exist was generated or tissue which originally existed was erased by a learned model, the occurrence of a misdiagnosis based on the high quality image in question can be suppressed. Note that, the comparison between a difference and a predetermined value may be performed by the comparing unit 1426 or may be performed by the display controlling unit 250. Further, instead of a difference, a statistical value such as an average value of differences may be compared with a predetermined value.

(Modification 5)

Figure 16A:
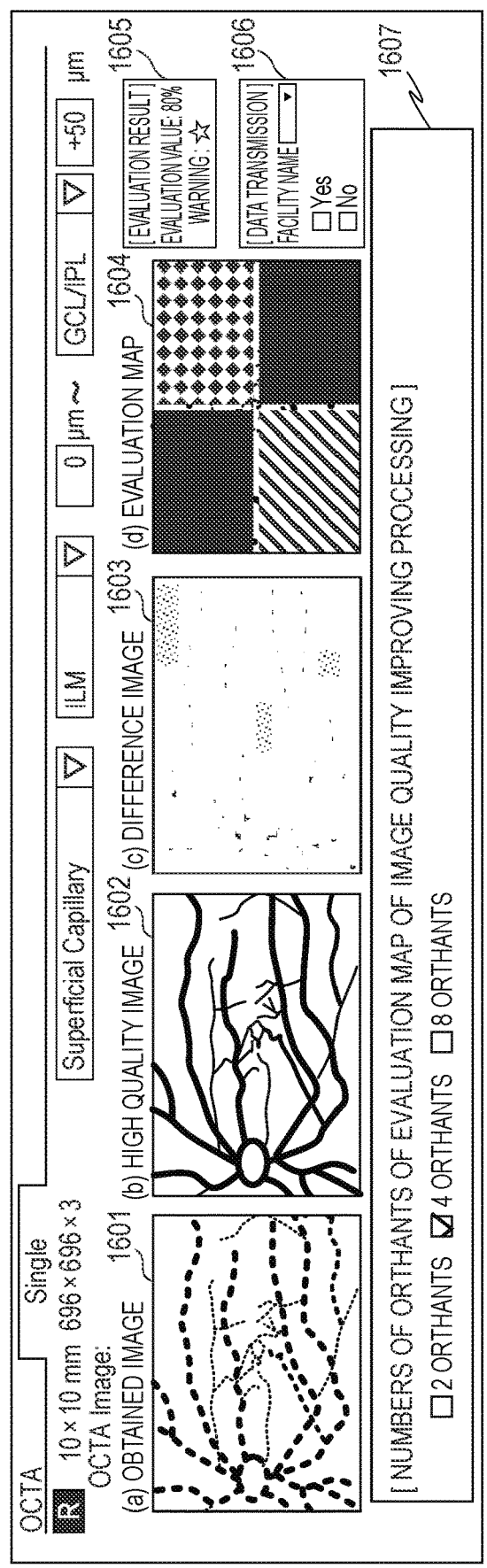
FIG. 16A is a view illustrating an example of a report screen (display screen) according to a Modification.
Figure 16B:
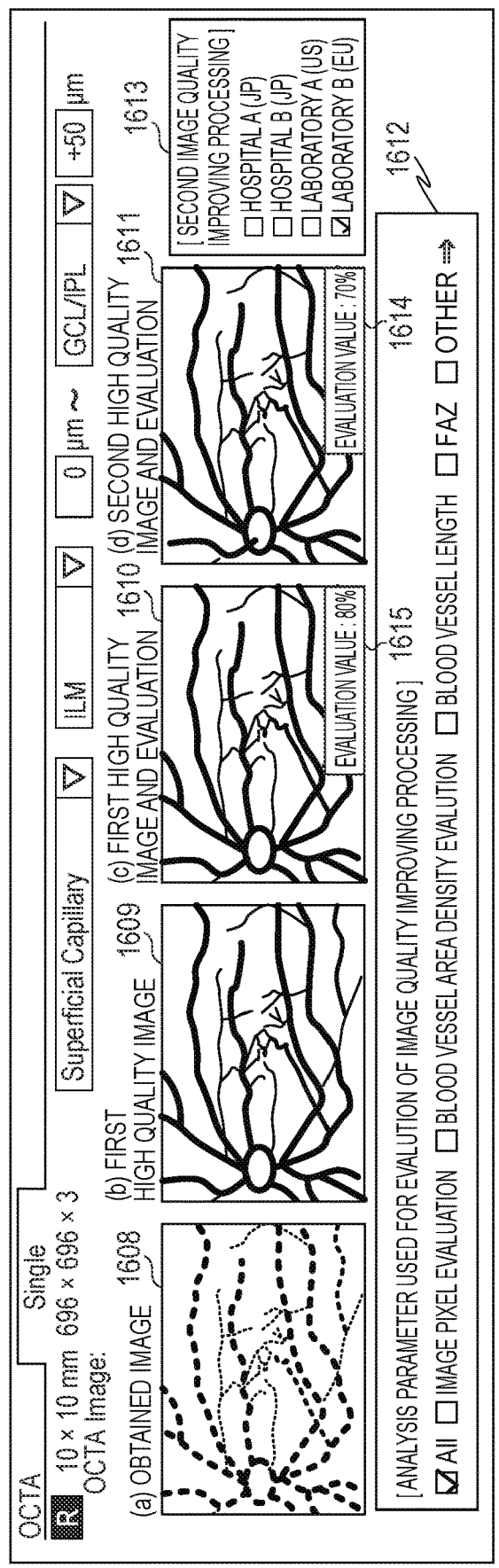
FIG. 16B is a view illustrating an example of the report screen (display screen) according to a Modification.

Further, the comparing unit 1426 may perform a comparison between analysis results obtained by analyzing the images before and after image quality improving processing, respectively. More specifically, for each pixel position, the comparing unit 1426 calculates a difference (degree of increase/decrease or attenuation) between the analysis results obtained by analyzing the images before and after image quality improving processing, respectively. For example, as illustrated in FIG. 16A, a difference image 1603 is acquired from images before and after image quality improving processing (obtained image 1601, high quality image 1602), and places where a difference is increasing and places where a difference is decreasing in the difference image are distinguished using different colors or the like, and information such as a place where an image improved which is easy for the user to understand is displayed on the display unit 270. Note that, the difference image 1603 may be superimposed on at least one of the images before and after image quality improving processing (the obtained image 1601 and the high quality image 1602). Further, various map displays such as an evaluation map 1604 may be displayed that show regions in which there is a large change, and not pixel units. Specifically, such a map may be displayed on the display unit 270 as an evaluation map showing an evaluation result for respective regions that were divided into a plurality of orthants. At this time, for example, as illustrated in a display area 1607, two, four or eight orthants or the like is conceivable as the number of orthants, although the number of orthants is not limited thereto. Further, in a case where the number of orthants is two, for example, the evaluation map may be divided into upper and lower regions, or may be divided into left and right regions. Further, it is conceivable that the center of the orthants is, for example, a site of interest such as the macular area or optic nerve head, although the present modification is not limited thereto. Further, a configuration may be adopted so that the operator can specify any position on an image after image quality improving processing or a difference image as the center of the orthants. Further, the matching rate of a result calculated as a difference between analysis results obtained by analyzing images before and after image quality improving processing, respectively, can also be converted into numerical form and displayed, for example, as an evaluation result 1605 of image quality improving processing, or an evaluation value 1615 of image quality improving processing that is illustrated in FIG. 16B. At this time, with respect to each orthant of the evaluation map 1604, the evaluation of the respective orthants may be indicated by shading by, for example, displaying in a manner such that, the higher the evaluation value is, the thicker the shading that is displayed, and conversely, the lower the evaluation value is, the lighter the shading that is displayed, or an evaluation value may be displayed for each orthant. In this regard, there is a probability that image quality improving processing will be performed which mistakenly recognizes an artifact caused by movement or blinking of the eye or the like as being a blood vessel extending along the main scanning direction. In such a case, for example, in a case where the optic nerve head has been set at the center of the orthants, because there are many blood vessels along the main scanning direction on the macular area side, there is a probability that the matching rate will be lower than on the opposite side to the macular area. Therefore, by showing an evaluation value for each orthant, the operator can efficiently evaluate the image quality improving processing result.

Here, the analysis result is a value relating to at least one analysis parameter illustrated in a display area 1612 in FIG. 16B. For example, the analysis result is at least one of a value relating to a blood vessel (for example, blood vessel area density, blood vessel length density, or blood vessel length), a value relating to an avascular zone (for example, circumferential length, volume, area, or circularity), and a value relating to an edema zone (diseased region such as a choroidal neovascular site) (for example, volume or area). Further, the analysis result may be, for example, a two-dimensional map (analysis map) of a value relating to at least one analysis parameter. At this time, the display controlling unit 250 may cause a comparison result (result of comparing analysis results) obtained by the comparing unit 1426 to be displayed on the display unit 270. More specifically, as illustrated as the evaluation map 1604 in FIG. 16A, the display controlling unit 250 may cause a color map image that was colored according to the magnitude of difference values to be displayed as a comparison result on the display unit 270. Further, as illustrated in the evaluation result 1605 in FIG. 16A, in a case where a difference between analysis results is greater than a predetermined value, the display controlling unit 250 may cause a warning to be displayed on the display unit 270. Furthermore, the display controlling unit 250 may cause a region in which a difference between the analysis results is greater than a predetermined value to be displayed distinguishably from another region in which the difference between the analysis results is equal to or less than the predetermined value on the display unit 270. Further, in a case where the number of pixels for which the difference is greater than a predetermined value is greater than another predetermined value, the display controlling unit 250 may cause a warning to be displayed on the display unit 270. Further, a number of these displays may be displayed simultaneously.

According to such a configuration, in a high quality image that is generated by a learned model, for example, in a case where tissue that does not actually exist was generated or a case where tissue that originally existed was erased, the attention of the operator can be easily drawn to that fact. Note that, instead of a difference for each pixel position, a statistical value such as an average value of differences may be compared with a predetermined value. In this case, if images before and after image quality improving processing are evaluated only by being directly compared with each other, there is a probability that places on which attention is not focused will also be evaluated. On the other hand, depending on the kind of analysis (for example, blood vessel density or thickness of a specific layer), various sites of interest (for example, blood vessels and specific layers) exist. Therefore, it can be considered that when analysis results of images before and after image quality improving processing are compared and evaluated, an evaluation result for a site of interest can be more effectively obtained than in the case of evaluating the images by directly comparing the images with each other. Note that, a configuration may be adopted so that a direct comparison between the aforementioned images and a comparison between analysis results for the images may be selectively executed according to the kind of images, and so that any of the evaluation results after executing each kind of comparison may be selectively displayed on the display unit 270. For example, in the case of an OCTA image, since there is a probability that a problem will arise whereby an artifact is erroneously recognized as a blood vessel as described above, evaluation values obtained by comparing analysis results may be selectively displayed on the display unit 270.

(Modification 6)

In addition, a plurality of images obtained by imaging approximately the same location of an eye to be examined at different times, and a plurality of images obtained by performing image quality improving processing using the aforementioned plurality of images may be compared by the comparing unit 1426 before and after the image quality improving processing. More specifically, with respect to the plurality of images, the comparing unit 1426 calculates a difference between pixel values at pixel positions corresponding to each other in the images before and after image quality improving processing. At this time, with respect to the plurality of images, the display controlling unit 250 may cause comparison results (differences) obtained by the comparing unit 1426 to be displayed on the display unit 270. By this means, the operator may select any of the plurality of images by taking into consideration the respective comparison results (differences). Further, the display controlling unit 250 may cause a statistical value such as an average value of a plurality of comparison results (differences) corresponding to the plurality of images to be displayed on the display unit 270. Furthermore, the comparing unit 1426 may compare a single image obtained by averaging a plurality of images, with an image obtained by performing image quality improving processing using the single image in question. Note that, in a case where the plurality of images are front images generated based on information pertaining to ranges in the depth direction of an eye to be examined, it is better if the ranges in the depth direction are common with each other. At this time, for example, after a range in the depth direction of one of the images has been set according to an instruction from the operator, the range in the depth direction of the other images may be set.

Figure 17:
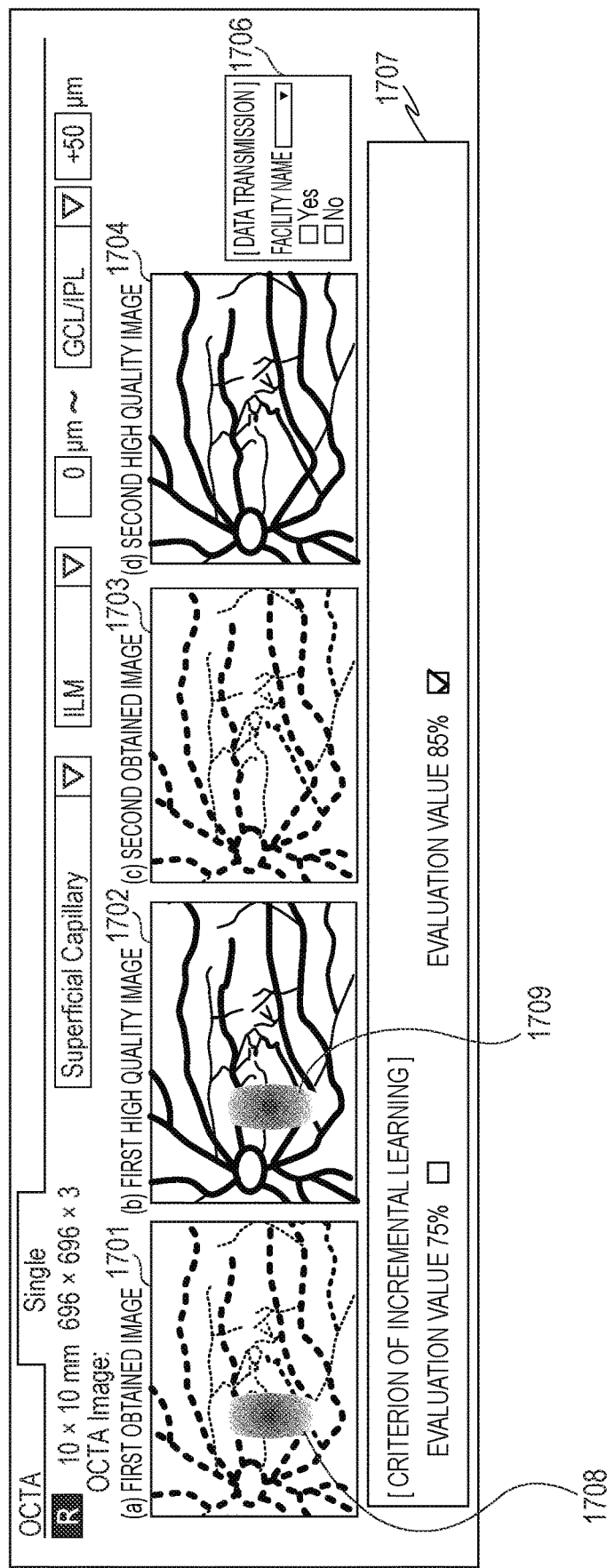
FIG. 17 is a view illustrating an example of the report screen (display screen) according to a Modification.

For the purpose of simplicity, in the present modification a case in which two OCTA images are obtained will be described. Two OCTA image are obtained as illustrated by a first obtained image 1701 and a second obtained image 1703 illustrated in FIG. 17. Images are acquired (in FIG. 17, described as a "first high quality image" and a "second high quality image") that are obtained by subjecting the first obtained image 1701 and the second obtained image 1703 to image quality improving processing. First, as in the case of the first obtained image 1701, when an opaque object such as the vitreous body enters the imaging range during acquisition of the OCTA image, an OCTA image in which a shadow 1708 is present is output. Therefore, when the first obtained image 1701 is subjected to image quality improving processing, a first high quality image 1702 that has a shadow 1709 is output. Further, when an image in which there is no shadow as in the case of the second obtained image 1703 is subjected to image quality improving, the image quality improving is suitably performed and a second high quality image 1704 can be obtained. Thus, by presenting the evaluation of image quality improving processing with respect to the first obtained image 1701 and the second obtained image 1703, respectively, as a numerical value, a suitable determination by the physician can be supported. In addition, since an image in which the influence of opacity or the like is present will have a low evaluation value, an image with a high evaluation value may be displayed with priority. For example, an image with a high evaluation value may be selectively displayed without displaying an image with a low evaluation value. Note that, image quality improving processing may be performed after the first obtained image 1701 and the second obtained image 1703 are each subjected to averaging processing.

(Modification 7)

Further, in the various embodiments and modifications described above, diverse kinds of diagnostic information can be presented to the physician by conducting similar evaluations using an apparatus having a plurality of image quality improving units (a plurality of learned models obtained by performing learning using different training data). Here, the plurality of image quality improving units are units that can selectively execute image quality improving processing using a learned model obtained by performing learning with training images that were selected by a major reading center, respectively, as in the case of second image quality improving processing 1613 illustrated in FIG. 16B. For example, by selecting any one of a plurality of facilities (hospitals or laboratories or the like) as the second image quality improving processing 1613 that is different from the first image quality improving processing that had been prepared in advance, the user can cause not only an image (first high quality image 1609) obtained by performing the first image quality improving processing to be displayed, but can also cause an image (second high quality image 1611) obtained by performing the second image quality improving processing to be displayed. Further, by describing the country name (race) together with the facility name, the image quality of an image of a gene-dependent disease or a unique fundus image (myopia, normal-tension glaucoma, angiectopia or the like) can be suitably improved by the second image quality improving processing 1613. At this time, after obtaining an evaluation result such as the evaluation value 1615 by comparing an obtained image 1608 and a first high quality image 1610 (1609), an evaluation result such as an evaluation value 1614 can be obtained by comparing the obtained image 1608 and the second high quality image 1611. Thus, for example, from the respective evaluation results, appropriate image quality improving processing can be selected and can be reflected in the next and subsequent diagnoses. Further, with regard to evaluation of the image quality improving processing described in Modification 4 to Modification 7, when it is evaluated that processing is appropriate (the selected image when a plurality of images are obtained, or the selected processing among a plurality of kinds of image quality improving processing), by performing data transmission with respect to a facility name and the processing contents as illustrated in a display area 1606 or a display area 1706, it is possible to perform incremental learning and thereby enable more flexible image quality improving processing. The incremental learning may be performed at a server, or may be performed in a cloud-based device, or at an equipment manufacturer. Further, by performing incremental learning, as in the example of Modification 6, the image 1704 in which there is no shadow can be obtained from the image 1701 in which there is a shadow by performing image quality improving processing.

In this case, in order to increase the accuracy of learning of the image quality improving processing, incremental learning may be performed in which pairs of images for which the aforementioned evaluation value obtained by converting a matching rate into numerical form is high to a certain extent is adopted as training data. Therefore, a configuration may be adopted so that, as illustrated in a display area 1707 in FIG. 17, an evaluation value to serve as a criterion for determining whether or not to utilize the relevant image as training data of incremental learning can be selected. For example, in a case where one of 75% and 85% can be selected as the aforementioned criterion, although the quality of the training data will be higher if the evaluation value of 85% is selected, there is a probability that a large number of training data items will not be obtained, while on the other hand, although training data in which the quality is relatively low will be included if the evaluation value of 75% is selected, there is a probability that a large number of training data items will be obtained. Note that, the selectable evaluation values are not limited to these evaluation values, and a configuration may also be adopted so that a selection can be made from three or more evaluation values. Further, in the case of performing image quality improving processing of a plurality of images, a configuration may be adopted so that the aforementioned criterion can be selected for each of the images. In addition, a pre-prepared evaluation value may be adopted as the criterion, and a configuration may also be adopted so that an image is not used for incremental learning when there is a large difference in comparison with the evaluation value set as the criterion.

As described in the foregoing Modification 4 to Modification 7, by performing an evaluation using an image that underwent image quality improving processing and the source image, it is possible to support a decision of the physician with regard to whether or not it is good to make a diagnosis using an image that underwent image quality improving processing. Depending on the numerical values, the physician can decide to perform a reexamination (reacquire an OCTA image). Further, a threshold value may be stored in the apparatus, and a reexamination may be automatically performed. By adding an incremental learning function to an apparatus having an evaluation function, a more appropriate image quality improving processing program can be provided.

(Modification 8)

In the various embodiments and modifications described above, the display controlling unit 250 can cause the display unit 270 to display an image selected according to an instruction from the examiner from among a high quality image generated by the image quality improving unit 224 and an input image. Further, in response to an instruction from the examiner, the display controlling unit 250 may switch the image displayed on the display unit 270 from an imaged image (input image) to a high quality image. In other words, the display controlling unit 250 may change the display of a low quality image to the display of a high quality image in response to an instruction from the examiner. Further, the display controlling unit 250 may change the display of a high quality image to the display of a low quality image in response to an instruction from the examiner.

In addition, the image quality improving unit 224 may start (input an image to an image quality improving engine) image quality improving processing by an image quality improving engine (learned model for improving image quality) in response to an instruction from the examiner, and the display controlling unit 250 may cause the display unit 270 to display a high quality image generated by the image quality improving unit 224. In contrast, when an input image is imaged by the imaging apparatus (OCT imaging unit 100), the image quality improving engine may automatically generate a high quality image based on the input image, and the display controlling unit 250 may cause the display unit 270 to display the high quality image in response to an instruction from the examiner. Here, the term "image quality improving engine" includes a learned model that performs the image quality improving processing described above.

Note that, these processing operations can be similarly performed with respect to the output of an analysis result also. In other words, the display controlling unit 250 may change the display of an analysis result for a low quality image to the display of an analysis result for a high quality image in response to an instruction from the examiner. Further, the display controlling unit 250 may change the display of an analysis result for a high quality image to the display of an analysis result for a low quality image in response to an instruction from the examiner. Naturally, the display controlling unit 250 may change the display of an analysis result for a low quality image to the display of a low quality image in response to an instruction from the examiner. Further, the display controlling unit 250 may change the display of a low quality image to the display of an analysis result for a low quality image in response to an instruction from the examiner. Furthermore, the display controlling unit 250 may change the display of an analysis result for a high quality image to the display of a high quality image in response to an instruction from the examiner. Further, the display controlling unit 250 may change the display of a high quality image to the display of an analysis result for a high quality image in response to an instruction from the examiner.

In addition, the display controlling unit 250 may change the display of an analysis result for a low quality image to the display of a different kind of analysis result for a low quality image in response to an instruction from the examiner. Further, the display controlling unit 250 may change the display of an analysis result for a high quality image to the display of a different kind of analysis result for a high quality image in response to an instruction from the examiner.

In this case, the display of an analysis result for a high quality image may be performed such that the analysis result for the high quality image is displayed in a superimposed manner on the high quality image with any degree of transparency. Further, the display of an analysis result for a low quality image may be performed such that the analysis result for the low quality image is displayed in a superimposed manner on the low quality image with any degree of transparency. At this time, changing to the display of an analysis result may be, for example, a change to a state in which the analysis result is superimposed with any degree of transparency on the image that is being displayed. Further, changing to the display of an analysis result may be, for example, a change to the display of an image (for example, a two-dimensional map) obtained by subjecting an analysis result and an image to blending processing with any degree of transparency.

Note that, an image relating to processing for displaying an image, image quality improving, and image analysis and the like according to the present modification may also be a tomographic image, and not only an OCTA image (motion contrast front image). In addition, the kind of image is not limited to a tomographic image acquired by a B-scan, and may be a different image such as an SLO (scanning laser ophthalmoscope) image, a fundus image or a fluorescence fundus image. In this case, a user interface for executing image quality improving processing may be a user interface for instructing the execution of image quality improving processing with respect to a plurality of images of different kinds, or may be a user interface for selecting any image from a plurality of images of different kinds and instructing the execution of image quality improving processing.

For example, in the case of subjecting tomographic images acquired by a B-scan to image quality improving and displaying the images, at least one of the tomographic images displayed may be subjected to image quality improving and displayed. Further, a tomographic image that was subjected to image quality improving may be displayed in a region in which an OCTA front image is being displayed. Further, a tomographic image acquired by a B-scan may be a tomographic image acquired by a B-scan that was obtained using motion contrast data, and not only an intensity tomographic image. Note that, the number of tomographic images subjected to image quality improving and displayed may be only one tomographic image or may be a plurality of tomographic images. In a case where only one tomographic image is to be displayed, a tomographic image obtained by, for example, circular scanning or the like may be subjected to image quality improving and displayed. Further, in a case where a plurality of tomographic images are to be displayed, tomographic images acquired at different positions to each other in the sub-scanning direction may be displayed, and for example in a case where a plurality of tomographic images obtained by cross-scanning or the like are subjected to image quality improving and displayed, the respective images in the different scanning directions may be displayed. Note that, since the image features of a plurality of tomographic images obtained by cross-scanning or the like are similar to each other in many cases, for example, images obtained in respective scanning directions may be subjected to image quality improving using a common learned model obtained by performing learning using these tomographic images as training data. Further, for example, in a case where a plurality of tomographic images obtained by radial scanning or the like are subjected to image quality improving and displayed, some selected (plurality of) tomographic images (for example, two tomographic images at positions symmetrical to each other with respect to a reference line) may each be displayed. In addition, a plurality of tomographic images obtained at different dates and times may be displayed on a display screen for follow-up observation, and an instruction for image quality improvement or an analysis result (for example, the thickness of a specific layer) may be displayed. Further, image quality improving processing may be executed on a tomographic image based on information stored in a database.

Similarly, in the case of subjecting an SLO fundus image to image quality improving and displaying the resultant image, for example, a displayed SLO fundus image may be subjected to image quality improving and displayed. In addition, in the case of subjecting an intensity en-face image to image quality improving and displaying the resultant image, for example, a displayed intensity en-face image may be subjected to image quality improving and displayed. In addition, a plurality of SLO fundus images or intensity en-face images obtained at different dates and times may be displayed on a display screen for follow-up observation, and an instruction for image quality improvement or an analysis result (for example, the thickness of a specific layer) may be displayed. Further, image quality improving processing may be executed on an SLO fundus image or an intensity en-face image based on information stored in a database. Note that, the displays of the tomographic images, SLO fundus images, and intensity en-face images are examples, and these images may be displayed in any form according to the desired configuration. Further, at least two or more of OCTA front images, tomographic images, SLO fundus images and intensity en-face images may be subjected to image quality improving and displayed based on a single instruction.

Further, in the image processing unit 220 according to the various embodiments and modifications described above, an analyzing unit (not illustrated) may be provided in addition to the image quality improving unit 224 and the like. The analyzing unit subjects a high quality tomographic image generated by the image quality improving unit 224 to image analysis based on an analysis condition that is set for each region. Here, as an analysis condition that is set for each region, for example, layer extraction or blood vessel extraction is set for a region of the retina portion and a region of the choroid portion, and detection of the vitreous body or detachment of the vitreous body is set for a region of the vitreous body portion. Note that, an analysis condition may beset in advance or may be appropriately set by the operator. In a case where layer extraction is set as an analysis condition, the analyzing unit performs layer extraction with respect to a region for which the analysis condition in question is set, and can perform layer thickness value measurement or the like with respect to an extracted layer. Further, in a case where blood vessel extraction is set as an analysis condition, the analyzing unit performs blood vessel extraction with respect to a region for which the analysis condition in question is set, and can perform blood vessel density measurement or the like with respect to an extracted blood vessel. In addition, in a case where detection of the vitreous body or detachment of the vitreous body is set as an analysis condition, the analyzing unit performs detection of the vitreous body or detachment of the vitreous body with respect to a region for which the analysis condition in question is set. Thereafter, the analyzing unit can perform quantification with regard to the detected vitreous body or detachment of the vitreous body, and determine the thickness, width, area or volume or the like of the vitreous body or the detachment of the vitreous body. Note that, the analysis conditions are not limited to the conditions described above, and may be arbitrarily set according to a desired configuration. For example, detection of the fibrous structure of the vitreous body may be set for the region of the vitreous body portion. In this case, the analysis unit can perform quantification of the detected fibrous structure of the vitreous body, and determine the thickness, width, area or volume or the like of the fibrous structure. Further, analysis processing according to the analysis conditions is also not limited to the processing described above, and may be arbitrarily set according to a desired configuration. Further, the display controlling unit 250 may cause the result of image analysis performed by the analyzing unit to be displayed on the display unit 270 together with the high quality tomographic image or separately from the high quality tomographic image.

(Modification 9)

The display controlling unit 250 in the various embodiments and modifications described above may cause analysis results such as the thickness of a desired layer or various blood vessel densities to be displayed on a report screen in a display screen. Further, a parameter value (distribution) relating to a site of interest including at least one of the optic nerve head, the macular area, a vascular zone, a nerve fascicle, a vitreous region, a macular region, a choroid region, a sclera region, a lamina cribrosa region, a retinal layer boundary, a retinal layer boundary edge, a photoreceptor cell, a blood cell, a blood vessel wall, a blood vessel inner wall boundary, a blood vessel external boundary, a ganglion cell, a corneal region, a corner region, and Schlemm's canal and the like may be displayed as an analysis result. At such time, for example, an accurate analysis result can be displayed by analyzing a medical image subjected to various kinds of artifact removal processing. Note that, an artifact may be, for example, a false image region caused by light absorption by a vascular zone or the like, a projection artifact, or a band-like artifact in a front image that arises in the main scanning direction of the measurement light due to the state of the eye to be examined (movement or blinking or the like). Further, an artifact may be of any kind as long as it is an imaging failure region that, for example, randomly arises at each imaging on a medical image of a predetermined site of the subject. Further, the value (distribution) of a parameter relating to a region including at least one of the kind of artifacts (imaging failure regions) described above may be displayed as an analysis result. Furthermore, the value (distribution) of a parameter relating to a region including at least one abnormal site such as drusen, a neovascular site, leucoma (hard exudates), pseudodrusen or the like may be displayed as an analysis result. Further, a comparison result obtained by comparing a standard value or standard range obtained using a standard database and an analysis result may be displayed.

An analysis result may be displayed using an analysis map, or using sectors which indicate statistical values corresponding to respective divided regions or the like. Note that, an analysis result may be generated using a learned model (analysis result generating engine, or a learned model for generating analysis results) obtained by learning the analysis results of a medical image as training data. At such time, the learned model may be a model obtained by learning using training data including a medical image and an analysis result for the medical image, or training data including a medical image and an analysis result for a medical image of a different kind from the relevant medical image or the like. Further, a learned model may be a model obtained by learning using training data including input data in which a plurality of medical images of different kinds of a predetermined site, such as an intensity front image and a motion contrast front image, are taken as a set. Here, an intensity front image corresponds to an intensity en-face image, and a motion contrast front image corresponds to an OCTA en-face image. Further, a configuration may be adopted so that an analysis result obtained using a high quality image generated by a learned model for improving image quality is displayed. Note that, the learned model for improving image quality may be a learned model obtained by learning using training data in which a first image is adopted as input data, and a second image with higher quality than the first image is adopted as correct answer data. At this time, the second image may be, for example, a high quality image for which the contrast was increased or noise was reduced or the like by averaging processing of a plurality of first images (for example, averaging processing of a plurality of first images that were aligned and obtained) or the like.

In addition, input data included in the training data may be a high quality image generated by a learned model for improving image quality, or may be a set composed of a low quality image and a high quality image. Further, the training data may be, for example, data obtained by labeling (performing annotation to) input data for which information including at least one kind of information among an analysis value (for example, an average value or a median value) obtained by analyzing an analysis region, a table including analysis values, an analysis map, and a position of an analysis region such as a sector in an image or the like, is adopted as correct answer data (of supervised learning). Note that, a configuration may be adopted so that an analysis result obtained by a learned model for analysis result generation is displayed in response to an instruction from the examiner.

Further, the display controlling unit 250 in the various embodiments and modifications described above may cause various kinds of diagnosis results such as results relating to glaucoma or age-related macular degeneration to be displayed on a report screen in a display screen. At such time, for example, an accurate diagnosis result can be displayed by analyzing a medical image subjected to various kinds of artifact removal processing as described above. Further, in the diagnosis result, the position of a specified abnormal site or the like may be displayed on the image, and the state of an abnormal site or the like may be displayed using characters or the like. Further, a classification result (for example, Curtin's classification) for an abnormal site may be displayed as a diagnosis result. Further, as a classification result, for example, information (for example, a numerical value indicating a percentage) that indicates the likelihood for each abnormal site may be displayed. In addition, information that is required so that the physician can confirm the diagnosis may be displayed as a diagnosis result. For example, advice such as to perform additional imaging is conceivable as the aforementioned required information. For example, in a case where an abnormal site is detected in a vascular zone in an OCTA image, information on the effect of advising the physician to additionally perform fluorescence imaging using a contrast medium that enables more detailed observation of blood vessels than by OCTA may be displayed. Further, a diagnosis result may be information relating to the medical examination and treatment policy or the like regarding the subject. Furthermore, a diagnosis result may be information including at least one of, for example, the diagnosis, a kind or state (extent) of a lesion (abnormal site), the position of a lesion in the image, the position of a lesion relative to a region of interest, the findings (interpretation findings or the like), grounds for the diagnosis (affirmative medical support information or the like), and grounds for negating the diagnosis (negative medical support information). At this time, for example, a diagnosis result that is more likely than a diagnosis result such as a diagnosis that was input according to an instruction from the examiner may be displayed as medical support information. Further, in a case where a plurality of kinds of medical images were used, for example, the kind of medical image that can be grounds for the diagnosis result may be distinguishably displayed.

Note that, a diagnosis result may be a result generated using a learned model (diagnosis result generating engine, or a learned model for generating diagnosis results) obtained by learning using diagnosis results for medical images as training data. Further, the learned model may be a model obtained by learning using training data including a medical image and a diagnosis result for the medical image, or training data including a medical image and a diagnosis result for a medical image of a different kind from the relevant medical image or the like. Further, a configuration may be adopted so that a diagnosis result obtained using a high quality image generated by a learned model for improving image quality is displayed.

In addition, input data included in the training data may be a high quality image generated by a learned model for improving image quality, or may be a set composed of a low quality image and a high quality image. Further, the training data may be, for example, data obtained by labeling (performing annotation to) input data for which information including at least one kind of information among the diagnosis, a kind or state (extent) of a lesion (abnormal site), the position of a lesion in the image, the position of a lesion relative to a region of interest, the findings (interpretation findings or the like), grounds for the diagnosis (affirmative medical support information or the like), and grounds for negating the diagnosis (negative medical support information) is adopted as correct answer data (of supervised learning). Note that, a configuration may be adopted so that a diagnosis result obtained by a learned model for diagnosis result generation is displayed in response to an instruction from the examiner.

Further, the display controlling unit 250 in the various embodiments and modifications described above may cause an object recognition result (object detection result) or a segmentation result with respect to a partial region of a site of interest, an artifact region, or an abnormal site or the like as described above to be displayed on a report screen in a display screen. At such time, for example, a rectangular frame or the like may be superimposed around an object on the image and displayed. Further, for example, a color or the like may be superimposed on an object on the image and displayed. Note that, an object recognition result or a segmentation result may be a result generated using a learned model (object recognition engine, learned model for object recognition, segmentation engine, or learned model for segmentation) obtained by learning using training data in which information that indicates object recognition or segmentation is labeled (annotated) on a medical image as correct answer data. Note that, the aforementioned analysis result generation or diagnosis result generation may be realized by utilizing the aforementioned object recognition result or segmentation result. For example, processing for generating an analysis result or for generating a diagnosis result may be performed with respect to a site of interest obtained by object recognition processing or segmentation processing.

Further, in the case of detecting an abnormal site, a generative adversarial networks (GAN) or a variational auto-encoder (VAE) may be used. For example, a DCGAN (Deep Convolutional GAN) that is composed of a generator that is obtained by learning to generate a tomographic image, and a discriminator that is obtained by learning to distinguish between a new tomographic image which the generator generated and a real front image of the ocular fundus can be used as a machine learning model.

In the case of using a DCGAN, for example, the discriminator subjects an input tomographic image to encoding to convert the tomographic image into a latent variable, and the generator generates a new tomographic image based on the latent variable. Thereafter, a difference between the input tomographic image and the new tomographic image that was generated can be extracted as an abnormal site. Further, in the case of using a VAE, for example, an input tomographic image is converted into a latent variable by encoding the tomographic image using an encoder, and a new tomographic image is generated by decoding the latent variable using a decoder. Thereafter, a difference between the input tomographic image and the new tomographic image that was generated can be extracted as an abnormal site. Note that, although an example of input data has been described taking a tomographic image as one example, a fundus image or a front image of the anterior ocular segment or the like may also be used as the input data.

In addition, the image processing unit 220 may detect an abnormal site using a convolutional auto-encoder (CAE). In the case of using a CAE, the same image is learned as input data and ground truth during learning. Thus, when an image in which there is an abnormal site is input to the CAE during estimation, an image is output in which there is no abnormal site according to the learning tendency. Thereafter, a difference between the image input to the CAE and the image output from the CAE can be extracted as an abnormal site. Note that, in this case also, not only a tomographic image, but also a fundus image or a front image of the anterior ocular segment or the like may be used as the input data.

In these cases, the image processing unit 220 can generate, as information relating to an abnormal site, information relating to a difference between a medical image obtained using a generative adversarial network or an auto-encoder with respect to each different region identified by segmentation processing or the like, and a medical image input to the generative adversarial network or auto-encoder. Thus, it can be expected that the image processing units 220 will quickly and accurately detect an abnormal site. Here, examples of the auto-encoder include a VAE and a CAE. For example, the image processing unit 220 can generate, as information relating to an abnormal site, information relating to a difference between a medical image obtained using a generative adversarial network or an auto-encoder from various medical images, and a medical image input to the generative adversarial network or the auto-encoder. Further, for example, the display controlling unit 250 can cause information relating to a difference between a medical image obtained using a generative adversarial network or an auto-encoder from various medical images, and a medical image input to the generative adversarial network or the auto-encoder to be displayed as information relating to an abnormal site on the display unit 270.

Further, in the case of a diseased eye, the image features will differ according to the kind of disease. Therefore, learned models used in the various examples and modifications described above may be generated and prepared for each kind of disease or each abnormal site. In this case, for example, the controlling unit 200 can select a learned model to be used for processing, according to an input (instruction) such as the kind disease or the abnormal site of the eye to be examined from the operator. Note that, a learned model that is prepared for each kind of disease or each abnormal site is not limited to a learned model that is to be used for detecting retina layers or for generating a region label image or the like, and for example may be a learned model that is to be used in an engine for evaluating an image or in an engine for analysis or the like. At such time, the controlling unit 200 may identify the kind of disease or an abnormal site of an eye to be examined from an image using a separately prepared learned model. In this case, the controlling unit 200 can automatically select a learned model to be used in the aforementioned processing based on the kind of disease or the abnormal site that was identified using the separately prepared learned model. Note that, a learned model for identifying the kind of disease or an abnormal site of the eye to be examined can perform learning using pairs of training data for which a tomographic image or a fundus image or the like is adopted as input data, and kinds of diseases or abnormal sites in these images are adopted as ground truth. In this case, with respect to the input data of the training data, a tomographic image or a fundus image or the like may be independently adopted as input data, or a combination of these images may be adopted as input data.

Further, particularly the learned model for diagnosis result generation may be a learned model obtained by learning using training data including input data in which a plurality of medical images of different kinds that are images of a predetermined site of a subject are taken as a set. At such time, for example, input data in which a motion contrast front image of the fundus and an intensity front image (or intensity tomographic image) are taken as a set is conceivable as input data included in the training data. Further, for example, input data in which a tomographic image (B-scan image) of the fundus and a color fundus image (or fluorescence fundus image) are taken as a set is conceivable as input data included in the training data. In addition, the plurality of medical images of different kinds may be of any kind as long as the medical images were obtained by different modalities, different optical systems, or different principles or the like.

Furthermore, particularly the learned model for diagnosis result generation may be a learned model obtained by learning using training data including input data in which a plurality of medical images of different sites of a subject are taken as a set. At such time, for example, input data in which a tomographic image (B-scan image) of the fundus and a tomographic image (B-scan image) of the anterior ocular segment are taken as a set is conceivable as input data included in the training data. Further, for example, input data in which a three-dimensional OCT image (three-dimensional tomographic image) of the macula of the fundus and a tomographic image obtained by circular scanning (or raster scanning) of the optic nerve head of the fundus are taken as a set is also conceivable as input data included in the training data.

Note that, the input data included in the training data may be a plurality of medical images of different sites of the subject and of different kinds. At such time, for example, input data in which a tomographic image of the anterior ocular segment and a color fundus image are taken as a set is conceivable as input data included in the training data. Further, the various learned models described above may be learned models obtained by learning using training data including input data in which a plurality of medical images of different imaging angles of view that are images of a predetermined site of the subject are taken as a set. Further, input data included in the training data may be data obtained by joining together a plurality of medical images obtained by time-dividing a predetermined site into multiple regions, such as in the case of a panorama image. At such time, by using a wide-angle image such as a panorama image as training data, the result of each processing can be enhanced since there is a possibility that a feature value of the image can be acquired with good accuracy for reasons such as the fact that the amount of information is greater than in the case of a narrow-angle image. For example, a configuration is adopted so that, at the time of estimation (the time of prediction), in a case where abnormal sites are detected at a plurality of positions in a wide-angle image, enlarged images of the respective abnormal sites can be sequentially displayed. By this means, since abnormal sites at a plurality of positions can be efficiently checked, for example, the convenience of the examiner can be enhanced. For example, a configuration may be adopted so that, at such time, it is possible for the examiner to select the respective positions on the wide-angle image at which an abnormal site was detected, and to display an enlarged image of the abnormal site at a selected position. Further, input data included in the training data may be input data in which a plurality of medical images obtained at different dates and times of a predetermined site of the subject are taken as a set.

Further, a display screen on which at least one result among an analysis result, a diagnosis result, an object recognition result and a segmentation result described above is to be displayed is not limited to the report screen. Such a display screen may be, for example, at least one display screen among an imaging confirmation screen, a display screen for follow-up observation, and a preview screen for performing various kinds of adjustments before imaging (a display screen on which various kinds of live moving images are displayed) and the like. For example, by causing the aforementioned at least one result obtained using the various learned models described above to be displayed on the imaging confirmation screen, the examiner can check an accurate result even immediately after imaging. Further, for example, a configuration may be adopted so that, when a specific object is recognized, a frame that surrounds the recognized object is displayed in a superimposed manner on a live moving image. At this time, in a case where information (for example, a numerical value indicating a percentage) that indicates the degree of certainty of the object recognition result exceeds a threshold value, for example, the recognized object may be emphatically displayed such as by the color of the frame surrounding the object being changed. By this means, the examiner can easily distinguish the object on the live moving image. Further, changing the display between a low quality image and a high quality image described above may be, for example, changing the display between an analysis result for a low quality image and an analysis result for a high quality image.

The various learned models described above can be obtained by machine learning using training data. For example, deep learning which is composed of a multi-level neural network is one kind of machine learning. Further, for example, a convolutional neural network (CNN) can be used for at least a part of a multi-level neural network as a mechanical learning model. In addition, technology pertaining to auto-encoders may be used for at least a part of a multi-level neural network. Furthermore, technology pertaining to back-propagation (error back-propagation method) may be used for learning. Further, a technique (dropout) that randomly deactivates respective units (respective neurons) may be used for learning. Further, a technique (batch normalization) that normalizes the data transmitted to each layer of the multi-layer neural network before an activation function (for example, a ReLu function) is applied may be used for learning. However, the machine learning is not limited to deep learning, and any learning may be employed as long as the learning uses a model that is capable of, by itself, extracting (representing) a feature value of training data such as an image by learning. Here, the term "machine learning model" refers to a learning model according to a machine learning algorithm such as deep learning. Further, the term "learned model" refers to a model which, with respect to a machine learning model according to any machine learning algorithm, trained (performed learning) using appropriate training data in advance. However, it is assumed that the learned model is not a model that does not perform further learning, and is a model that can also perform incremental learning. Further, the term "training data" refers to data composed of pairs of input data and ground truth (correct answer data). Here, training data is also referred to as "teaching data" in some cases, and there are also cases where correct answer data is referred to as "teaching data".

Note that, a GPU can perform efficient arithmetic operations by performing parallel processing of larger amounts of data. Therefore, in a case where learning is performed a plurality of times using a learning model such as deep learning, it is effective to perform processing with a GPU. Thus, in the present modification, a GPU is used in addition to a CPU for processing by the image processing units 220 that are an example of a learning unit (not illustrated). Specifically, when a learning program including the learning model is executed, learning is performed by the CPU and the GPU cooperating to perform arithmetic operations. Note that, with respect to the processing of the learning unit, arithmetic operations may be performed by only the CPU or the GPU. Further, a processing unit (estimating unit) that executes processing using the various learned models described above may also using a GPU, similarly to the learning unit. The learning unit may also include an error detecting unit and an updating unit (not illustrated). The error detecting unit obtains an error between output data that is output from the output layer of the neural network according to input data that is input to the input layer, and correct answer data. The error detecting unit may be configured to calculate an error between the output data from the neural network and the correct answer data using a loss function. Further, based on an error obtained by the error detecting unit, the updating unit updates combining weighting factors between nodes of the neural network or the like so that the error becomes small. The updating unit updates the combining weighting factors or the like using, for example, the error back-propagation method. The error back-propagation method is a method that adjusts combining weighting factors between the nodes of each neural network or the like so that the aforementioned error becomes small.

Further, a U-Net type machine learning model that has a function of an encoder that is composed of a plurality of levels including a plurality of downsampling layers, and a function of a decoder that is composed of a plurality of levels including a plurality of upsampling layers can be applied as a machine learning model to be used for image quality improving or segmentation or the like. In a U-Net type machine learning model, positional information (spatial information) that has been made ambiguous in a plurality of levels configured as an encoder is configured (for example, using a skip connection) so that the information can be used in levels of the same dimension (levels corresponding to each other) in a plurality of levels configured as a decoder.

In addition, for example, an FCN (fully convolutional network) or a SegNet or the like can also be used as a machine learning model to be used for image quality improving or segmentation or the like. Further, a machine learning model that performs object recognition in region units may be used according to a desired configuration. As a machine learning model that performs object recognition, for example, RCNN (Region CNN), Fast-RCNN, or Faster-RCNN can be used. In addition, YOLO (You Only Look Once) or SSD (Single Shot Detector, or Single Shot Multi-Box Detector) can also be used as a machine learning model that performs object recognition in region units.

Further, the machine learning model may be, for example, a capsule network (CapsNet). In this case, in a common neural network, by configuring each unit (each neuron) so as to output a scalar value, the neural network is configured so that, for example, spatial information relating to spatial positional relationships (relative positions) between features in an image is reduced. By this means, for example, learning can be performed in which the influence of local distortion or parallel displacement in an image is reduced. On the other hand, in a capsule network, each unit (each capsule) is configured so as to output spatial information as a vector, and for example, is configured so that spatial information is held. By this means, for example, learning can be performed in which spatial positional relationships (relative positions) between features in an image is taken into consideration.

Furthermore, the image quality improving engine (learned model for improving image quality) may be a learned model obtained by incremental learning using training data including at least one high quality image generated by an image quality improving engine. At such time, a configuration may be adopted that enables a selection as to whether or not a high quality image is to be used as training data for incremental learning to be made by an instruction from the examiner. Note that, these configurations are not limited to a learned model for improving image quality, and are also applicable to various kinds of learned models described above. Further, a learned model for generating correct answer data which generates correct answer data such as labeling (annotation) may be used to generate correct answer data used for learning by the various kinds of learned models described above. At such time, the learned model for generating correct answer data may be a learned model obtained by performing (sequential) incremental learning of correct answer data obtained w % ben the examiner performed labeling (annotation). In other words, the learned model for generating correct answer data may be a learned model obtained by performing incremental learning of training data in which data before labeling is adopted as input data, and data after labeling is adopted as ground truth. Further, in the case of a plurality of consecutive frames such as a moving image, a configuration may also be adopted so as to modify a result with respect to a frame for which it is determined that the accuracy of the result is low taking into account the results of object recognition or segmentation of the preceding and following frames. At such time, a configuration may be adopted so as to perform incremental learning of the modified result as correct answer data in accordance with an instruction from the examiner.

Note that, in the various embodiments and modifications described above, in a case where partial region (for example, sites of interest, artifact regions, or abnormal sites or the like) of an eye to be examined is detected using a learned model for object recognition or a learned model for segmentation, predetermined image processing can also be performed for each detected region. For example, let us consider a case of detecting at least two regions among a vitreous body region, a retina region and a choroid region. In this case, when performing image processing such as contrast adjustment with respect to the at least two regions that were detected, adjustment that is suitable for the respective regions can be performed by using different image processing parameters for the respective regions. By displaying an image on which adjustment suitable for the respective regions was performed, the operator can more appropriately diagnose a disease or the like in each region. Note that, with regard to a configuration that uses image processing parameters that differ for each detected region, for example, such a configuration may also be similarly applied with respect to regions of an eye to be examined which were detected without using a learned model.

(Modification 10)

A configuration may be adopted so that, on a preview screen in the various embodiments and modifications described above, various learned models described above is used for every at least one frame of a live moving image. At such time, a configuration may be adopted so that, in a case where a plurality of live moving images of different sites or different kinds are displayed on the preview screen, learned models that correspond to the respective live moving images are used. By this means, for example, since the processing time can be shortened even for a live moving image, the examiner can obtain highly accuracy information prior to the start of imaging. Therefore, for example, since failures of re-imaging and the like can be reduced, the accuracy and efficiency of diagnosis can be improved.

Note that, the plurality of live moving images may include for example, a moving image of the anterior ocular segment for alignment in the XYZ-directions, and a front moving image of the fundus for focus adjustment or OCT focus adjustment of a fundus observation optical system. Further, the plurality of live moving images may also include, for example, a tomographic moving image of the fundus for coherence gate adjustment in OCT (adjustment of the optical path length difference between the measurement optical path length and the reference optical path length) and the like. At such time, a configuration may be adopted so that various kinds of adjustment mentioned above are performed so that a region detected using the learned model for object recognition or learned model for segmentation as described above satisfies a predetermined condition. For example, a configuration may be adopted so that various kinds of adjustment such as OCT focus adjustment are performed so that a value (for example, a contrast value or an intensity value) relating to a vitreous body region or a predetermined retinal layer such as the RPE that was detected using the learned model for object recognition or learned model for segmentation exceeds a threshold value (or becomes a peak value). Further, for example, a configuration may be adopted so that coherence gate adjustment in OCT is performed so that a vitreous body region or a predetermined retinal layer such as the RPE that was detected using the learned model for object recognition or learned model for segmentation is at a predetermined position in the depth direction.

In these cases, the image quality improving unit 224 can use a learned model to perform image quality improving processing with respect to a moving image to thereby generate a high quality moving image. Further, in a state in which the high quality moving image is displayed, the drive controlling unit 230 can perform drive control of an optical member, such as the reflection mirror 123 in the reference light optical system, for changing an imaging range so that a partial region of a site of interest or the like obtained by the segmentation processing or the like is located at a predetermined position in the display region. In such a case, the drive controlling unit 230 can automatically perform alignment processing based on highly accurate information so that a desired region is located at a predetermined position in the display region. Note that, the optical member that changes the imaging range may be, for example, an optical member that adjusts the coherence gate position, and specifically may be the reflection mirror 123 in the reference light optical system or the like. Further, the coherence gate position can be adjusted by an optical member that changes the optical path length difference between the measurement optical path length and the reference optical path length, and the optical member in question may be, for example, a mirror (not illustrated) or the like for changing the optical path length of the measuring light. Note that, the optical member that changes the imaging range may be, for example, a stage unit (not illustrated). Further, in accordance with an instruction relating to the start of imaging, the drive controlling unit 230 may control driving of the aforementioned scanning unit so that, during imaging or at the end of imaging, partial regions such as an artifact region obtained by segmentation processing or the like is imaged again (rescanned). Further, for example, a configuration may be adopted so as to automatically perform respective adjustments or automatically start imaging or the like when information (for example, a numerical value indicating a percentage) that indicates the likelihood of an object recognition result relating to a site of interest exceeds a threshold value. Further, for example, a configuration may be adopted so as to change (release an execution-prohibited state) to a state in which respective adjustments or the start of imaging or the like can be executed according to an instruction from the examiner, in a case where information (for example, a numerical value indicating a percentage) that indicates the likelihood of an object recognition result relating to a site of interest exceeds a threshold value.

Furthermore, a moving image to which various learned models described above can be applied is not limited to a live moving image, and for example the moving image may be a moving image stored (saved) in a storage 240. At such time, for example, a moving image obtained by performing alignment with respect to every at least one frame of a tomographic moving image of the fundus stored (saved) in a storage 240 may be displayed on the display screen. For example, in a case where it is desired to suitably observe the vitreous body, first, a reference frame based on conditions such as that the vitreous body is present as much as possible in the frame may be selected. At such time, each frame is a tomographic image (B-scan image) in the X-Z direction. Subsequently, a moving image in which other frames have been aligned in the X-Z direction with respect to the selected reference frame may be displayed on the display screen. At such time, for example, a configuration may be adopted so as to cause high quality images (high image quality frames) sequentially generated by the learned model for improving image quality for every at least one frame of the moving image to be consecutively displayed.

Note that, as methods for performing alignment among frames described above, the same method may be applied with respect to the method for performing alignment in the X-direction and the method for performing alignment in the Z-direction (depth direction), or the methods that are applied may all be different. In addition, alignment in the same direction may be performed a plurality of times by different methods. For example, a rough alignment may be performed, and thereafter a fine alignment may be performed. Further, the methods for alignment include, for example, (rough Z-direction) alignment using a retinal layer boundary obtained by subjecting a tomographic image (B-scan image) to segmentation processing, (fine X-direction or Z-direction) alignment using correlation information (similarity) between a plurality of regions obtained by dividing a tomographic image and a reference image, (X-direction) alignment using a one-dimensional projection image generated for each tomographic image (B scan image), and (X-direction) alignment using a two-dimensional front image. Further, a configuration may be adopted so as to perform fine alignment in sub-pixel units after rough alignment was performed in pixel units.

In this case there is a possibility that, during various kinds of adjustment, the imaging target such as the retina of the eye to be examined could not yet be successfully imaged. Thus, since there is a large difference between the medical image input to the learned model and the medical image used as training data, there is a possibility that a high quality image was not accurately obtained. Therefore, a configuration may be adopted so that when an evaluation value such as a value obtained when the image quality of a tomographic image (B scan) is evaluated exceeds a threshold value, display of a high-quality moving image (consecutive display of high image quality frames) is automatically started. Further, a configuration may be adopted so that when an evaluation value such as a value obtained when the image quality of a tomographic image (B scan) is evaluated exceeds a threshold value, the image quality improving button is changed to a state (active state) in which the button can be selected by the examiner.

Further, a configuration may be adopted in which different learned models for improving image quality are prepared for each imaging mode for which scanning patterns or the like are different, and a learned model for improving image quality that corresponds to a selected imaging mode is selected. Further, one learned model for improving image quality obtained by learning using training data including various medical images obtained in different imaging modes may be used.

(Modification 11)

Further, in the various embodiments and modifications described above, in a case where a learned model is performing incremental learning, there is a probability that it will be difficult to output (infer/predict) using the learned model which is performing incremental learning itself. For example, there is a probability that it will be difficult to execute image quality improving processing with an image quality improving unit while the image quality improving unit is performing incremental learning. Therefore, it is good to adopt a configuration so as to prohibit input of a medical image other than training data to the learned model which is performing incremental learning. Further, a learned model that is the same as the learned model before performing incremental learning may be prepared as a separate auxiliary learned model. At such time, it is good to adopt a configuration so that input of a medical image other than training data to the auxiliary learned model can be executed while incremental learning is being performed. After the incremental learning is completed, the learned model which performed the incremental learning is evaluated, and if there is no problem, it suffices to switch from the auxiliary learned model to the learned model which performed the incremental learning. Further, a configuration may be adopted so that the auxiliary learned model is used if there is a problem. Note that, as the evaluation of the learned model obtained after performing incremental learning, for example, a learned model for classification for classifying a high quality image obtained with the learned model for improving image quality separately from other kinds of images may be used. The learned model for classification is, for example, a learned model obtained by performing learning using training data that adopts a plurality of images including a high quality image obtained with the learned model for improving image quality and a low quality image as input data, and adopts data in which the kinds of these images have been labeled (annotated) as correct answer data. At such time, information (for example, a numerical value indicating a percentage) that indicates the degree of certainty for each kind of image included in the correct answer data during learning may be displayed in combination with the kinds of images of the input data at the time of estimation (time of prediction). Note that, apart from the aforementioned images, a high quality image for which the contrast was increased or noise was reduced or the like by averaging processing of a plurality of low quality images (for example, averaging processing of a plurality of low quality images that were aligned and obtained) may be included as input data of the learned model for classification. Further, as the evaluation of the learned model after performing incremental learning, for example, a plurality of high quality images obtained from the same image using each of the learned model after performing incremental learning and the learned model prior to performing incremental learning (the auxiliary learned model) may be compared, or analysis results for the respective pluralities of high quality images may be compared. At this time, for example, whether or not a result of comparing the respective pluralities of high quality images (one example of a change caused by incremental learning), or a result of comparing analysis results for the respective pluralities of high quality images (one example of a change caused by incremental learning) is within a predetermined range may be determined, and the determination result may be displayed.

Further, a configuration may be adopted so that learned models obtained by learning for respective imaged sites can be selectively utilized. Specifically, a plurality of learned models can be prepared that include a first learned model obtained using training data including a first imaged site (lung, eye to be examined, or the like), and a second learned model obtained using training data including a second imaged site that is different from the first imaged site. Further, the controlling unit 200 may have a selecting unit for selecting any one of this plurality of learned models. At such time, the controlling unit 200 may have a control unit for executing incremental learning with respect to a selected learned model. The control unit, in response to an instruction from the operator, can retrieve data in which an imaged site corresponding to a selected learned model and an image obtained by imaging the relevant imaged site form a pair, and execute learning in which the retrieved and obtained data is adopted as training data as incremental learning with respect to the selected learned model. Note that, an imaged site corresponding to a selected learned model may be a site obtained based on header information of data, or a site that is manually input by the examiner. Further, retrieval of data may be performed, for example, through a network from a server or the like of an external facility such as a hospital or a laboratory. By this means, incremental learning can be efficiently performed for each imaged site by using an image obtained by imaging an imaged site that corresponds to the learned model.

Note that, the selecting unit and the control unit may be constituted by a software module that is executed by a processor such as a CPU or an MPU of the controlling unit 200. Further, the selecting unit and the control unit may be constituted by a circuit that serves a specific function such as an ASIC or by an independent apparatus or the like.

Further, when obtaining training data for incremental learning through a network from an external server or the like of a facility or the like as described above, it is desired to reduce a decrease in reliability due to falsification or system trouble during incremental learning or the like. Therefore, the correctness of the training data for incremental learning may be detected by confirming the consistency by a digital signature or hashing. By this means the training data for incremental learning can be protected. At such time, in a case where the correctness of the training data for incremental learning could not be detected as the result of confirming the consistency by a digital signature or hashing, a warning to that fact is given and incremental learning is not performed using the training data in question. Note that, the server may be any form of server, such as a cloud server, a FOG server, or an edge server, regardless of the installation location thereof. Further, protection of data by confirming the consistency as described above, is not limited to training data for incremental learning, and is also applicable to data including medical images. In addition, an image management system may be configured so that transactions involving data including medical images between servers of a plurality of facilities are managed by a distributed network. Furthermore, an image management system may be configured so as to connect a plurality of blocks in which a transaction history and a hash value of the previous block are recorded together, in time series. Note that, cryptography (for example, lattice-based cryptography, or quantum cryptography using quantum key distribution) that is difficult to calculate even if a quantum computer based on a quantum gate system or the like is used may be utilized as a technique for confirming the consistency or the like.

(Modification 12)

In the various embodiments and modifications described above, an instruction from the examiner may be a voice instruction or the like in addition to a manual instruction (for example, an instruction using a user interface or the like). At such time, for example, a machine learning model including a speech recognition model (a speech recognition engine or a learned model for speech recognition) obtained by machine learning may be used. In addition, a manual instruction may be an instruction by character input using a keyboard, a touch panel, or the like. At such time, for example, a machine learning model including a character recognition model (a character recognition engine, a learned model for character recognition) obtained by machine learning may be used. Further, an instruction from the examiner may be an instruction by a gesture or the like. At such time, a machine learning model including a gesture recognition model (a gesture recognition engine, a learned model for gesture recognition) obtained by machine learning may be used.

Further, an instruction from the examiner may be a result of detection of the line of sight of the examiner on a display screen on the display unit 270 or the like. The line-of-sight detection result may be, for example, a pupil detection result using a moving image of the examiner obtained by imaging from around the display screen on the display unit 270. At such time, the pupil detection from the moving image may use an object recognition engine as described above. Further, an instruction from the examiner may be an instruction by brain waves, or a faint electric signal flowing through the body or the like.

In such a case, for example, the training data may be training data in which character data or voice data (waveform data) or the like indicating an instruction to display a result obtained by processing of various learned models as described above is adopted as input data, and an execution command for actually causing a result obtained by processing of various learned models to be actually displayed on a display unit is adopted as correct answer data. Further, the training data may be training data in which, for example, character data or voice data or the like indicating an instruction to display a high quality image obtained with a learned model for improving image quality is adopted as input data, and an execution command for displaying a high quality image and an execution command for changing the image quality improving button to an active state are adopted as correct answer data. Naturally, any kind of training data may be used as long as, for example, the instruction content indicated by the character data or voice data or the like and the execution command content correspond with each other. Further, voice data may be converted to character data using an acoustic model or a language model or the like. Further, processing that reduces noise data superimposed on voice data may be performed using waveform data obtained with a plurality of microphones. Further, a configuration may be adopted so that a selection between an instruction issued by characters or voice or the like and an instruction input using a mouse or a touch panel or the like can be made according to an instruction from the examiner. In addition, a configuration may be adopted so that a selection can be made to turn instruction by characters or voice or the like on or off according to an instruction from the examiner.

In this case, the machine learning includes deep learning as described above, and for example, a recurrent neural network (RNN) can be used as at least a part of the multi-layer neural network. Here, as an example of the machine learning model according to the present modification, an RNN that is a neural network that handles time-series information will be described with reference to FIG. 18A and FIG. 18B. Further, a long short-term memory (hereinafter referred to as an "LSTM"), which is a kind of RNN, will be described with reference to FIG. 19A and FIG. 19B.

Figure 18B:
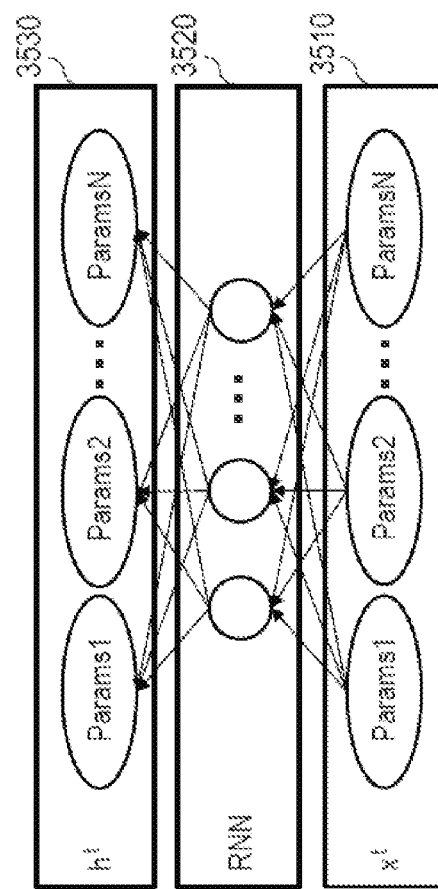
FIG. 18B is a view illustrating an example of the configuration of the neural network used as the machine learning model according to Modification 12.

FIG. 18A illustrates a structure of an RNN that is a machine learning model. An RNN 3520 has a loop structure in the network, and inputs data $x^t$3510 at time t, and outputs data $h^t$3530. Since the RNN 3520 has a loop function in the network, the state at the current time can be taken over to the next state, and hence time-series information can be handled. FIG. 18B illustrates an example of the input/output of parameter vectors at time t. The data $x^t$3510 includes N pieces of data (Params1 to ParamsN). Further, the data $h^t$3530 output by the RNN 3520 includes N pieces of data (Params1 to ParamsN) corresponding to the input data.

Figure 19A:
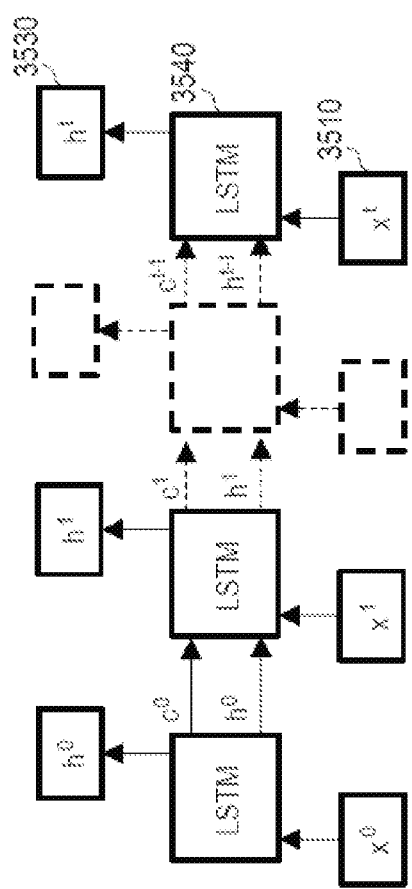
FIG. 19A is a view illustrating an example of the configuration of the neural network used as the machine learning model according to Modification 12.

However, since the RNN cannot handle long-time information during back propagation, the LSTM may be used. The LSTM can learn long-term information by providing a forget gate, an input gate, and an output gate. FIG. 19A illustrates a structure of the LSTM. In an LSTM 3540, information that the network takes over at the next time t is an internal state $c^{t-1}$ of the network called a cell and output data $h^{t-1}$. Note that lowercase letters (c, h, x) in the figure represent vectors.

Figure 19B:
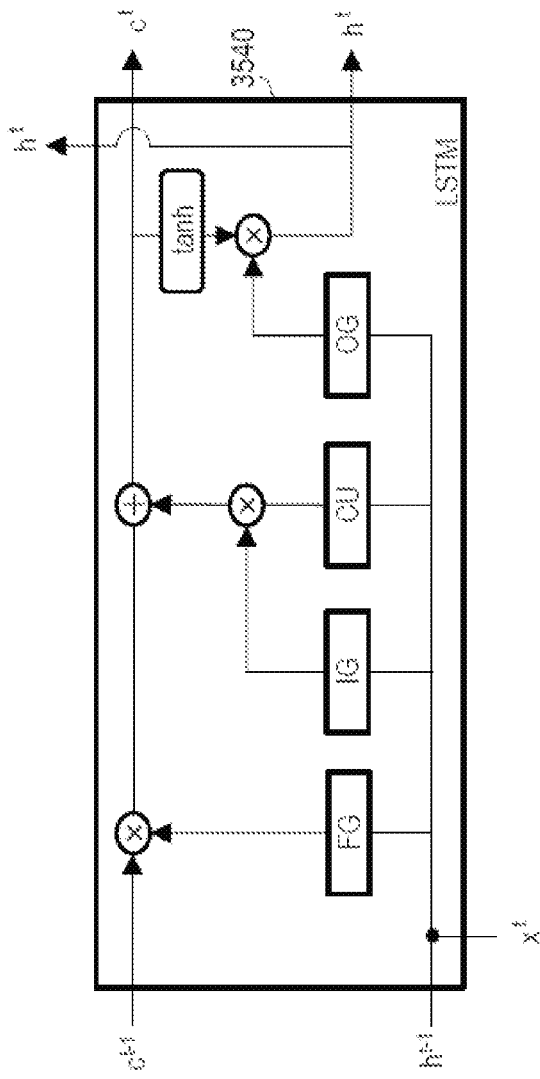
FIG. 19B is a view illustrating an example of the configuration of the neural network used as the machine learning model according to Modification 12.

Next, the LSTM 3540 is illustrated in detail in FIG. 19B. In FIG. 19B, reference characters FG denote a forget gate network, reference characters IG denote an input gate network, and reference characters OG denote an output gate network, and each of these networks is a sigmoid layer. Therefore, a vector in which each element has a value from 0 to 1 is output. The forget gate network FG determines how much past information is held, and the input gate network IG determines which value is to be updated. Reference characters CU denote a cell update candidate network, which is an activation function tanh layer. This creates a vector of new candidate values to be added to the cell. The output gate network OG selects an element of a cell candidate and selects how much information is to be transmitted at the next time.

Note that, the LSTM model described above is a basic form, and the present invention is not limited to the network illustrated here. The coupling between networks may be changed. A QRNN (quasi-recurrent neural network) may be used instead of an LSTM. In addition, the machine learning model is not limited to a neural network, and Boosting or Support Vector Machine or the like may be used. Further, in a case where an instruction from the examiner is input by characters or voice or the like, a technique relating to natural language processing (for example, Sequence to Sequence) may be applied. Further, a dialogue engine (a dialogue model or a learned model for dialogue) that responds to the examiner with an output such as text or voice may be applied.

Further, as a technique relating to natural language processing, a learned model obtained by pre-learning by unsupervised learning of document data may be used. Further, as a technique relating to natural language processing, a learned model obtained by further subjecting a learned model obtained by pre-learning to transfer learning (or fine-tuning) in accordance with the purpose may be used. Furthermore, for example. BERT (Bidirectional Encoder Representations from Transformers) may be applied as a technique relating to natural language processing. In addition, a model that is capable of, by itself, extracting (representing) the context (feature value) by predicting specific words in a sentence from the bidirectional context may be applied as a technique relating to natural language processing. Furthermore, a model that is capable of determining the relationship (continuity) of two sequences (sentences) in time series data that is input may be applied as a technique relating to natural language processing. Further, a model in which an encoder of a transformer is used in a hidden layer, and into and from which a vector sequence is input and output may be applied as a technique relating to natural language processing.

Here, an instruction from the examiner that can be applied in the present modification may be any instruction as long as the instruction is at least one instruction relating to changing the display of various images or analysis results, selection of a depth range for generating an en-face image, selection of whether or not to use an image as training data for incremental learning, selection of a learned model, and output (display or transmission or the like) or storage of results obtained using various learned models and the like as described in the various embodiments and modifications described above. Further, an instruction from the examiner that can be applied in the present modification is not only an instruction after imaging, and may be an instruction before imaging, and for example, may be an instruction relating to various adjustments, an instruction relating to the setting of various imaging conditions, or an instruction relating to the start of imaging. In addition, an instruction from the examiner that can be applied in the present modification may be an instruction relating to changing of a display screen (screen transition).

(Modification 13)

In the various embodiments and modifications described above, a high quality image or the like may be stored in the storage 240 in accordance with an instruction from the examiner. At such time, after the instruction from the examiner to save the high quality image or the like, when registering a file name, a file name that includes information (for example, characters) indicating that the image is an image generated by processing using a learned model for improving image quality (image quality improving processing) at any part of the file name (for example, the first part or the last part) may be displayed as a recommended file name in a state in which the file name can be edited according to an instruction from the examiner.

Further, when causing the display unit to display a high quality image on various display screens such as the report screen, a display indicating that the image being displayed is a high quality image generated by processing using a learned model for improving image quality may be displayed together with the high quality image. In this case, since a user can easily discern by the relevant display that the displayed high quality image is not the actual image obtained by imaging, misdiagnosis can be reduced and the diagnosis efficiency can be improved. Note that, a display indicating that a high quality image was generated by processing that used a learned model for improving image quality may be of any form as long as it is a display which makes it possible to distinguish between the input image and the high quality image generated by the relevant processing. Further, with regard to processing using various learned models as described above also, and not just processing using a learned model for improving image quality, a display indicating that the result which is being displayed was generated by processing using the relevant kind of learned model may be displayed together with the relevant result.

At such time, the display screen such as a report screen may be stored as image data in the storage 240 in accordance with an instruction from the examiner. For example, a report screen may be stored in the storage 240 as a single image in which high quality images or the like and a display indicating that these images are high quality images generated by processing using a learned model for improving image quality are displayed side by side.

Further, with respect to the display indicating that a high quality image was generated by processing that used a learned model for improving image quality, a display indicating what kind of training data the learned model for improving image quality used when performing learning may be displayed on the display unit 270. The display in question may include a description of the kinds of input data and correct answer data of the training data, or any display relating to the input data and the correct answer data such as an imaged site included in the correct answer data. Note that, with regard to processing using various learned models as described above also, and not just processing using a learned model for improving image quality, a display indicating what kind of training data the relevant kind of learned model used when performing learning may be displayed on the display unit 270.

Further, a configuration may be adopted so that information (for example, characters) indicating that the image was generated by processing using a learned model for improving image quality may be displayed or stored in a state in which the information is superimposed on the high quality image or the like. At such time, a place at which the information is superimposed on the image may be any place as long as the place is in a region (for example, at an edge of the image) which does not overlap with a region in which the site of interest or the like that is the imaging target is displayed. Further, a non-overlapping region may be determined, and the information may be superimposed in the determined region.

Further, a configuration may be adopted so that in a case where, as an initial display screen of the report screen, the default setting is set so that the image quality improving button enters an active state (image quality improving processing is set to "on"), a report image corresponding to the report screen that includes a high quality image or the like is transmitted to a server in accordance with an instruction from the examiner. Further, a configuration may be adopted so that in a case where the default setting is set so that the image quality improving button enters an active state, when an examination ends (for example, in a case where the imaging confirmation screen or the preview screen is changed to the report screen in accordance with an instruction from the examiner), a report image corresponding to the report screen that includes a high quality image or the like is (automatically) transmitted to a server. At such time, a configuration may be adopted so that a report image generated based on various kinds of settings of the default settings (for example, settings relating to at least one of the depth range for generating an en-face image on the initial display screen of the report screen, whether or not to superimpose an analysis map, whether or not the image is a high quality image, and whether or not to show a display screen for follow-up observation and the like) is transmitted to a server.

Note that, although a configuration that stores using the storage 240 has been described above, the storage 240 may be a data server on a network, a cloud-based storage or a database or the like. Further, display control of the display unit 270 may be executed through the storage 240, a data management medium or an image management system. Here, the image management system is an apparatus and a system which receive and store images that were imaged by an imaging apparatus and images that were subjected to image processing. An image management system can also transmit an image in response to a request from a connected apparatus, perform image processing on a stored image, and request another apparatus to carry out a request for image processing. Examples of the image management system can include a picture archiving and communication system (PACS). In particular, an image management system according to the foregoing modifications includes a database that is also capable of storing, together with a received image, various kinds of information such as information pertaining to the subject and the imaging time which is associated with the image. Further, the image management system is connected to a network and, in response to a request from another apparatus, can transmit and receive images, convert images, and transmit and receive various kinds of information associated with stored images. Furthermore, in the image management system, information (as described above, information that is superimposed on an image, described in a file name, or described in a header within a file) for identifying contents relating to learning in the various embodiments and modifications described above may be associated with an image and information. Thus, for example, whether or not a stored image is an image after processing using a learned model can be easily identified. Further, the image management system may be configured so that, when such kind of image data is received, the image management system confirms with the sender of the image data whether or not the received image data is data obtained by processing using a learned model. Further, the associated information may be learning model information (other processing, diseases, apparatuses, reading centers). Further, information that is stored and information that is displayed in the present modification may be learned image evaluation results (information pertaining to numerical values, evaluation contents, and incremental learning or the like) as described above.

(Modification 14)

In the various embodiments and modifications described above, among the various learned models described above, an image obtained with a first kind of learned model (for example, a high quality image, an image showing an analysis result such as an analysis map, an image showing an object recognition result, or an image showing a segmentation result) may be input to a second kind of learned model that is different from the first kind. At such time, a configuration may be adopted so that a result (for example, an analysis result, a diagnosis result, an object recognition result or a segmentation result) is generated by processing of the second kind of learned model.

Further, among the various learned models described above, an image to be input to a second kind of learned model that is different from a first kind of learned model may be generated from an image input to the first kind of learned model by using a result (for example, an analysis result, a diagnosis result, an object recognition result or a segmentation result) obtained by processing of the first kind of learned model. At such time, there is a high possibility that the generated image is an image that is suitable as an image for processing by the second kind of learned model. Therefore, the accuracy of an image (for example, a high quality image, an image showing an analysis result such as an analysis map, an image showing an object recognition result or an image showing a segmentation result) obtained when the generated image is input to the second kind of learned model can be enhanced.

Further, the various learned models described above may be learned models obtained by learning using training data including two-dimensional medical images of an object under examination. Furthermore, the various learned models may be learned models obtained by learning using training data including three-dimensional medical images of an object under examination.

Further, retrieval of similar case images utilizing an external database that is stored in a server or the like may be performed using an analysis result or a diagnosis result or the like, as a search key, obtained by processing of the learned models as described above. Note that, in a case where a plurality of images stored in the database are already being managed in a state in which respective feature values of the plurality of images have been attached as supplementary information by machine learning or the like, a similar case image search engine (a similar case image search model, or a learned model for similar case image searching) that utilizes an image itself as a search key may be used. For example, the controlling unit 200 can perform a search for a similar case image relating to the relevant medical image from among various medical images by using a learned model for similar case image searching (that is different from the learned model for improving image quality). Further, for example, the display controlling unit 250 can cause a similar case image obtained using the learned model for similar case image searching from among various medical images to be displayed on the display unit 270. At this time, the similar case image is, for example, an image with a feature value that is similar to the feature value of the medical image input to the learned model. Further, a plurality of similar case images may be retrieved, and the plurality of similar case images may be displayed in a condition in which the order in which the feature values are similar can be distinguished. Further, a configuration may be adopted so that the learned model for similar case image searching is subjected to incremental learning using training data that includes an image selected according to an instruction from the examiner from among a plurality of similar case images, and a feature value of the relevant image.

(Modification 15)

Note that, processing for generating motion contrast data in the aforementioned embodiments and modifications is not limited to a configuration in which the processing is performed based on intensity values of a tomographic image. The various kinds of processing described above may be applied with respect to an interference signal obtained with the OCT imaging unit 100, a signal obtained by subjecting an interference signal to Fourier transformation, a signal obtained by subjecting the relevant signal to any processing, and tomographic data including a tomographic image or the like based on these signals. In these cases also, similar effects as the effects of the aforementioned configurations can be obtained.

Although a fiber optical system that uses a coupler as a splitting unit is used, a spatial optical system that uses a collimator and a beam splitter may also be used. Further, the configuration of the OCT imaging unit 100 is not limited to the above described configuration, and some of the components included in the OCT imaging unit 100 may be provided as separate components from the OCT imaging unit 100.

Further, although in the foregoing embodiments and modifications the configuration of a Mach-Zehnder interferometer is used as the configuration of the interference optical system of the OCT imaging unit 100, the configuration of the interference optical system is not limited thereto. For example, the interference optical system of the OCT apparatus 1 may have the configuration of a Michelson interferometer.

In addition, while a spectral domain OCT (SD-OCT) apparatus which uses the SLD as a light source is described as the OCT apparatus in the foregoing embodiments and modifications, the configuration of the OCT apparatus according to the present invention is not limited thereto. For example, the present invention can also be applied to a swept source OCT (SS-OCT) apparatus which uses a wavelength-swept light source capable of sweeping a wavelength of emitted light, or any other kind of OCT apparatus. Further, the present invention can also be applied to a Line-OCT apparatus (or SS-Line-OCT apparatus) that uses line light. Furthermore, the present invention can also be applied to a full field-OCT apparatus (or an SS-full field-OCT apparatus) that uses area light.

Further, in the foregoing embodiments and modifications, the obtaining unit 210 obtains an interference signal that was obtained by the OCT imaging unit 100, or a three-dimensional tomographic image generated by the image processing unit 220. However, a configuration with which the obtaining unit 210 obtains these signals or images is not limited to the above described configuration. For example, the obtaining unit 210 may obtain these signals from a server or an imaging apparatus connected to the controlling unit through a LAN, a WAN, the Internet, or the like.

Note that, a learned model can be provided in the controlling unit 200, 900 or 1400 that is an image processing apparatus. A learned model can be constituted, for example, by a software module that is executed by a processor such as a CPU. Further, a learned model may be provided in a separate server that is connected to the controlling unit 200, 900 or 1400. In this case, the controlling unit 200, 900 or 1400 can perform image quality improving processing using the learned model by connecting to the server that includes the learned model through any network such as the Internet. Note that, a server in which the learned model is provided may be any form of server, such as a cloud server, a FOG server, or an edge server.
(Modification 16)

Further, images to be processed by an image processing apparatus or image processing method according to the various embodiments and modifications described above include medical images obtained using an arbitrary modality (imaging apparatus or imaging method). The medical images to be processed can include a medical image obtained by any imaging apparatus or the like, and images created by an image processing apparatus or an image processing method in accordance with the embodiments and modifications described above.

In addition, a medical image to be processed is an image of a predetermined site of a subject (examinee), and the image of the predetermined site includes at least one part of the predetermined site of the subject. The medical image may also include another site of the subject. The medical image may be a still image or a moving image, and may be a black and white image or a color image. In addition, the medical image may be an image representing the structure (form) of the predetermined site or may be an image representing a function of the predetermined site. Images that represent a function include, for example, an image representing hemodynamics (blood flow volume, blood flow velocity or the like) such as an OCTA image, a Doppler OCT image, an fMRI image, and an ultrasound Doppler image. Note that, the predetermined site of the subject may be determined according to the imaging target, and such predetermined sites include organs such as the human eye (eye to be examined), brain, lung, intestine, heart, pancreas, kidney, and liver, and any sites such as the head, chest, legs and arms.

Further, the medical image may be a tomographic image of the subject, or may be a front image. Examples of a front image include a front image of the fundus, a front image of the anterior ocular segment, a fundus image obtained by fluorescence imaging, and an en-face image generated using at least a partial range of data in the depth direction of the imaging target with respect to data obtained by OCT (three-dimensional OCT data). An en-face image may be an OCTA en-face image (motion contrast front image) generated using at least a partial range of data in the depth direction of the imaging target with respect to three-dimensional OCTA data (three-dimensional motion contrast data). Further, three-dimensional OCT data or three-dimensional motion contrast data is an example of three-dimensional medical image data.

Here, the term "motion contrast data" refers to data showing changes between a plurality of items of volume data obtained by controlling so that measuring light is scanned a plurality of times over the same region (same position) of an eye to be examined. At such time, the volume data is composed of a plurality of tomographic images obtained at different positions. The motion contrast data can then be obtained as volume data by, at respective positions that are different to each other, obtaining data showing changes between a plurality of tomographic images that were obtained at approximately the same position. Note that, in relation to OCT angiography (OCTA) that measures blood flow movement, a motion contrast front image is also referred to as an OCTA front image (OCTA en-face image), and motion contrast data is also referred to as OCTA data. The motion contrast data can be obtained, for example, as a variance value or a decorrelation value between two tomographic images or between interference signals corresponding to the two tomographic images, or as a value obtained by dividing a maximum value by a minimum value (maximum value/minimum value), and may be obtained by any known method. At such time, the two tomographic images can be obtained, for example, by controlling so that measuring light is scanned a plurality of times over the same region (same position) of the eye to be examined.

Further, an en-face image is, for example, a front image generated by projecting data of a range between two layer boundaries in the X- and Y-directions. At such time, the front image is generated by projecting or integrating data corresponding to a depth range that is at least a partial depth range of volume data (a three-dimensional tomographic image) obtained using light interference and that is defined based on two reference planes onto a two-dimensional plane. The en-face image is a front image generated by, among volume data, projecting data corresponding to a depth range which is determined based on detected retinal layers onto a two-dimensional plane. Note that, as a technique for projecting data corresponding to a depth range defined based on two reference planes onto a two-dimensional plane, for example, a technique can be used in which representative values of data within the relevant depth range are adopted as pixel values on a two-dimensional plane. In this case, the representative values can include values such as an average value, a median value or a maximum value of pixel values within a range in the depth direction of the region surrounded by the two reference planes. Further, the depth range pertaining to the en-face image may be, for example, a range that includes only a range corresponding to a predetermined number of pixels in a deeper direction or a shallower direction with reference to one of the two layer boundaries relating to the detected retinal layers. In addition, the depth range pertaining to the en-face image may be, for example, a range that has been changed (offset) according to an instruction of the operator from a range between the two layer boundaries relating to the detected retinal layers.

In addition, the term "imaging apparatus" refers to an apparatus for performing imaging to obtain an image to be used for diagnosis. Examples of an imaging apparatus include an apparatus that obtains an image of a predetermined site of the subject by irradiating the predetermined site with light, radioactive rays such as X-rays, electromagnetic waves, or ultrasonic waves or the like, and an apparatus that obtains an image of a predetermined site by detecting radioactive rays emitted from the subject. More specifically, examples of an imaging apparatus according to the various embodiments and modifications described above include at least an X-ray imaging apparatus, a CT apparatus, an MRI apparatus, a PET apparatus, a SPECT apparatus, an SLO apparatus, an OCT apparatus, an OCTA apparatus, a fundus camera and an endoscope.

Note that, a time domain OCT (TD-OCT) apparatus and a Fourier domain OCT (FD-OCT) apparatus may be included as examples of an OCT apparatus. Further, examples of a Fourier domain OCT apparatus may include a spectral domain OCT (SD-OCT) apparatus and a swept source OCT (SS-OCT) apparatus. Further, examples of the OCT apparatuses may include a Doppler-OCT apparatus. Further, an adaptive optics SLO (AO-SLO) apparatus and an adaptive optics OCT (AO-OCT) apparatus that use an adaptive optics system and the like may be included as examples of an SLO apparatus or an OCT apparatus, respectively. Furthermore, a polarization-sensitive SLO (PS-SLO) apparatus and a polarization-sensitive OCT (PS-OCT) apparatus and the like for visualizing information relating to polarization phase differences or depolarization may be included as examples of an SLO apparatus or an OCT apparatus, respectively. Further, a pathology microscope SLO apparatus and a pathology microscope OCT apparatus and the like may be included as examples of an SLO apparatus and an OCT apparatus, respectively. Further, a hand-held type SLO apparatus and a hand-held type OCT apparatus and the like may be included as examples of an SLO apparatus and an OCT apparatus, respectively. In addition, a catheter SLO apparatus and a catheter OCT apparatus and the like may be included as examples of an SLO apparatus and an OCT apparatus, respectively.

According to one of the embodiments and modifications of the present invention that are described above, an image can be generated that is more suitable for image diagnosis than an image generated according to the conventional technology.

Other Examples

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

At this time, examples of the processor or circuit may include a central processing unit (CPU), a microprocessing unit (MPU), a graphics processing unit (GPU), an application specific integrated circuit (ASIC), or a field programmable gateway (FPGA). Further, examples of the processor or circuit may include a digital signal processor (DSP), a data flow processor (DFP) or a neural processing unit (NPU).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image processing apparatus, comprising at least one of (a) one or more processors connected to one or more memories storing a program including instructions executed by the one or more processors and (b) circuitry configured to function as:
   an obtaining unit configured to obtain a first medical image of an object under examination;
   an image quality improving unit configured to generate, from the obtained first medical image, a second medical image with image quality higher than image quality of the obtained first medical image using a learned model;
   a comparing unit configured to compare an analysis result obtained by analyzing the obtained first medical image and an analysis result obtained by analyzing the generated second medical image; and
   a display controlling unit configured to cause a comparison result obtained by the comparing unit to be displayed on a display unit, wherein:
   the first medical image is a motion contrast en-face image in a range in a depth direction of an eye under examination; and
   the analysis result is at least one of a value relating to a blood vessel and a value relating to an avascular zone.

2. The image processing apparatus according to claim 1, wherein:
   the comparing unit calculates a difference between the analysis result for the obtained first medical image and the analysis result for the generated second medical image, and generates a color map image that is colored based on the difference; and the display controlling unit causes the color map image to be displayed on the display unit as the comparison result.

3. The image processing apparatus according to claim 2, wherein:

the display controlling unit causes the color map image to be displayed on the display unit in a superimposed manner on the obtained first medical image or the generated second medical image.

4. The image processing apparatus according to claim 1, wherein:

the comparing unit calculates a difference between the analysis result for the obtained first medical image and the analysis result for the generated second medical image; and the display controlling unit causes a warning to be displayed on the display unit as the comparison result if the difference is greater than a predetermined value or a number of pixels for which the difference is greater than a predetermined value is greater than another predetermined value.

5. The image processing apparatus according to claim 1, wherein:

the comparing unit calculates a difference between the analysis result for the obtained first medical image and the analysis result for the generated second medical image; and the display controlling unit causes a comparison result to be displayed on the display unit by causing a region in which the difference is greater than a predetermined value to be displayed on the display unit distinguishably from another region in which the difference is equal to or less than the predetermined value.

6. The image processing apparatus according to claim 1, wherein:

the obtaining unit obtains a plurality of first medical images that are en-face images generated based on information pertaining to a common range in a depth direction of an object under examination;

the image quality improving unit generates, from the obtained plurality of first medical images, a plurality of second medical images with image quality higher than image quality of the obtained plurality of first medical images using the learned model; and the comparing unit compares the obtained plurality of first medical images and the generated plurality of second medical images before and after the image quality improving processing.

7. The image processing apparatus according to claim 1, wherein training data of the learned model includes at least one of:

an image obtained by performing at least one kind of processing among averaging processing, maximum a posteriori processing, smoothing filter processing and gradation conversion processing;

an image imaged with an imaging apparatus with higher performance than an imaging apparatus used for imaging of a first medical image of an object under examination; and an image obtained by an imaging process including a number of steps that is greater than a number of steps of an imaging process for imaging a first medical image of an object under examination.

8. The image processing apparatus according to claim 1, wherein the display controlling unit causes at least one of:

an analysis result relating to the generated second medical image that is an analysis result generated using a learned model for generating analysis results that is obtained by using medical images of an object under examination, to be displayed on the display unit;

an object detection result relating to the generated second medical image that is an object detection result generated using a learned model for object recognition that is obtained by using medical images of an object under examination;

a segmentation result relating to the generated second medical image that is a segmentation result generated using a learned model for segmentation that is obtained by using medical images of an object under examination; and a similar case image relating to the generated second medical image that is a similar case image searched for by using a learned model for similar case image searching that is obtained by using medical images of an object under examination, to be displayed on the display unit.

9. The image processing apparatus according to claim 1, wherein:

the display controlling unit causes information relating to a difference between an image generated using a generative adversarial network or an auto-encoder into which the generated second medical image is input, and the generated second medical image input into the generative adversarial network or the auto-encoder to be displayed on the display unit as information relating to an abnormal site.

10. The image processing apparatus according to claim 1, wherein:

an instruction from an examiner relating to a processing by the image quality improving unit or an instruction from an examiner relating to control of a display based on the comparison result is information obtained using at least one learned model among a learned model for character recognition, a learned model for speech recognition and a learned model for gesture recognition.

11. The image processing apparatus according to claim 1, wherein:

a file name of the generated second medical image includes information indicating that the generated second medical image is an image generated by performing the image quality improving processing, in a state in which the information can be edited according to an instruction from an examiner.

12. An image processing method, comprising:

obtaining a first medical image of an object under examination;

generating, from the obtained first medical image, a second medical image with image quality higher than image quality of the obtained first medical image using a learned model;

comparing an analysis result obtained by analyzing the obtained first medical image and an analysis result obtained by analyzing the generated second medical image; and causing a comparison result obtained by the comparing to be displayed on a display unit, wherein:

the first medical image is a motion contrast en-face image in a range in a depth direction of an eye under examination; and the analysis result is at least one of a value relating to a blood vessel and a value relating to an avascular zone.

13. A non-transitory computer-readable medium having stored thereon a program that, upon being executed by a processor, causes the processor to execute each process of the image processing method according to claim 12.

* * * * *